United States Patent
Gregory et al.

(10) Patent No.: US 12,168,114 B2
(45) Date of Patent: Dec. 17, 2024

(54) FLUID DELIVERY DEVICE HAVING AN INSERTABLE PREFILLED CARTRIDGE

(71) Applicant: MannKind Corporation, Danbury, CT (US)

(72) Inventors: Christopher C. Gregory, Newtown, PA (US); Matthew P. Johnson, Boylston, MA (US); Robert L. Standley, Acton, MA (US)

(73) Assignee: MannKind Corporation, Danbury, CT (US)

( * ) Notice: Subject to any disclaimer, the term of this patent is extended or adjusted under 35 U.S.C. 154(b) by 0 days.

(21) Appl. No.: 18/296,162

(22) Filed: Apr. 5, 2023

(65) Prior Publication Data
US 2023/0233758 A1    Jul. 27, 2023

Related U.S. Application Data

(63) Continuation of application No. 16/783,609, filed on Feb. 6, 2020, now Pat. No. 11,660,387, which is a
(Continued)

(51) Int. Cl.
*A61M 5/142*    (2006.01)
*A61M 5/14*    (2006.01)
(Continued)

(52) U.S. Cl.
CPC .... *A61M 5/14248* (2013.01); *A61M 5/14526* (2013.01); *A61M 5/288* (2013.01);
(Continued)

(58) Field of Classification Search
CPC .......... A61M 5/14248; A61M 5/14526; A61M 5/288; A61M 5/1407; A61M 5/1452;
(Continued)

(56) References Cited

U.S. PATENT DOCUMENTS

| 6,102,887 A | 8/2000 | Altman |
| 7,455,664 B2 | 11/2008 | Fleury et al. |

(Continued)

FOREIGN PATENT DOCUMENTS

| CN | 1764485 A | 4/2006 |
| CN | 18748091 A | 8/2010 |

(Continued)

OTHER PUBLICATIONS

Extended European Search Report dated Jan. 20, 2017 for European Patent Application No. 14803383, 8 pages.
(Continued)

*Primary Examiner* — James D Ponton
(74) *Attorney, Agent, or Firm* — Morgan, Lewis & Bockius LLP

(57) ABSTRACT

A fluid delivery device includes a housing having a bottom surface configured to be coupled to the skin surface. The fluid delivery device includes a cartridge prefilled with a fluid and configured to be inserted into the housing. The cartridge has a septum configured to be generally perpendicular to the bottom surface when the cartridge is inserted in the housing. The fluid delivery device includes a needle assembly that has a needle that includes a fluid coupling end and a delivery end. The fluid coupling end of the needle is fluidly disengaged from the cartridge in an initial position. The delivery end of the needle extends past the plane of the bottom surface and the fluid coupling end of the needle extends through the septum in a deployed position.

7 Claims, 52 Drawing Sheets

Related U.S. Application Data continuation of application No. 14/786,009, filed as application No. PCT/US2014/040205 on May 30, 2014, now Pat. No. 10,596,313.

(60) Provisional application No. 61/923,957, filed on Jan. 6, 2014, provisional application No. 61/918,746, filed on Dec. 20, 2013, provisional application No. 61/857,415, filed on Jul. 23, 2013, provisional application No. 61/829,325, filed on May 31, 2013.

(51) Int. Cl.
*A61M 5/145* (2006.01)
*A61M 5/158* (2006.01)
*A61M 5/162* (2006.01)
*A61M 5/28* (2006.01)

(52) U.S. Cl.
CPC . *A61M 5/1407* (2013.01); *A61M 2005/14252* (2013.01); *A61M 2005/1426* (2013.01); *A61M 2005/14268* (2013.01); *A61M 5/1452* (2013.01); *A61M 2005/1585* (2013.01); *A61M 5/162* (2013.01); *A61M 2005/1623* (2013.01)

(58) Field of Classification Search
CPC ........ A61M 5/162; A61M 2005/14252; A61M 2005/1426; A61M 2005/14268; A61M 2005/1585; A61M 2005/1623
See application file for complete search history.

(56) References Cited

U.S. PATENT DOCUMENTS

| | | | |
|---|---|---|---|
| 7,455,667 | B2 | 11/2008 | Uhland et al. |
| 7,481,792 | B2 | 1/2009 | Gonnelli |
| 8,298,172 | B2 | 10/2012 | Nielsen et al. |
| 2002/0055711 | A1 | 5/2002 | Lavi et al. |
| 2003/0135159 | A1 | 7/2003 | Daily et al. |
| 2003/0187423 | A1* | 10/2003 | Wilkinson ........ A61M 37/0015 604/506 |
| 2004/0049129 | A1 | 3/2004 | Qi |
| 2005/0065466 | A1 | 3/2005 | Vedrine |
| 2006/0200073 | A1 | 9/2006 | Radmer et al. |
| 2010/0100048 | A1 | 4/2010 | Nielsen et al. |
| 2011/0060310 | A1 | 5/2011 | Prestrelski et al. |
| 2011/0137255 | A1 | 6/2011 | Nielsen et al. |
| 2011/0306929 | A1* | 12/2011 | Levesque .......... A61M 5/14248 604/150 |
| 2012/0022499 | A1 | 1/2012 | Anderson et al. |
| 2013/0006213 | A1 | 1/2013 | Amitz et al. |
| 2013/0046239 | A1 | 2/2013 | Gonnelli et al. |
| 2016/0082182 | A1 | 3/2016 | Gregory et al. |

FOREIGN PATENT DOCUMENTS

| | | |
|---|---|---|
| CN | 103025370 A | 4/2013 |
| CN | 102665799 A | 12/2014 |
| CN | 102665795 A | 3/2016 |
| EP | 1495775 A1 | 1/2005 |
| JP | 2007509661 A | 11/2007 |
| WO | 2011133823 A1 | 10/2011 |

OTHER PUBLICATIONS

First Office Action dated Apr. 26, 2017 for Chinese Patent Application No. 201480030789.3.
International Search Report and Written Opinion for International Patent Application No. PCT/US2014040205 dated Apr. 2, 2015.
Examination Report No. 1 dated Mar. 2, 2021 for Australiam Patent Application No. 2020201731, 5 pages.
Chinese First Office Action dated May 29, 2020 for Chinese Patent Application No. 2018103200036.6, 14 pages.

* cited by examiner

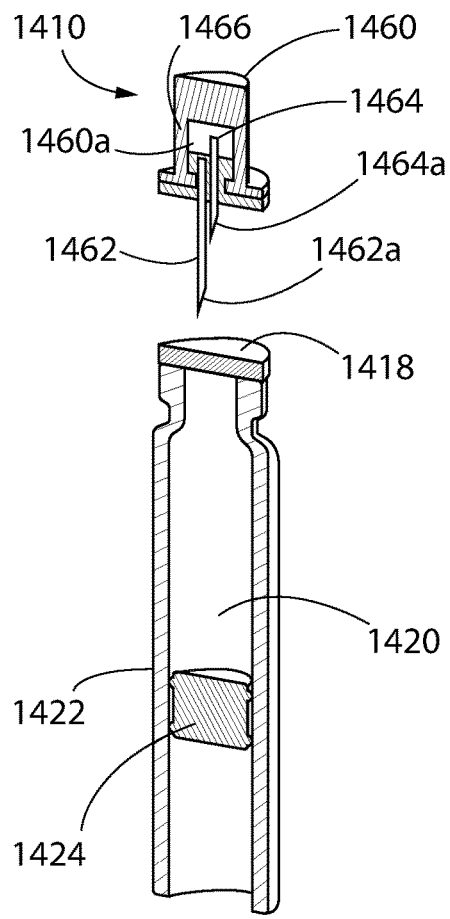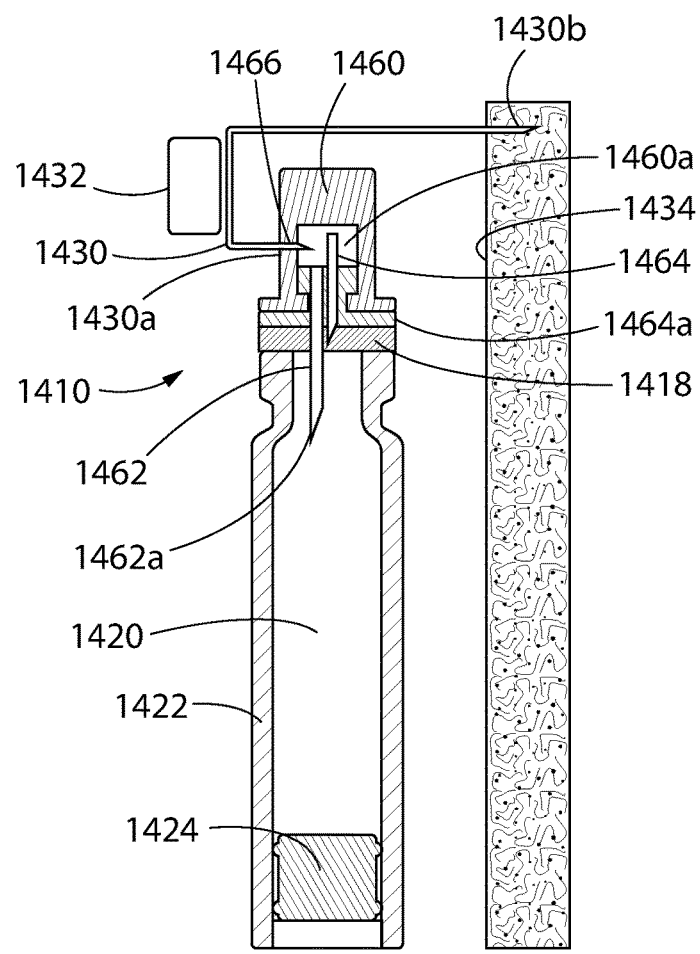
FIG. 14A  FIG. 14B
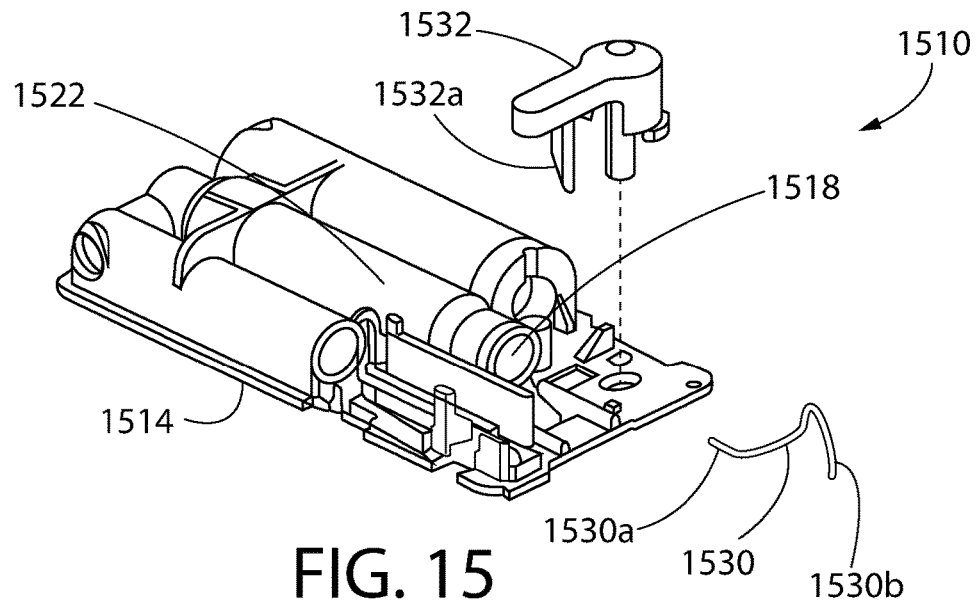
FIG. 15

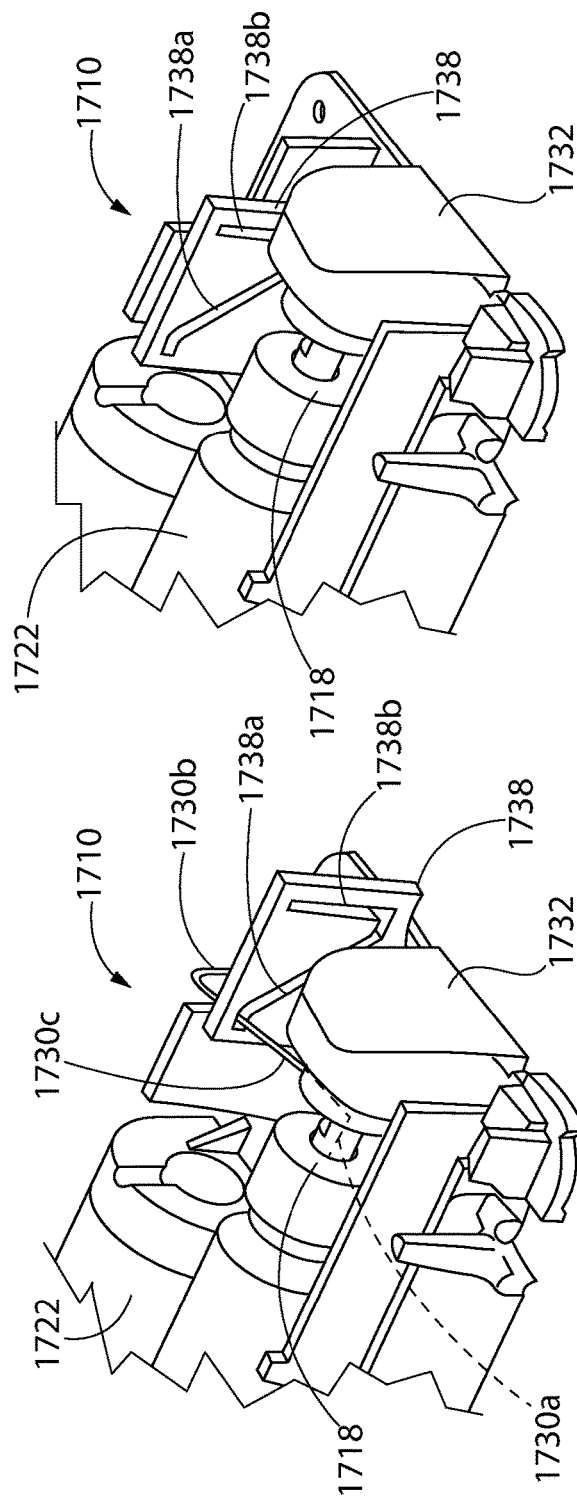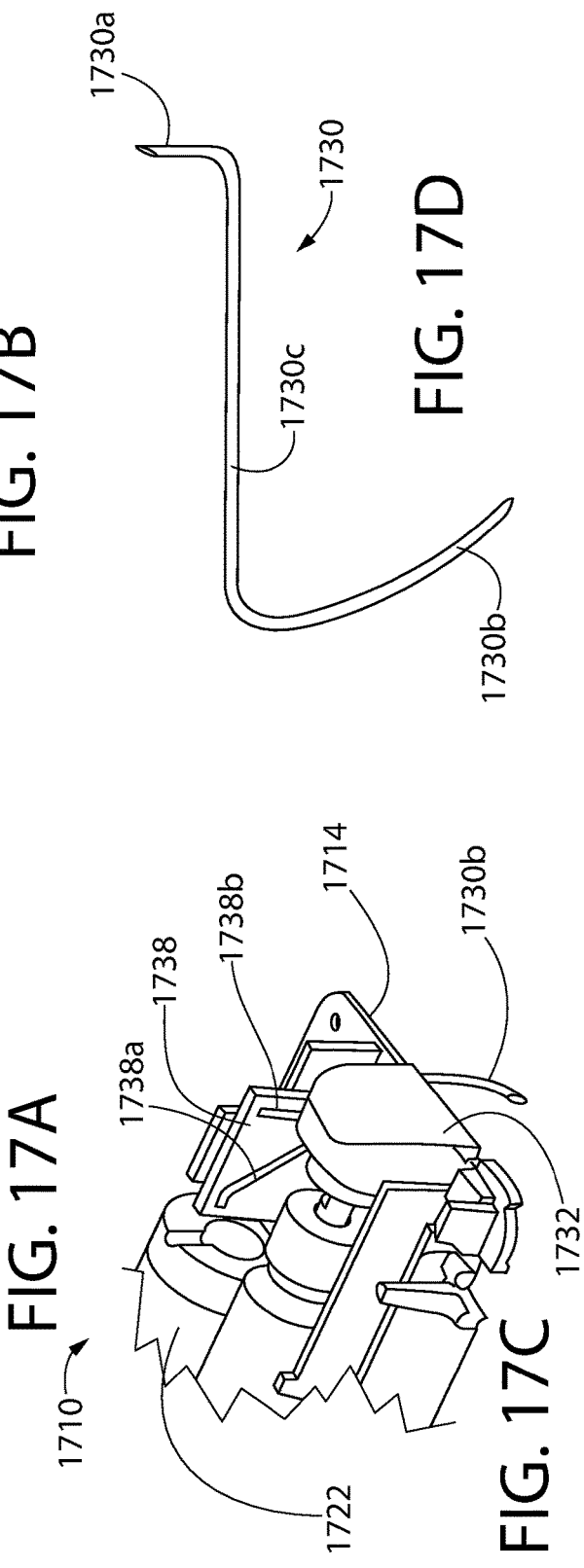

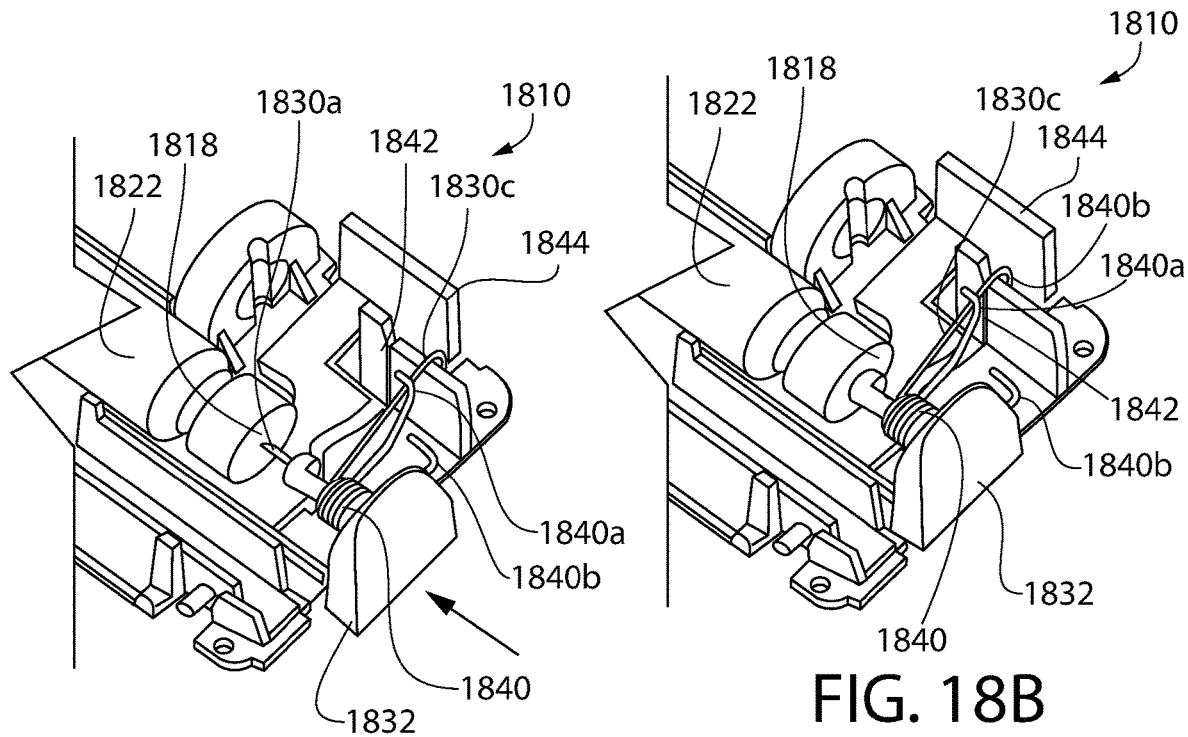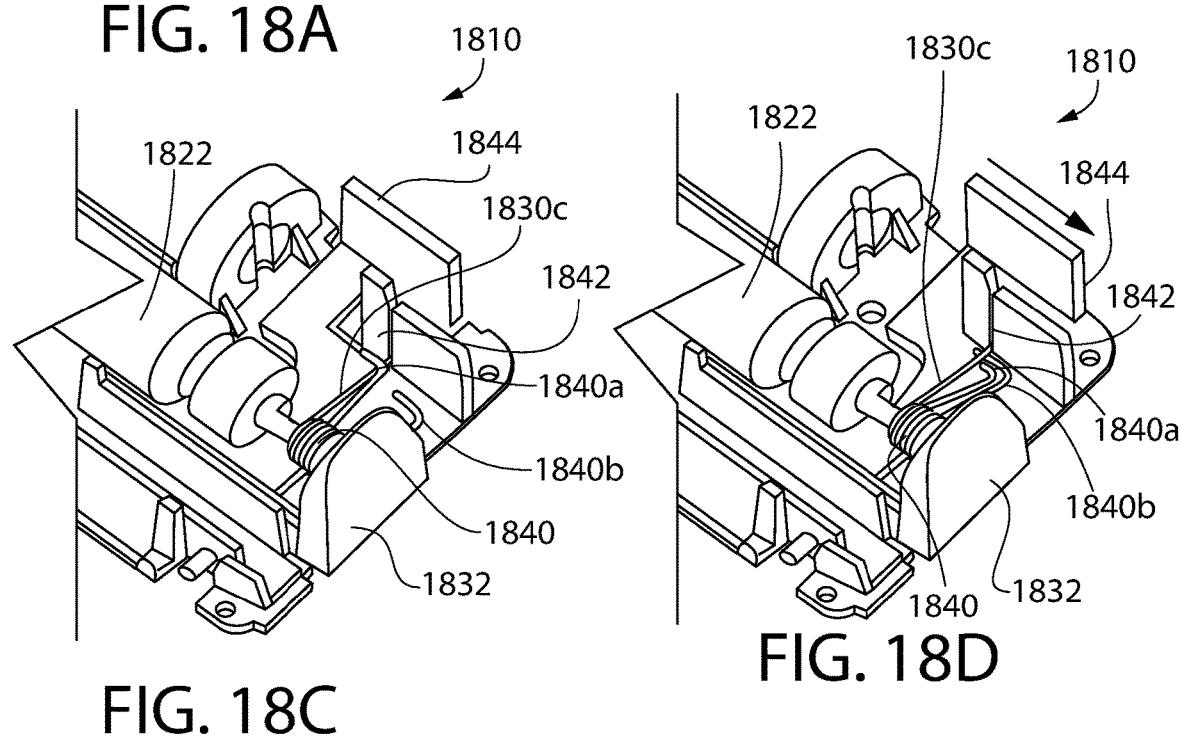

FLUID DELIVERY DEVICE HAVING AN INSERTABLE PREFILLED CARTRIDGE

CROSS-REFERENCE TO RELATED APPLICATIONS

This application is a continuation of U.S. patent application Ser. No. 16/783,609 filed
Feb. 6, 2020, which is a continuation of U.S. patent application Ser. No. 14/786,009 filed Oct. 21, 2015 now U.S. Pat. No. 10,596,313, which is a U.S. National Stage Entry of
International Patent Application No. PCT/US2014/040205 filed May 30, 2014, which in turn claims the benefit of U.S. Provisional Patent Application No. 61/829,325 filed May 31, 2013 entitled "Infusion Needle Mechanism For A Fluid Delivery Device", U.S. Provisional Patent Application No. 61/857,415 filed Jul. 23, 2013 entitled "Cartridge Insertion Mechanism For A
Fluid Delivery Device", U.S. Provisional Patent Application No. 61/918,746 filed Dec. 20, 2013 entitled "Cartridge Insertion Mechanism For A Fluid Delivery Device", and U.S. Provisional Patent Application No. 61/923,957 filed Jan. 6, 2014 entitled "Infusion Needle Mechanism For A Fluid Delivery Device" which are incorporated by reference herein in their entirety.

BACKGROUND OF THE INVENTION

The present invention generally relates to a fluid delivery device having an insertable prefilled cartridge.

BRIEF SUMMARY OF THE INVENTION

In one embodiment there is a fluid delivery device comprising: a housing having a bottom surface configured to be coupled to the skin surface; a cartridge prefilled with a fluid and configured to be inserted into the housing, the cartridge having a septum configured to be generally perpendicular to the bottom surface when the cartridge is inserted in the housing; and a needle assembly having a needle including a fluid coupling end and a delivery end, the fluid coupling end of the needle being fluidly disengaged from the cartridge in an initial position, the delivery end of the needle extending past the plane of the bottom surface in a deployed position and the fluid coupling end of the needle extending through the septum in the deployed position.

In one embodiment, the needle has a central portion extending between the fluid coupling end and the delivery end, the central portion bending around an axis that is coincident with the delivery end of the needle. In one embodiment, the central portion is helically shaped in the initial position. In one embodiment, the helical shape of the central portion is at least partially flattened toward the bottom surface when moving between the initial and deployed positions. In one embodiment, the central section of the needle loops around a moveable needle core. In one embodiment, the needle core is coupled to a lock member configured to releasably retain the needle in the initial and deployed positions. In one embodiment, the lock member is configured to retain the needle in a locked position after the deployed position, the lock member preventing re-deployment of the needle in the locked position. In one embodiment, the lock member is rotatable about the needle core and the rotational position of the lock member relative to the needle core determines if the needle is retained in or releasable from the initial and deployed positions.

In one embodiment, the housing includes a hydraulic fluid drive. In one embodiment, the hydraulic fluid drive includes a port configured to couple with the cartridge, the port having a seal that is closed prior to inserting the cartridge into the housing and released when the cartridge is coupled with the port, the cartridge including a piston moveable by the hydraulic fluid in the deployed position. In one embodiment, the seal includes a rotatable valve having one or more fluid passages configured to fluidly couple the hydraulic fluid drive and the piston. In one embodiment, the seal includes a slideable valve having one or more fluid passages configured to fluidly couple the hydraulic fluid drive and the piston.

In one embodiment, the one or more fluid passages are filled with a fluid prior to the cartridge being inserted into the housing. In one embodiment, the hydraulic fluid drive is fluidly coupled to an accumulator configured to allow thermal expansion and contraction of the drive fluid. In one embodiment, the accumulator is fluidly coupled to the accumulator when the seal is closed and fluidly disengaged from the hydraulic fluid drive when the seal is released. In one embodiment, the hydraulic fluid drive includes a first hydraulic chamber and a second hydraulic chamber, the first hydraulic chamber being fluid coupled to the second hydraulic chamber by a flow restrictor.

In one embodiment, the needle assembly includes a button, wherein actuation of the button moves the needle from the initial position to the deployed position. In one embodiment, the button is configured to be actuated by pressing the button toward the bottom surface. In one embodiment, the needle assembly is coupled to the cartridge and is configured to be inserted into the housing when the cartridge is inserted into the housing. In one embodiment, the needle assembly is configured to be coupled to the cartridge in the initial position after the cartridge is inserted into the housing. In one embodiment, a central portion of the needle is purposely deformed while moving from the initial position to the deployed position. In one embodiment, a central portion of the needle is purposely deformed while moving from the deployed position to a final position, the delivery end of the needle being retained within the housing in the final position. In one embodiment, the fluid coupling end of the needle and the delivery end of the needle extend in generally perpendicular directions in the deployed position.

In one embodiment there is a cartridge assembly for use with a fluid delivery device having a housing, the cartridge assembly comprises: a cartridge having a fluid and a septum configured to be generally perpendicular to a bottom surface of the housing when the cartridge is inserted in the housing; and a needle assembly coupled to the cartridge proximate the septum prior to the cartridge assembly being inserted into the housing, the needle assembly having a needle including a fluid coupling end and a delivery end, the fluid coupling end of the needle being generally perpendicular to the delivery end of the needle, the fluid coupling end of the needle being fluidly disengaged from the cartridge in an initial position, the delivery end of the needle configured to extend past the plane of the bottom surface in a deployed position and the fluid coupling end of the needle configured to extend through the septum in the deployed position.

In one embodiment, the needle has a central portion extending between the fluid coupling end and the delivery end, the central portion bending around an axis that is parallel with the delivery end of the needle. In one embodiment, the central portion is helically shaped in the initial position. In one embodiment, the helical shape of the central portion is at least partially flattened toward the bottom surface when moving between the initial and deployed positions. In one embodiment, the central section of the needle loops around a moveable needle core. In one embodiment, the needle assembly is coupled to a lock member and an assembly body, the lock member configured to releasably retain the needle within the assembly body in the initial position and a final position.

In one embodiment, the needle assembly includes a button, wherein actuation of the needle button moves the needle from the initial position to the deployed position. In one embodiment, a central portion of the needle is purposely deformed while moving from the initial position to the deployed position. In one embodiment, a central portion of the needle is purposely deformed while moving from the deployed position to a final position, the delivery end of the needle being retained within the housing in the final position. In one embodiment, the fluid coupling end of the needle and the delivery end of the needle extend in generally perpendicular directions in the deployed position.

BRIEF DESCRIPTION OF THE SEVERAL VIEWS OF THE DRAWINGS

The foregoing summary, as well as the following detailed description of embodiments of the fluid delivery device having an insertable prefilled cartridge will be better understood when read in conjunction with the appended drawings of an exemplary embodiment. It should be understood, however, that the invention is not limited to the precise arrangements and instrumentalities shown.

In the drawings:

FIG. 14A is a cross sectional exploded view of a portion of a fluid delivery device in accordance with an exemplary embodiment of the present invention;

FIG. 14B is a side cross sectional view of the fluid delivery device of FIG. 14A shown in a deployed position;

FIG. 15 is a top trimetric exploded view of a portion of a fluid delivery device in accordance with an exemplary embodiment of the present invention;

FIG. 17A is a trimetric view of a fluid delivery device in accordance with an exemplary embodiment of the present invention with the housing removed;

FIG. 17B is a first trimetric view of the fluid delivery device of FIG. 17A shown in the deployed position;

FIG. 17C is a second trimetric view of the fluid delivery device of FIG. 17A shown in the deployed position;

FIG. 17D is a trimetric view of the needle from the fluid delivery device of FIG. 17A;

FIG. 18A is a trimetric view of a fluid delivery device in accordance with an exemplary embodiment of the present invention with the housing removed and in an initial position;

FIG. 18B is a trimetric view of the fluid delivery device of FIG. 18A shown in the partially deployed position;

FIG. 18C is a trimetric view of the fluid delivery device of FIG. 18A shown in the deployed position;

FIG. 18D is a trimetric view of the fluid delivery device of FIG. 18A shown in the release position;

FIG. 39A is a cross section side view of a cartridge and manifold of a fluid delivery device in accordance with an exemplary embodiment of the present invention with the cartridge ready to be inserted;

FIG. 39B is a cross section side view of the cartridge and manifold shown in FIG. 39A with the cartridge inserted;

FIG. 40A is a trimetric view of a cartridge and manifold of a fluid delivery device in accordance with an exemplary embodiment of the present invention with the cartridge ready to be inserted;

FIG. 40B is a cross section side view of the cartridge and manifold shown in FIG. 40A with the cartridge ready to be inserted;

FIG. 40C is a cross section side view of the cartridge and manifold shown in FIG. 40B with the cartridge inserted and the pierced membrane removed for clarity;

FIG. 40D is a trimetric view of the cartridge and manifold shown in FIG. 40B with the cartridge inserted in a non-continuous manifold;

FIG. 40E is a cross section side view of the cartridge and manifold of a fluid delivery device in accordance with an exemplary embodiment of the present invention with the cartridge ready to be inserted;

FIG. 40F is a cross section side view of the cartridge and manifold shown in FIG. 39E with the cartridge inserted;

FIG. 41A is a trimetric view of a cartridge and manifold of a fluid delivery device interface in accordance with an exemplary embodiment of the present invention with the cartridge ready to be inserted;

FIG. 41B is a cross section side view of the cartridge and manifold shown in FIG. 41A with the cartridge ready to be inserted;

FIG. 41C is a trimetric view of the cartridge and manifold shown in FIG. 41A with the deformable face seal in its deformed state and the cartridge removed for clarity;

FIG. 41D is a cross section side view of the cartridge and manifold shown in FIG. 41A with the cartridge inserted and deformable face seal in its deformed configuration;

Figure 41A:
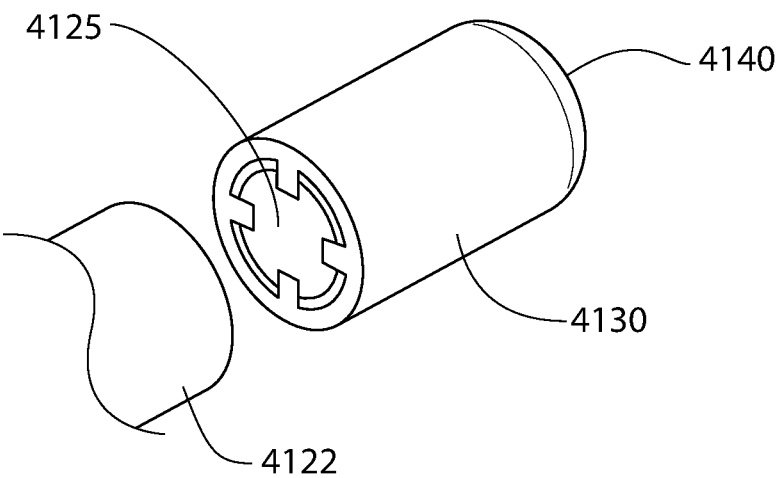
Figure 41B:
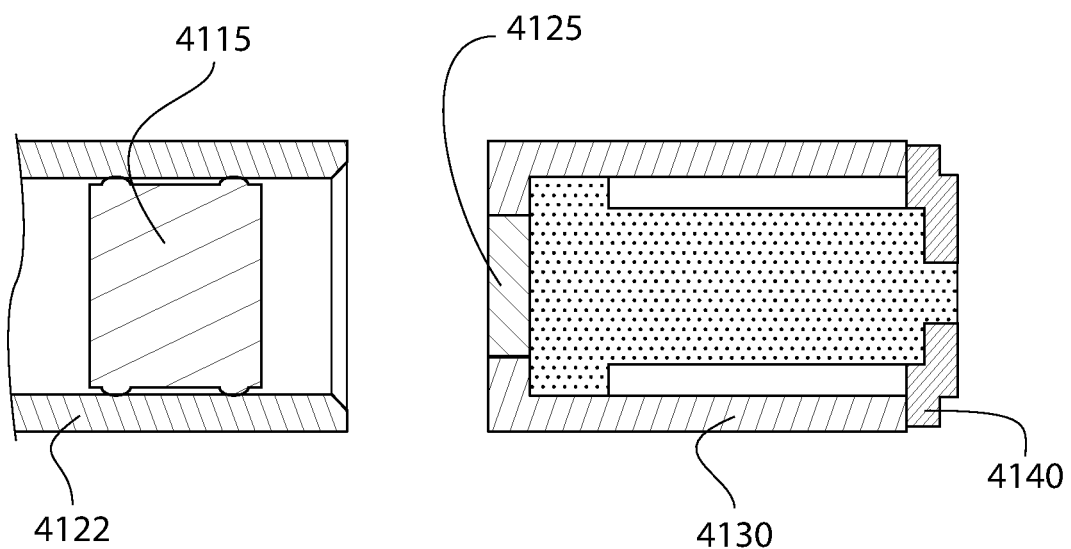
Figure 41C:
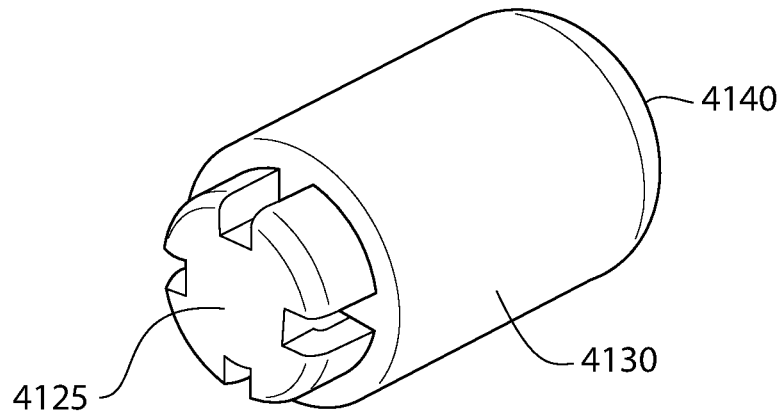
Figure 41D:
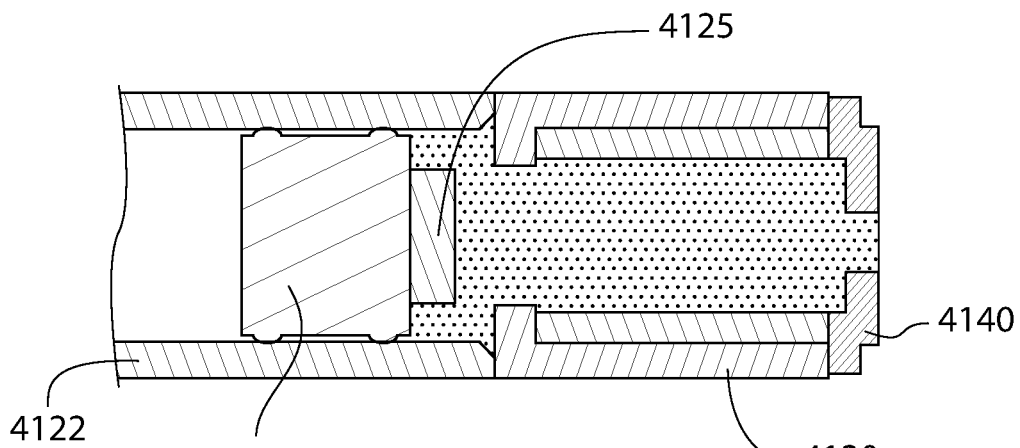
Figure 42A:
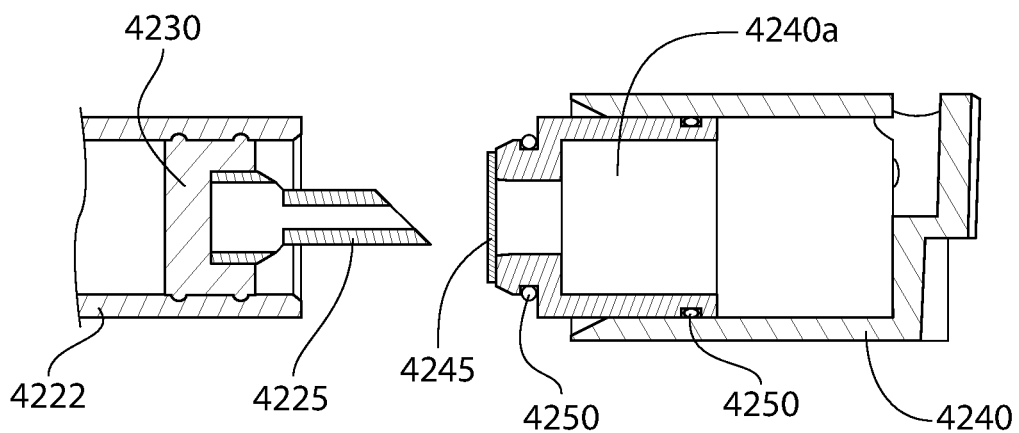
Figure 42B:
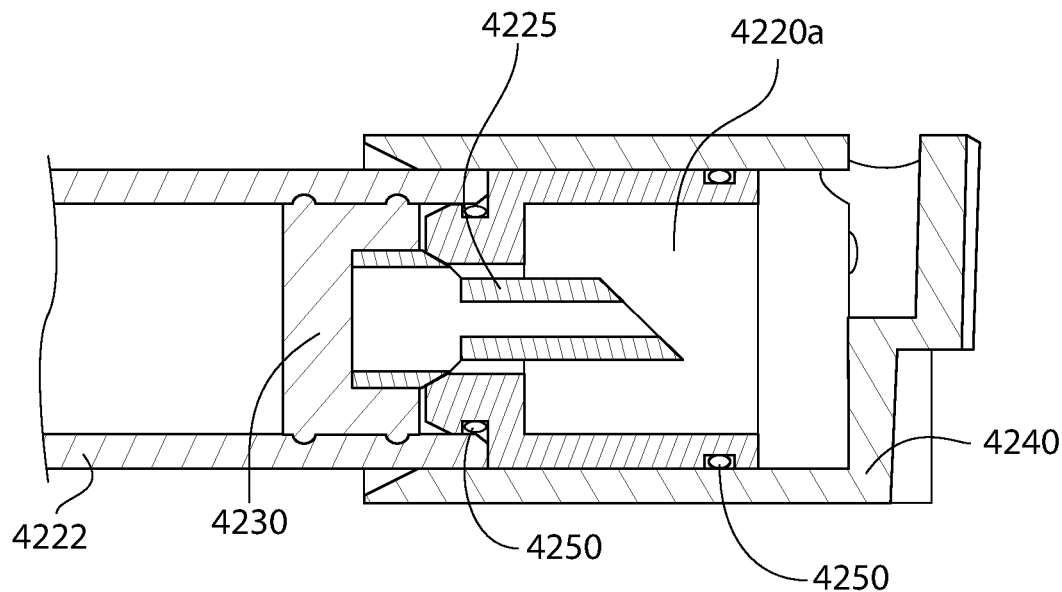
Figure 43A:
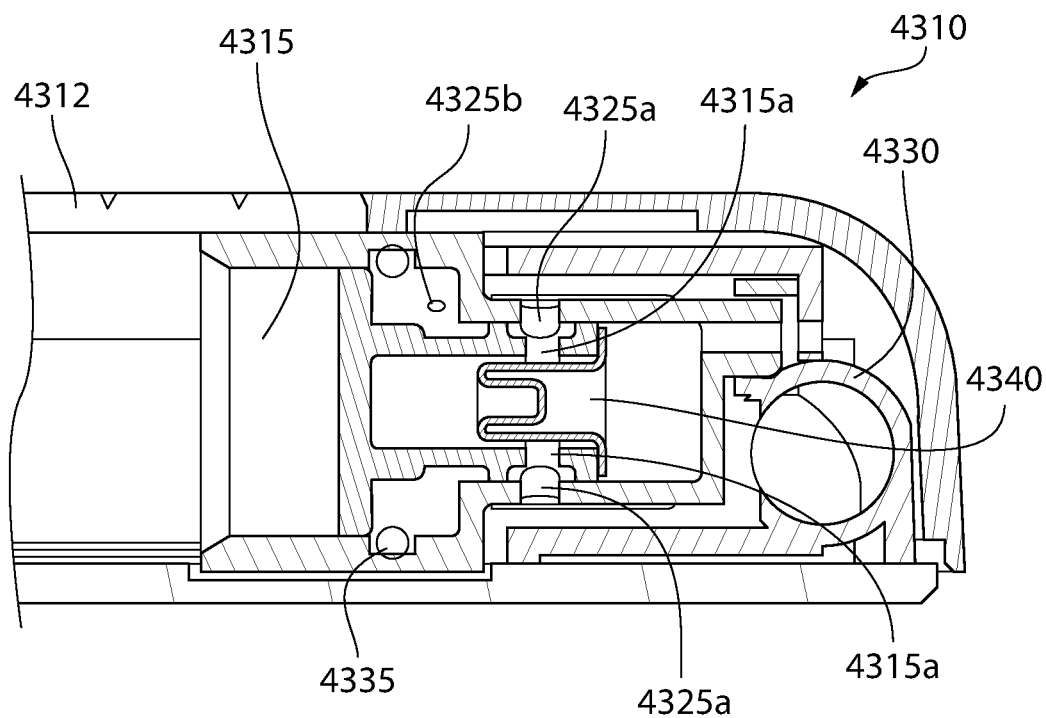
Figure 43B:
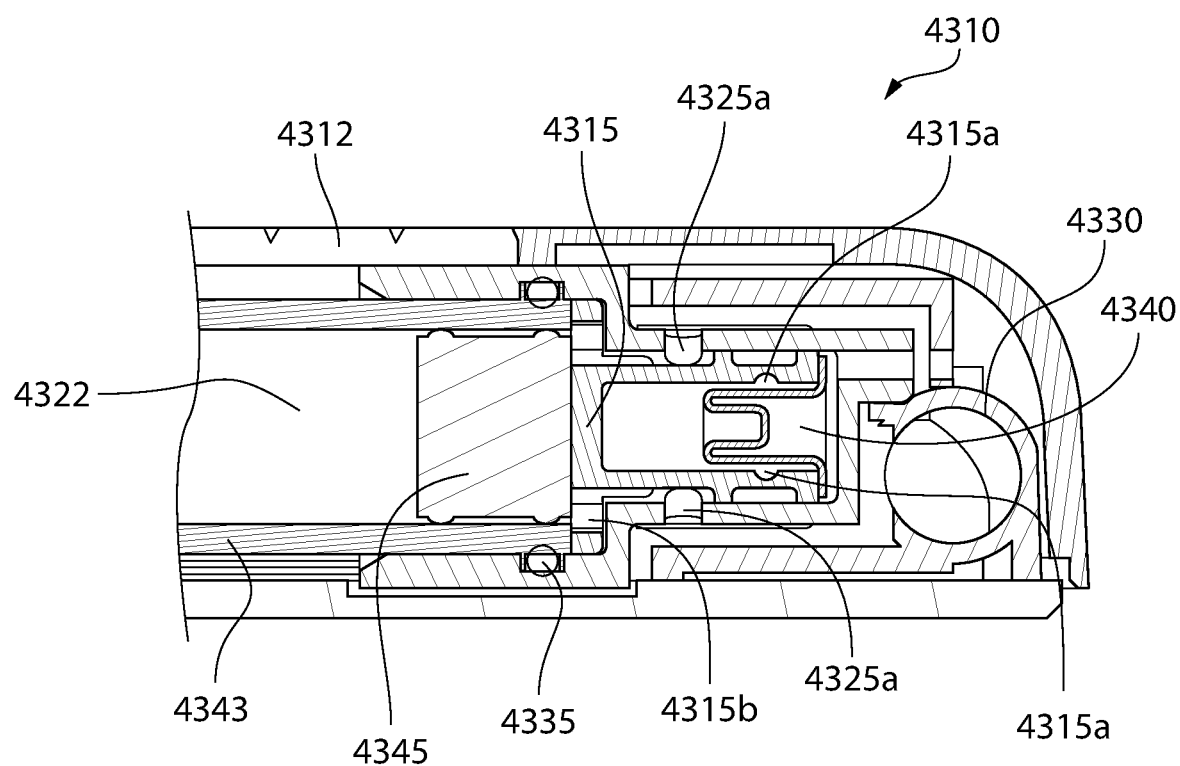

FIG. 42A is a cross section side view of a cartridge and manifold of a fluid delivery device in accordance with an exemplary embodiment of the present invention with the cartridge ready to be inserted;

FIG. 42B is a cross section side view of the cartridge and manifold shown in FIG. 41A with the cartridge inserted;

FIG. 43A is a cross section side view of a fluid delivery device in accordance with an exemplary embodiment of the present invention before inserting the cartridge; and FIG. 43B is a cross section side view of the fluid delivery device shown in FIG. 43A with the cartridge inserted.

DETAILED DESCRIPTION OF THE INVENTION

Referring to FIGS. 1-3B, an exemplary fluid delivery device 110 is shown. In one embodiment, fluid delivery device 110 is a discrete ambulatory insulin delivery pump. Fluid delivery device 110 may be single use, disposable and incapable of reuse. Fluid delivery device 110 may provide therapeutic capability in a small, single use, disposable package and can be produced using high volume manufacturing fabrication (e.g., injection molding) and assembly processes, allowing for low cost of goods. Devices of the invention can be used for a broad range of applications, including, but not limited to, clinical applications (e.g., administration of medicaments, etc.) and biomedical research (e.g., microinjection into cells, nuclear or organelle transplantation, isolation of single cells or hybridomas, etc.).

In one embodiment, fluid delivery device 110 is a device for dispensing, delivering, or administering the fluid or agent to the user or patient. The fluid may be a low viscosity gel agent and or a therapeutic agent. In one embodiment, the fluid is an analgesic agent. In one embodiment, the fluid is insulin of any type. In one embodiment, the fluid is a U100 insulin. In another embodiment the fluid is a U200 insulin. In another embodiment the fluid is a U300 insulin. In another embodiment, the fluid is a U500 insulin. In another embodiment the fluid is any insulin between U100 and U500. In other embodiments, the fluid may be, but is not limited to, opiates and/or other palliatives or analgesics, hormones, psychotropic therapeutic compositions, or any other drug or chemical whose continuous dosing is desirable or efficacious for use in treating patients. Single fluids and combinations of two or more fluids (admixed or co-administered) may be delivered using fluid delivery device 110. As used herein "patients" or "user" can be human or non-human animals; the use of fluid delivery device 110 is not confined solely to human medicine, but can be equally applied to veterinarian medicine.

Fluid delivery device 110 may dispense the fluid over a sustained period of time (i.e., basal delivery). In one embodiment, the fluid delivery rate is continuously or near continuously delivered to the user over the sustained period of time. Fluid delivery device 110 may also be capable of dispensing a supplementary amount of fluid, in addition to the basal amount, on demand, under patient control (i.e., bolus delivery). In one embodiment, the bolus amount delivered in a single, selectable administration is pre-determined. In some embodiments, fluid delivery device 110 is hydraulically actuated and comprises one or more reservoirs or chambers containing hydraulic fluid of a suitable viscosity for transferring power from one or more actuators to the fluid and controlling the delivery rate as discussed further below.

Figure 1:
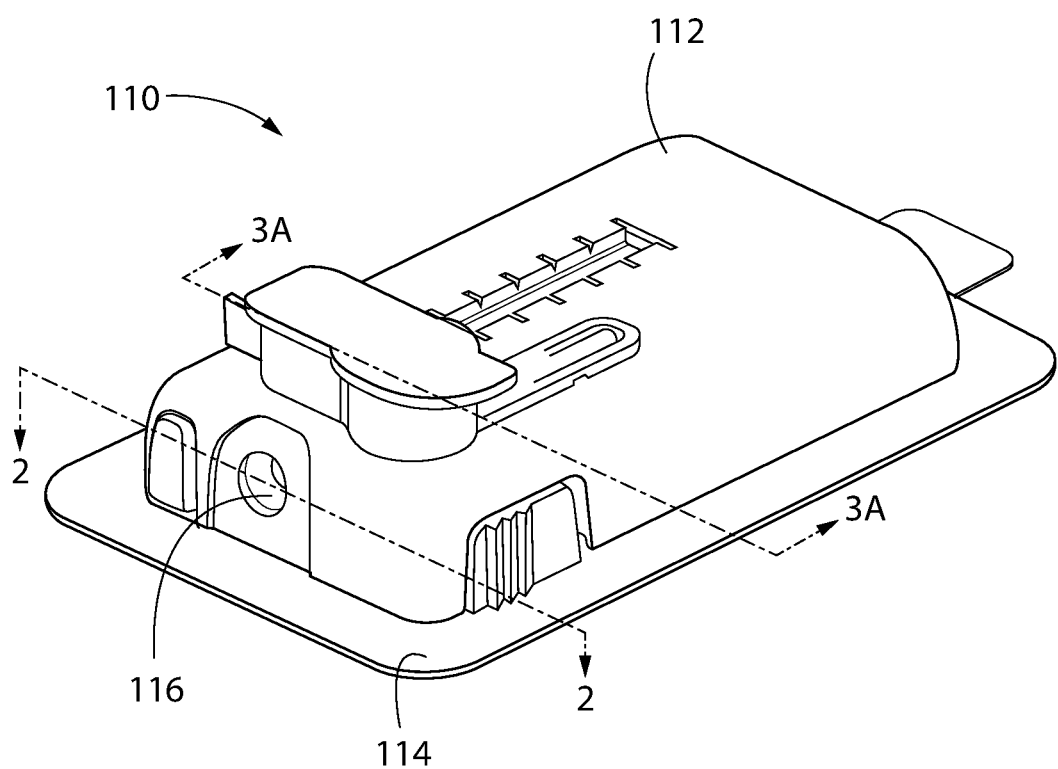
FIG. 1 is a trimetric view of a fluid delivery device.

Referring to FIG. 1, for example, the fluid delivery device 110 shown includes a housing 112 and an adhesive bottom surface 114 such as a foam pad.

Figure 2:
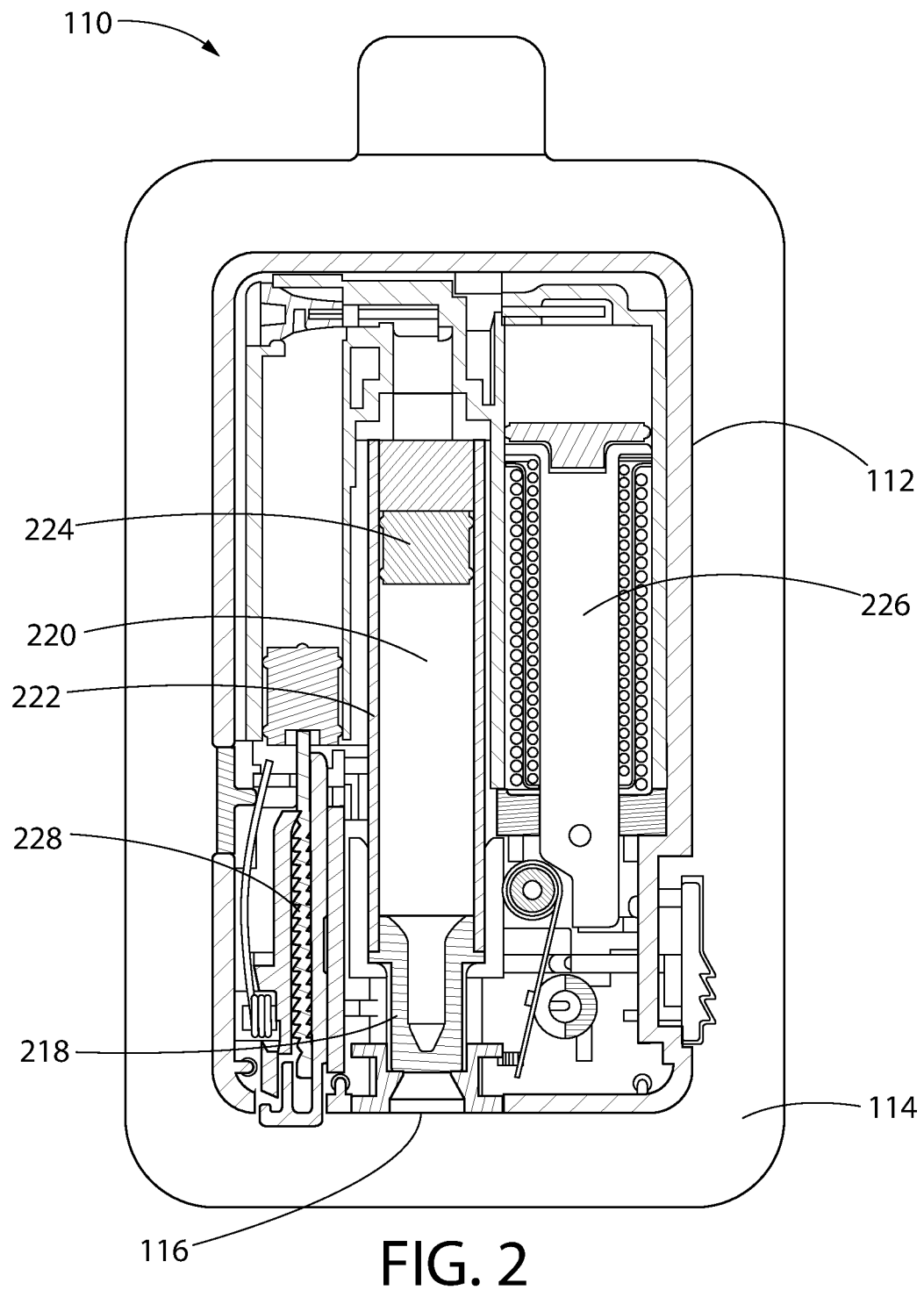
FIG. 2 is a top cross sectional view of the fluid delivery device shown in FIG. 1 taken along a plane indicated by line 2-2.

Referring to FIG. 2, fluid delivery device 110 includes a cartridge 222 having a fluid reservoir 220 containing the medicament. The fluid delivery device 110 may include one or more actuators 226 (such as a basal actuator), 228 (such as a bolus actuator) that act on and move piston 224 within cartridge 222.

Figure 3A:
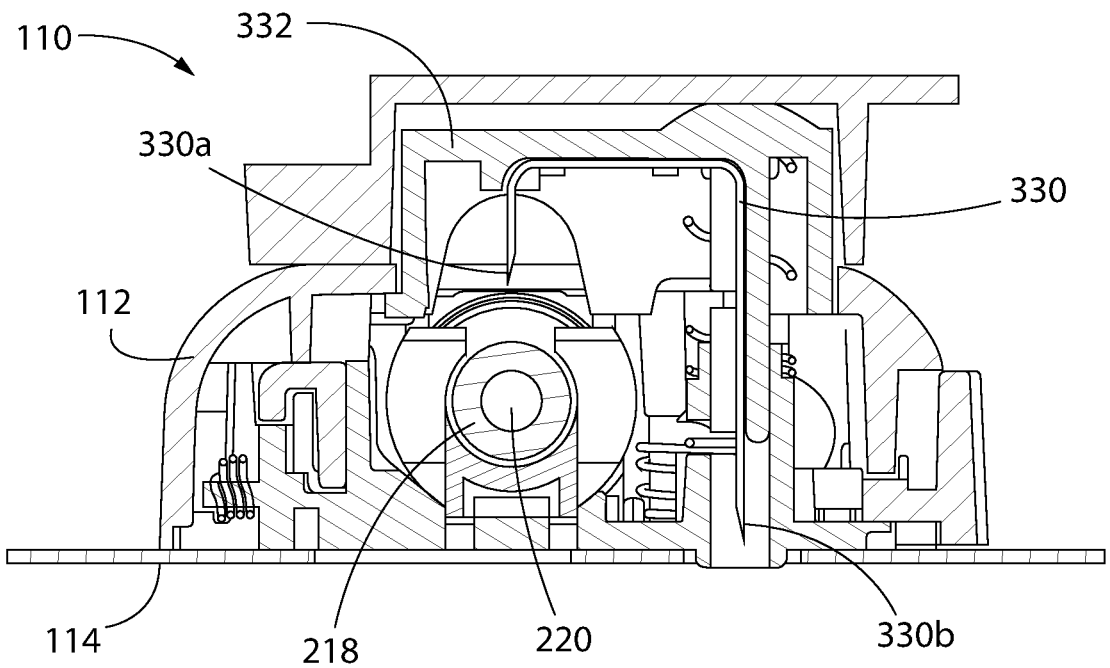
FIG. 3A is a front cross sectional view of the fluid delivery device shown in FIG. 1 taken along a plane indicated by line 3A-3A.
Figure 3B:
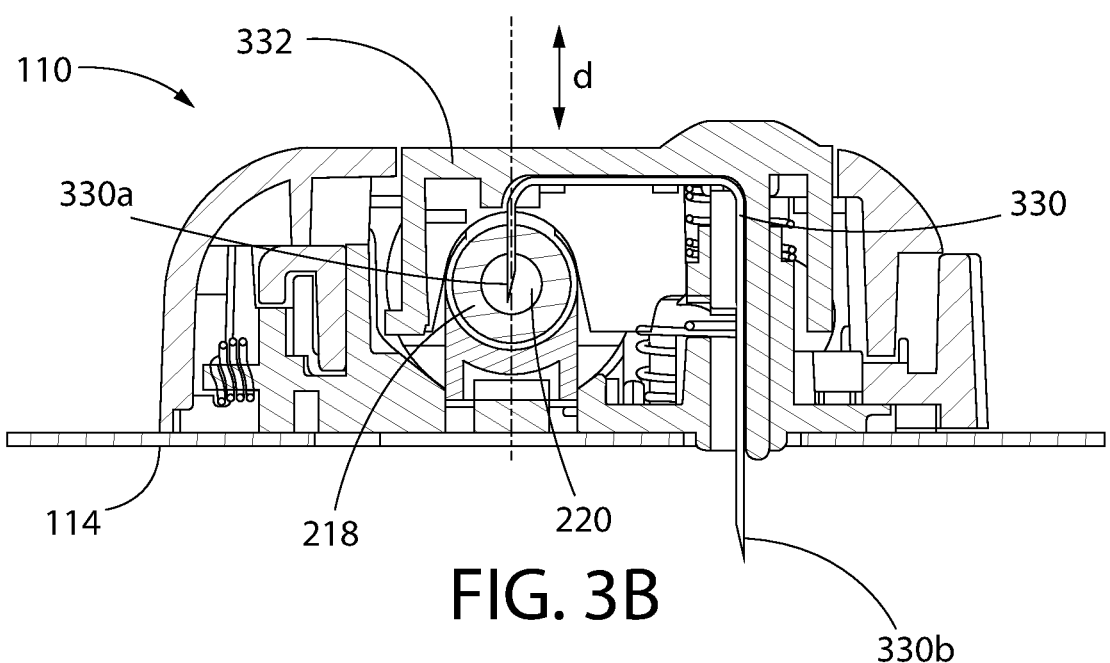
FIG. 3B is a front cross sectional view of the fluid delivery device of FIG. 3A shown in the deployed position.

Referring to FIGS. 3A and 3B, a needle 330 may be deployed to fluidly couple fluid reservoir 220 and the patient. Needle 330 may be coupled to a button 332 and the needle 330 may be bent such that a translation of button 332 toward the patient causes a fluid coupling end 330a to be fluidly coupled to fluid reservoir 220 and a delivery end 330b to extend from bottom surface 114.

Liquid pharmaceuticals for subcutaneous delivery medicaments are commonly packaged in cartridges or vials having a fluid reservoir. These cartridges that are filled prior to coupling with a fluid deliver device may be referred to as prefilled cartridges or prefilled reservoirs. In some embodiments, it is desirable to be able to load these prefilled cartridges or cartridge assemblies into a fluid delivery device for ease of handling rather than have to fill a reservoir already inside of the device.

A cartridge is normally a cylinder reservoir with a septum seal on one end and a piston or plunger inside at an opposite end. The medicament is delivered by fluidly connecting the material inside of the cartridge reservoir through the septum with the patient's body and then pressing on the piston to move the piston along the axis. Due to manufacturing preferences, the septum may be a planar element at the end of the cartridge. Also, in a skin secured device, it is desirable to minimize the height of the device, therefore the extended axis of the cartridge is usually positioned substantially parallel to the base of the device. The result is that the flat septum lies in a plane generally perpendicular to the surface of the skin.

Making a fluidic connection between the reservoir and the patient's skin requires elements of the fluidic path to move in essentially perpendicular directions; parallel to the axis of the reservoir and perpendicular to the patients skin. In one embodiment, the fluidic path is moved in a first direction to penetrate the cartridge septum and a second to penetrate the skin of the user. In other embodiments, the fluidic path penetrates the cartridge septum and the user's skin simultaneously or the fluidic path first penetrates the skin of the user before penetrating the cartridge septum.

A device that contains a needle may also control the potential for the needle to be exposed when it is not supposed to be deployed to minimize the chance for an unintended needle stick or contamination. This control may function before and after the device's use.

Embodiments of the present invention may allow for making a liquid connection between a septum sealed container within a device positioned on the skin and the subcutaneous region of the skin without the manual manipulation of a needle, syringe or infusion set. Such embodiments may allow a needle to connect a container of liquid with a flat septum seal substantially perpendicular to the skin with the subcutaneous region of the skin by the user pressing a button or other simple actuation. In some embodiments, the needle is not straight. In some embodiments, the needles are moved in multiple directions to both penetrate the septum seal and the user's skin by a single actuation of the user (e.g., pressing a button).

It is therefore desired to have a simple to use mechanism that allows a single user operation connection between a liquid vessel with a flat septum perpendicular to the skin and subcutaneous skin levels. The mechanism may place one end of a small diameter needle (e.g., a 25 gage or smaller) into the skin and create a liquid path with a previously sealed vial through a septum seal where the vial is in its final position relative to the skin. The system may also be able to be triggered to retract the needle from the skin once the user desires to remove the device such as when the infusion is complete.

Embodiments herein may address the need for a mechanism that is simple to operate and can make the required liquid connection from a septum seal perpendicular to the surface of the skin and the users subcutaneous skin with a continuous needle. The embodiments may also include a needle assembly mounted to a door or a cover for the housing.

The fluid delivery system or device according to embodiments of the present invention may exist in three states: an initial state where the needle is not in fluid communication with the fluid reservoir, a primed state where the needle is in fluid communication with the fluid reservoir but the needle is not deployed into the user's tissue, and a deployed state where the needle is in the skin and is in fluid communication from the inside of the fluid reservoir to the tissue of the user. The needle may be moved from the initial state to the primed state to the deployed state and, in some embodiments, back to the primed state. In alternative embodiments, the needle may be deployed into the user's tissue prior to or simultaneously with the fluid connection being made between the needle and the fluid reservoir. Following use, the needle may be retracted and retained in the housing to prevent further use.

With the cartridge in place in the fluid delivery device, according to some embodiments, the delivery device is in its initial state. Closing a latch such as a door may force the fluid coupling end of the needle through the fluid reservoir septum and the device is in its primed state. By pressing the button on the device, the distal delivery end of the needle is moved into the user's tissue and latches and the device is in its deployed state. Releasing the latch and allowing the needle's delivery end to leave the tissue returns the device to its primed or initial state.

Embodiments of the delivery needles disclosed herein may be used with various fluid delivery devices such as the fluid delivery devices disclosed in U.S. Patent Application Publication No. 2013/0046239, U.S. Patent Application Publication No. 2011/0306929, and U.S. Pat. No. 7,481,792 that are hereby incorporated by reference in their entirety. The cartridges and other components of these fluid delivery devices may be modified to accommodate the various needle assemblies disclosed herein.

In some embodiments, the fluid delivery device includes a housing and a bottom surface configured to be coupled to a skin surface in an engaged position. In one embodiment, a cartridge having a fluid reservoir is coupled to the housing and has a septum. In one embodiment, the septum seals one end of the fluid reservoir and a piston seals the other end. The patient may insert a pre-filled cartridge assembly into the fluid delivery device prior to use. The septum of the cartridge may have a pierceable portion, the portion of the septum pierced by the needle during use. In one embodiment, the cartridge is comprised of glass, or has an inner glass coating, though other materials for the cartridge such as plastic may be used.

In some embodiments, a needle assembly having a needle or needles may be used to fluidly couple the septum with the skin surface with the desired motion by the user or be configured to automatically deploy upon use of the device. The needle may have a delivery end and a fluid coupling end. Initially, the fluid coupling end may be fluidly disengaged from the fluid reservoir, (e.g., an initial or pre-fluid delivery position). The delivery end of the needle may also be spaced above the bottom surface of the fluid delivery device such that both ends of needle are contained within the cartridge assembly in the initial position. After the cartridge assembly is inserted into the fluid delivery device and the device is adhered to the skin surface, the fluid coupling end of the needle may be extended through the pierceable portion of the septum and the delivery end of the needle may be extended through the bottom surface of the fluid delivery device either simultaneously, at offset times or separately such that fluid reservoir is fluidly coupled with the patient during use (e.g., a deployed, in-use or fluid delivery position). After use, the needle may be retracted back into the housing and prevented from further deployment.

In some embodiments, where the system is driven by a hydraulic fluid, the hydraulic fluid must be contained securely in the device prior to the cartridge being installed. Once installed, the fluid or fluid driven element is operable to push the cartridge piston with minimal and preferably no compressible volume between the two.

Figure 4:
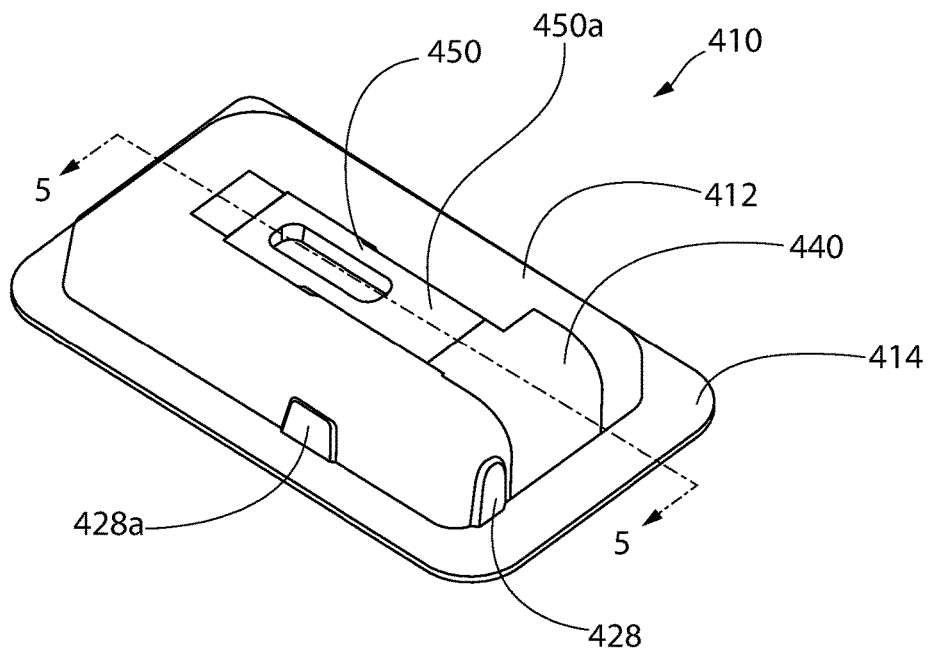
FIG. 4 is a trimetric view of a fluid delivery device in accordance with an exemplary embodiment of the present invention.
Figure 5:
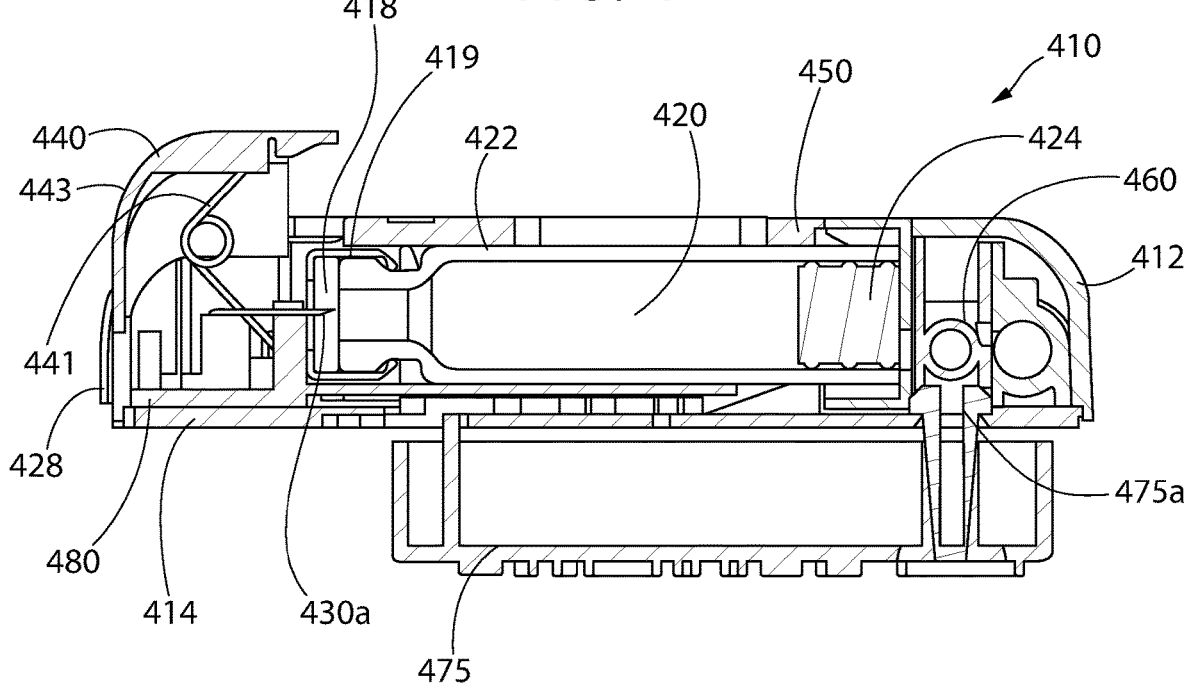
FIG. 5 is a side cross sectional view of the fluid delivery device of FIG. 4 taken along a plane indicated by line 5-5.

Referring to FIGS. 4-5, an exemplary the fluid delivery device 410 is shown that includes a housing 412 having an insertable prefilled cartridge assembly 450. The fluid delivery device 410 may include an adhesive bottom surface 414 such as a foam pad to attach the fluid delivery device 410 to the skin of the patient. The fluid delivery device 410 may include one or more actuators (such as an internal basal actuator and/or a bolus actuator 428) that act on the piston 424 within cartridge assembly 450. In one embodiment, the one or more actuators drive a hydraulic fluid that acts on the piston 424.

Figure 6A:
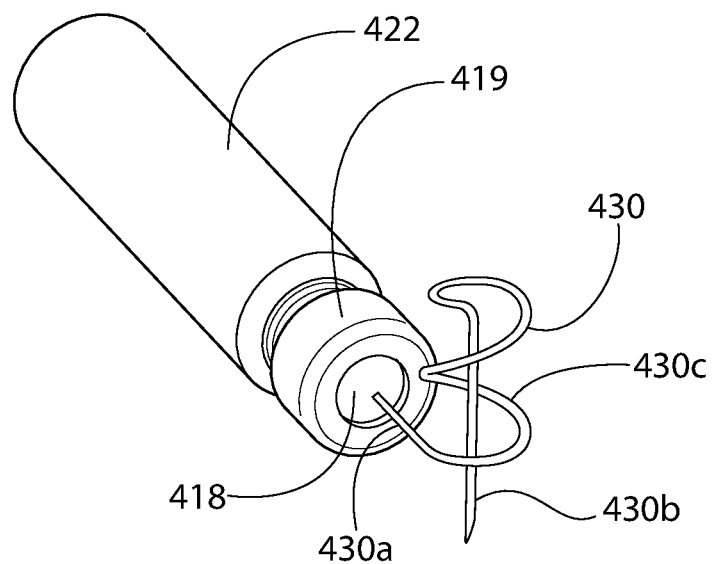
FIG. 6A is a trimetric view of a cartridge and a needle of the fluid delivery device shown in FIG. 4.
Figure 6B:
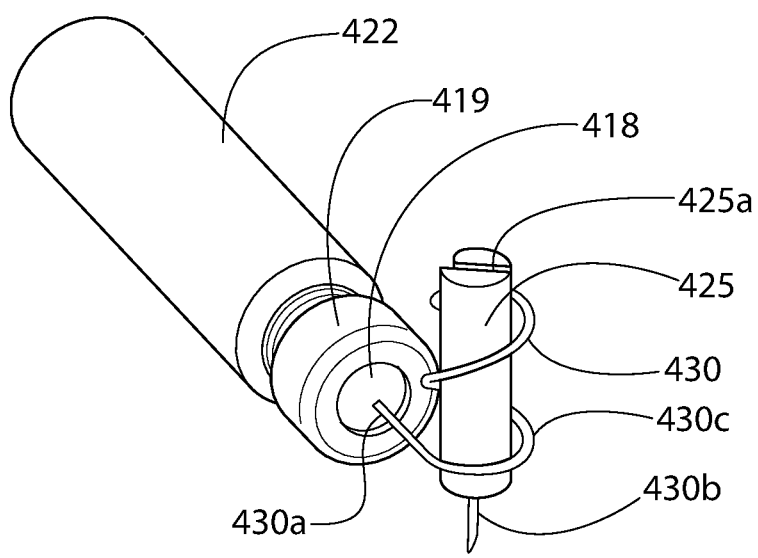
FIG. 6B is a trimetric view of the cartridge and the needle shown in FIG. 6A showing the needle coupled to a needle core.
Figure 6C:
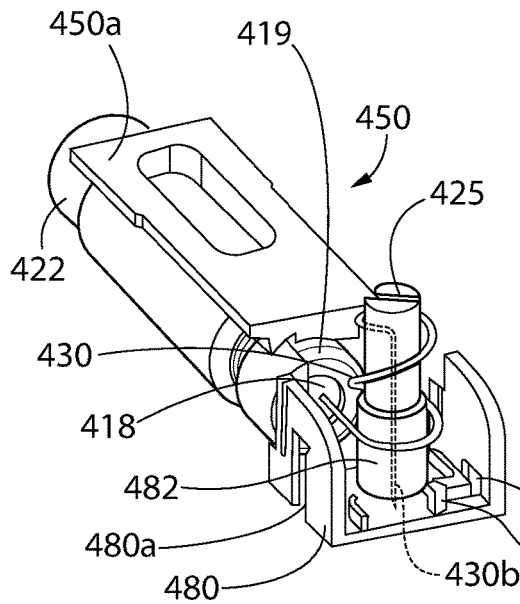
FIG. 6C is a trimetric view of the cartridge, needle and needle core shown in FIG. 6B along with a needle assembly base.
Figure 6D:
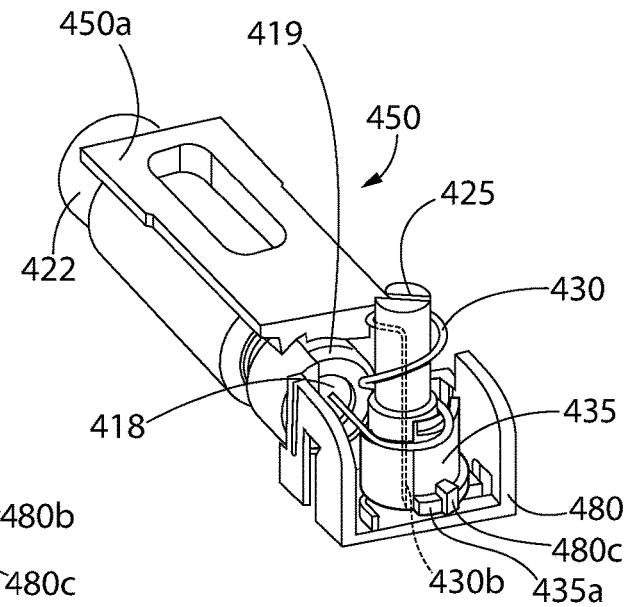
FIG. 6D is a trimetric view of the cartridge and needle assembly shown in FIG. 6C along with a lock member.
Figure 6E:
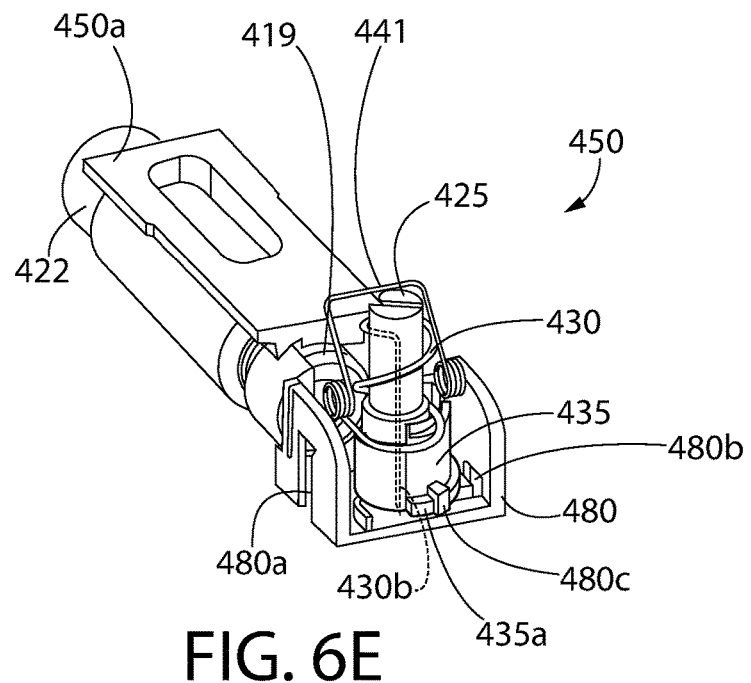
FIG. 6E is a trimetric view of the cartridge and needle assembly shown in FIG. 6D along with a button biasing member.

Referring to FIGS. 6C-6E, fluid delivery device 410 may have a cartridge assembly 450 that contains a cartridge 422 prefilled with a liquid before the cartridge assembly 450 is inserted into the fluid delivery device 410. In one embodiment, the cartridge assembly 450 includes a needle assembly 443 having a mechanism to manage the movement of the needle 430. The cartridge assembly 450 may be comprised of a number of components to position and control the motion of enclosed parts. The cartridge assembly 450 may be generally flush with the housing 412 in the deployed position (see FIG. 4). In one embodiment, the cartridge assembly 450 includes a panel 450a that forms part of the top of the fluid delivery device 410 in the deployed position.

Referring to FIG. 5, an exemplary embodiment of the inside of the fluid delivery device 410 is shown. The cartridge 422 may include a fluid reservoir 420, a piston 424 slideable within the fluid reservoir 420 and a pierceable septum 418. In one embodiment, a crimp cap 419 seals the septum 418 to the end of the cartridge 422. As discussed in further detail below, the needle 430 may be configured so that the fluid coupling end 430a can penetrate the septum 418 through the motion of the needle 430 generally along the axis of the cartridge 422 and the delivery end 430b (see FIG. 6A) can penetrate the skin of the patient through the compression of a flexible coiled central portion 430c of the needle 430 allowing the fluid delivery end 430b of the needle 430 to move along its axis into the skin without displacing the fluid coupling end 430a of the needle 430.

Referring to FIG. 6B, the needle 430 may be secured within a needle core 425 proximal to the fluid delivery end 430b of the needle 430 but distal to the central portion 430c. The needle core 425 may be generally cylindrical in shape. In other embodiments, the needle core 425 is rectangular or has cross or triangular cross sectional shape. In one embodiment, the needle 430 from the fluid delivery end 430b extends up through the center of the needle core 425 and then wraps around and down the outside of the needle core 425 toward the fluid coupling end 430a of the needle 430. In one embodiment, the central portion 430c of the needle 430 has a flexible serpentine or helically shaped form in the initial position. The needle 430a may be secured to the needle core 425 such that at least the depth the needle 430 has to penetrate the tissue extends distally out of the needle core 425. In one embodiment, the distance the fluid delivery end 430a of the needle 430 extends from the needle core 425 is between approximately 1 mm and approximately 15 mm. The needle 430 may be secured to the needle core 425 by ultrasonic welding, heat staking, adhesive, an interference fit, one or more snap fits, or a combination of these. In one embodiment, the needle core 425 is hollow except for a region at the proximal or top end for securing the needle 430 to allow the fluid delivery end 430b to freely flex or float relative to the fluid delivery device 410. In one embodiment, the needle core 425 includes a grove 425a that the needle 430 extends through. In one embodiment, the needle core 425 is joined to the button 440 creating the needle assembly 443 comprising of the needle 430, the needle core 425 and the button 440.

Referring to FIG. 6C, the cartridge assembly may include an assembly body 480 that supports the needle core 425 and the cartridge 422. The assembly body 480 may include a boss 482 that receives and guides the needle core 425. In one embodiment, the needle core 425 slides within the boss 482. The fluid coupling end 430a of the needle 430 may extend from the septum 418 a sufficient distance such that moving the needle assembly 443 (see FIG. 9C) toward the cartridge 422 extends the fluid coupling end 430a of the needle 430 into the fluid reservoir 420. In one embodiment, the distance the needle 430 may be moved toward and through the septum 418 in the initial position is between approximately 1 and approximately 15 mm. The needle 430 close to the fluid coupling end 430a may be secured to the assembly body 480, such as to the boss 482, to maintain the position of the fluid coupling end 430a relative to the axis of the cartridge 422. In one embodiment, the needle 430 is attached to the assembly body 480 by ultrasonic welding, heat staking, extending through a feature such as an aperture, an interference fit or by an adhesive.

In one embodiment, the needle core 425 is configured to slide within the boss 482 such that the delivery end 430b of the needle 430 is retained within the needle assembly 443 in the initial position and extends from the bottom of the assembly body 480 in the deployed position. In one embodiment, the boss 482 is a round cylindrical tube with an inside diameter matched to the outside diameter of needle core 425. The boss 482 may be integral with the assembly body 480. In other embodiments, the boss 482 is attached to the assembly body 480.

Referring to FIGS. 6D and 6E, the cartridge assembly 450 may include a lock member 435. The lock member 435 may be rotatably coupled to the boss 482. In one embodiment, the lock member 435 has an inside diameter with a slip fit around the outside diameter of the boss 482. The lock member 435 may extend from the bottom of the assembly body 480 to the fluid coupling end 430a and the bottom loop of the needle 430. The lock member 435 is configured to rotate about the boss 482 to lock or allow actuation of the needle 430 depending on the angular position of the lock member 435 about the boss 482. The lock member 435 may be retained axially in place by a retention member 480c such as a hook that extends over and engages a bottom lip 435a of the lock member 435.

Figure 7:
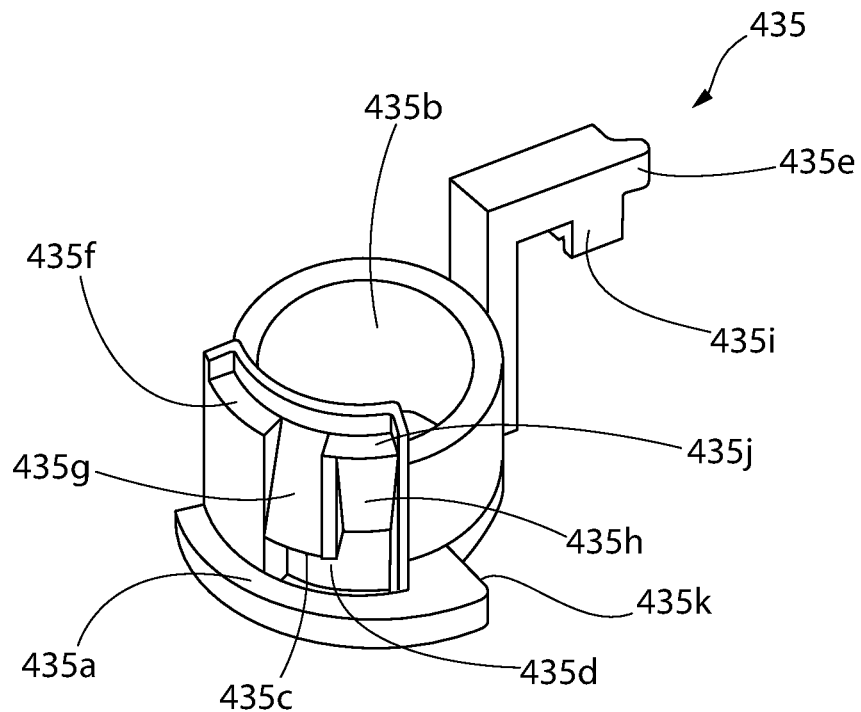
FIG. 7 is a trimetric view of the lock member shown in FIGS. 6D and 6E.

Referring to FIG. 7, the lock member 435 may include one more features to control and limit the motion of the needle 430. The lock member 435 may include an opening 435b that is configured to receive the boss 482. The lock member 435 may include one or more lips and ramps to control the vertical motion of the needle 430 relative to the assembly body 480. In one embodiment, the lock member 435 includes a first top lip 435f, a first ramp 435g, a bottom lip 435c, a transition space 435d, a second ramp 435h and a second top lip 435j. In one embodiment, the lock member 435 is configured such that latch 440a, discussed further below, is retained on the first top lip 435f in the initial position, slides down first ramp 435g during deployment, latches onto bottom lip 435c during use, slides through transition space 435d and up second ramp 435h during retraction and is retained on the second top lip 435j in the final locked out position.

The lock member 435 may include one or more features that control the rotational position of the lock member 435 relative to the boss 482. In one embodiment, the lock member 435 includes a pivot arm 435e. In one embodiment, the pivot arm 435e is diametrically opposed from lip and ramp features. The pivot arm 435e may include a stop member 435i.

Figure 8:
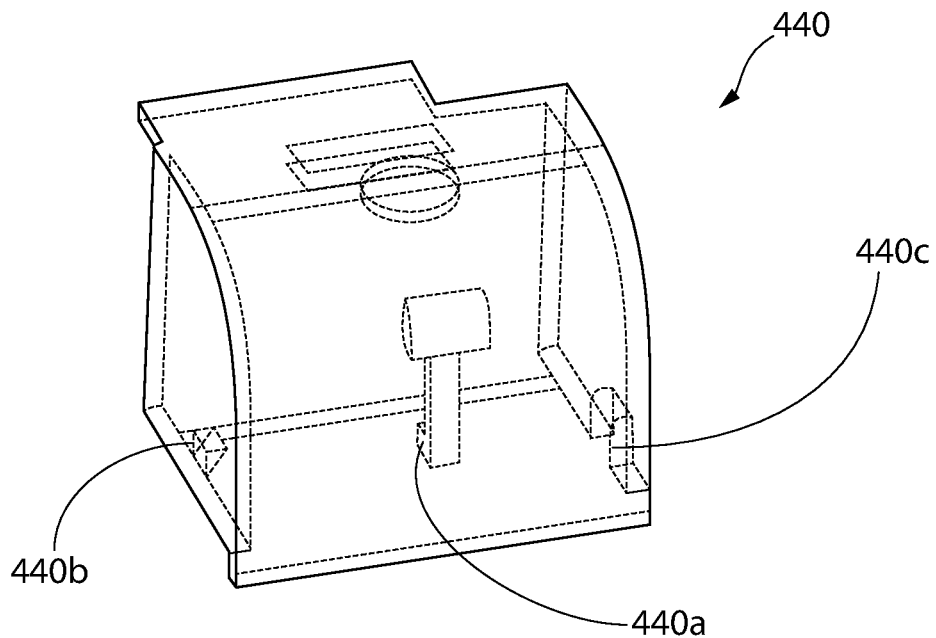
FIG. 8 is a partially transparent trimetric view of the needle button of the fluid delivery device shown in FIG. 4.

Referring to FIG. 8, the needle assembly 435 may include a button 440. The button 440 may be coupled to the needle core 425 to move the needle core 425 and the needle 430 relative to the assembly body 480 and the lock member 435. The button 440 may be secured to the needle core 425 by ultrasonic welding, heat staking, an adhesive or by an interference fit. The button 440 and the assembly body 480 may form a housing for the needle assembly 443. The button 440 may include the latch 440a. The latch 440a may extend toward the open center of the button 440. The latch 440a may include a flexible arm. In one embodiment, the latch 440a can flex toward and away from the center of the button 440 but the latch 440a cannot stretch or be compressed lengthwise. In one embodiment, the latch 440a is biased to flex towards and away from the lock member 435 verses side to side by being significantly larger in the side to side dimension than in the dimension to and from the lock member 435. The button may include one or more tabs 440b that extend toward the open center of the button 440. The button 440 may include a hole or notch 440c. In one embodiment, the tab 440b and the notch 440c are on opposing ends of the button 440 and the latch 440a is on a side of the button 440.

Referring to FIG. 6E, a biasing member 441 may be coupled between the assembly body 480 and the button 440 to bias the button 440 and the needle assembly 443 away from the assembly body 480. In one embodiment, the biasing member 441 is a torsion spring. In other embodiments, the biasing member 441 is a coil spring. The button 440 may include one or more features such a tab 440b that engage with the assembly body 480 such as groove 480a (see FIG. 6E) to help guide the motion of the button 440 relative to the assembly body 480 and prevent the button 440 from traveling too far away from the assembly body 480.

In one embodiment, the position of the needle assembly 443 relative to the cartridge 422 is controlled by the position of the lock member 435. In one embodiment, the position of the lock member 435 is controlled by the status of the insertion of the cartridge assembly 450 into the fluid delivery device 410.

Referring to FIGS. 7 and 8, in the initial state the first top lip 435f may block the latch 440a from going down and thus prevents the attached needle 430 from being deployed. In one embodiment, in this initial state, the pivot arm 435e is positioned to block the relative motion between the assembly body 480 and cartridge 422 thus preventing the fluid coupling end 430a of the needle 430 from penetrating the reservoir septum 418. In one embodiment, the pivot arm 435e includes a stop 435i that hooks over the back of the assembly body 480 to reinforce the blocking of the cartridge 422 motion.

In a second state, the lock member 435 has been rotated clockwise to a second position. In this second position, the lock member 435 is rotated clockwise a sufficient distance to move the pivot arm 435e away from the cartridge 422 so that the assembly body 480 and the cartridge 422 can be pushed together resulting in the fluid connecting end of the needle 430 penetrating the septum 418. This creates a fluid path from inside the fluid reservoir 420 through the needle 430 to the atmosphere. This temporary situation allows any pressure that may have built up in the fluid reservoir 420 to escape without delivering a sudden excess dose to the patient. The first top lip 435f extends far enough around the lock member 435 so that in this second state the first top lip 435f still blocks the latch 440a and thus the needle assembly 443 from going down and thus prevents the needle 430 from being deployed.

In a third state, the lock member 435 has been rotated clockwise to a third position. In this third position, the lock member 435 may be rotated a sufficient distance to align the first ramp 435g with the latch 440a. In this position, pressing down on the top of the button 440 can move the needle assembly 443 down as the first top lip 435f is no longer blocking the latch 440a. As the needle 430, needle core 425 and button 440 move down, the latch 440a is flexed outward by the shape of the first ramp 435g. When fully depressed, the fluid delivery end 430b of the needle is deployed to the desired depth into the patient and the end of the latch 440a snaps under the bottom lip 435c. The bottom lip 435c retains the latch 440a and prevent button 440 from rising under the force of biasing member 41 thus retaining delivery end 430a of the needle 430 at the proper delivery depth during fluid delivery. The fluid connection between the cartridge 422 and the patient tissue is now complete and the controlled delivery of the medicament can begin.

Once the delivery of medicament is complete, the lock member 435 may be rotated clockwise to a fourth position resulting in a fourth state. In this fourth position, the lock member 435 may be rotated a sufficient distance to align the second ramp 435h with the latch 440a. As there is no longer a ledge retaining latch 440a, the needle assembly 443 can move under the force of the biasing member 441, flexing the latch 440a outward returning the needle 430 to its retracted position. In this final position, the latch 440a snaps back in and positions the latch 440a on the second top lip 435j. The second top lip 435j blocks latch 440a from going down preventing the needle 430 from being redeployed.

In one embodiment, the pressure to deploy the needle 430 is supplied by the user's finger. In another embodiment, the pressure to deploy the needle 430 is supplied by a biasing member that is part of the fluid delivery device 410. In one embodiment, the biasing member includes one or more torsion or coil springs. In one embodiment, the biasing member is comprised of one or more elastomeric or plastic components.

In one embodiment, the pressure to retract the needle 430 is supplied by a biasing member that is part of the fluid delivery device 410. In one embodiment, the biasing member consists of one of more torsion springs. In one embodiment, the biasing member consists of one or more coil springs inside of the central section 430c of the needle 430, positioned under the needle core 425 inside of the boss 482, or next to the boss 482. In one embodiment, the pressure to retract the needle 430 is supplied by needle's elastic deformation. In one embodiment the biasing member may be one of more elastomeric or plastic components. In one embodiment, the pressure to retract the needle 430 is supplied by removing the force applied by the biasing member or members that are used to deploy the needle 430.

Figure 9A:
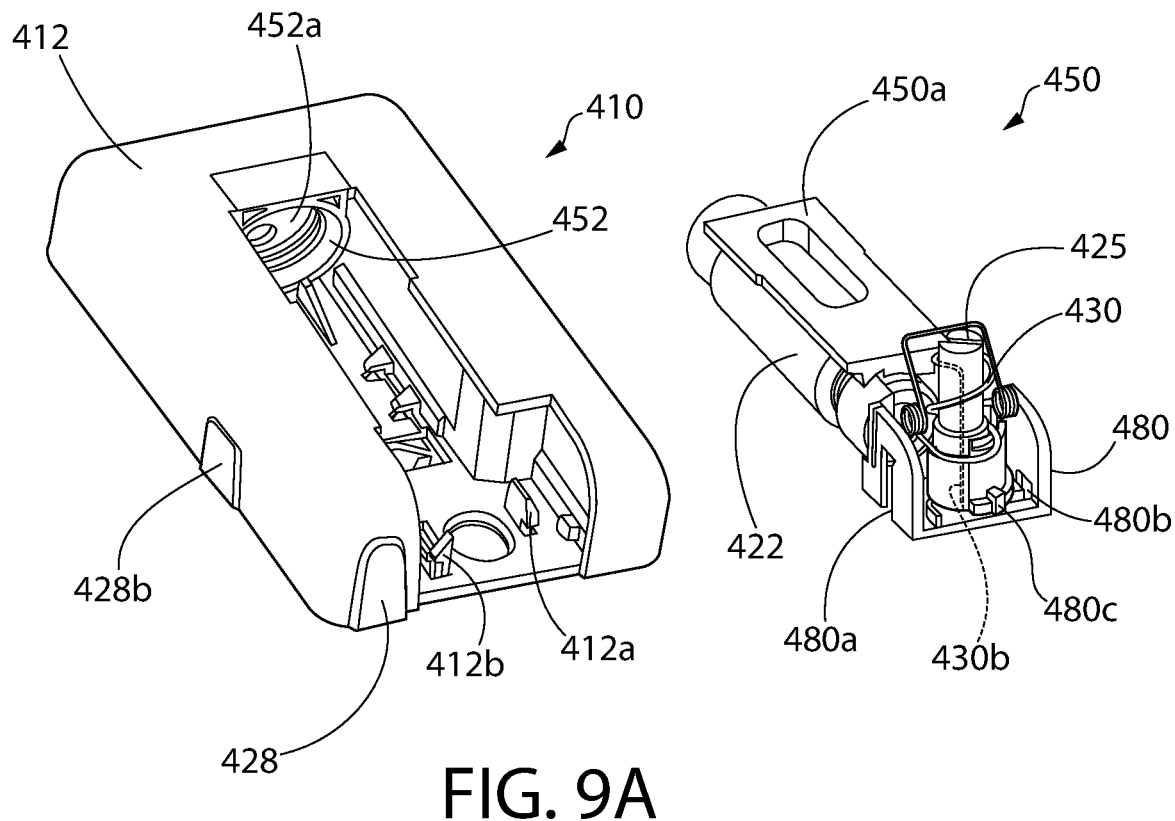
FIG. 9A is a trimetric view of the fluid delivery device of FIG. 4 showing the prefilled cartridge before being inserted into the housing.
Figure 9B:
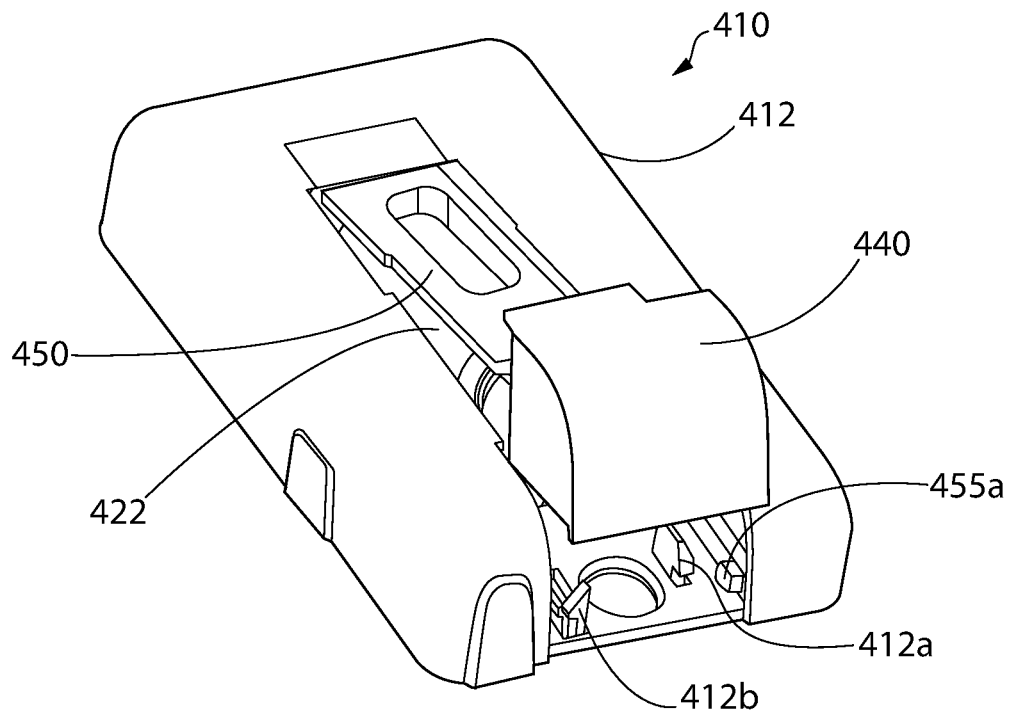
FIG. 9B is a trimetric view of the fluid delivery device of FIG. 4 showing the prefilled cartridge being inserted into the housing.
Figure 9C:
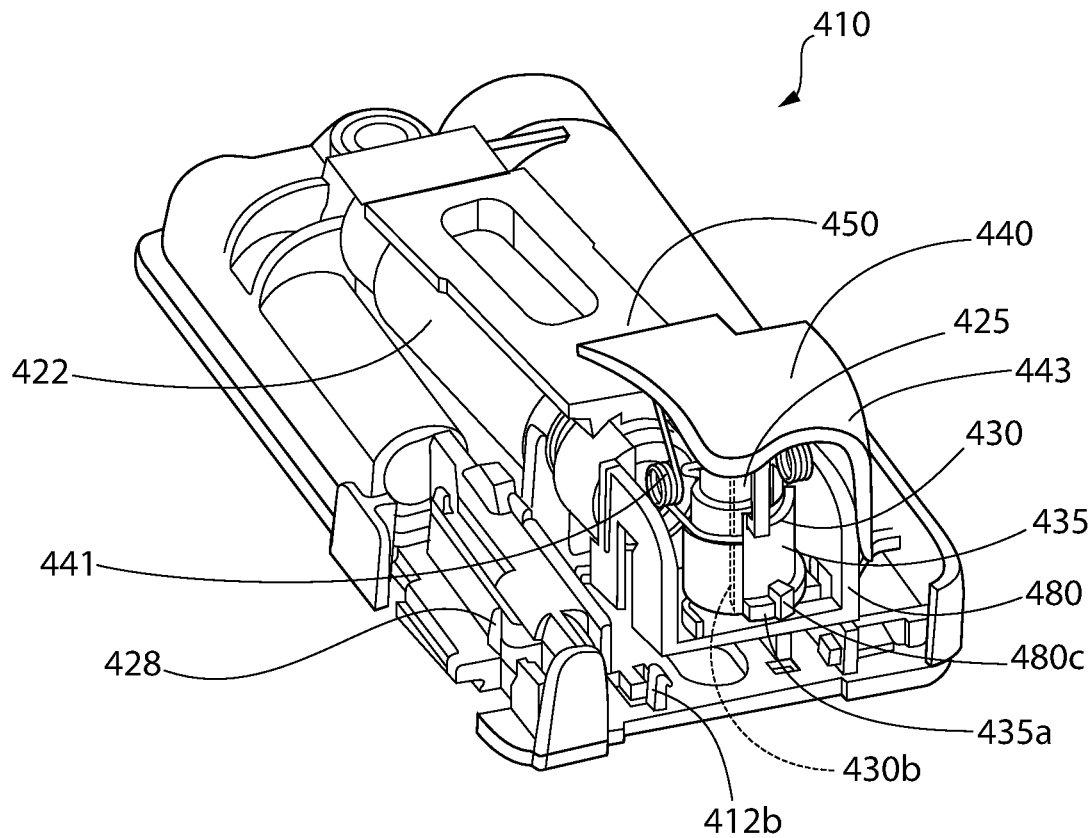
FIG. 9C is a trimetric view of the fluid delivery device of FIG. 9B with the housing and a portion of the needle button removed.

Referring to FIGS. 9B and 9C, in use, a user takes the cartridge assembly 450 having a cartridge 422 prefilled with a fluid and inserts the cartridge 422 into a mating sealing receptacle 452 in the fluid delivery device 410. In one embodiment, the cartridge 422 is inserted at an angle so that the needle assembly 443 clears the retaining members 412b in the housing. In one embodiment the cartridge 422 is initially separate from the remainder of the cartridge assembly 450, and the cartridge 422 is first inserted into the cartridge assembly 450 before inserting the cartridge assembly 450 into the housing 412.

Figure 9D:
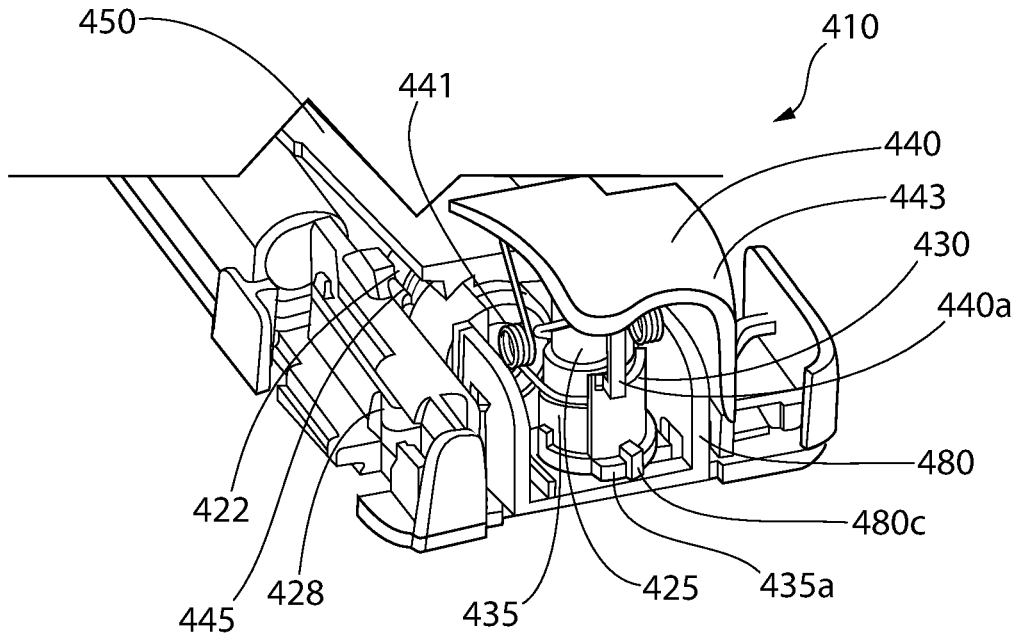
FIG. 9D is a trimetric view of the fluid delivery device of FIG. 9B showing the cartridge assembly fully inserted and the needle assembly in the initial position.

Referring to FIGS. 9B-9D, in use, the cartridge assembly 450 may be snapped down into the fluid delivery device 410 such that a retention clip 445 holds the fluid reservoir in position. The needle assembly 443 may be coupled to the fluid delivery device by one or more retaining members 412b that extend through and latch onto the assembly body 480. In one embodiment, a cam member 412a extends up through an opening in the assembly body 480 when the cartridge assembly 450 is snapped down into place. This cam member 412a has a profiled surface that engages with the end 435k of base lip 435a of the lock member 435 to rotate the lock member 435 clockwise and into the second position.

Figure 9E:
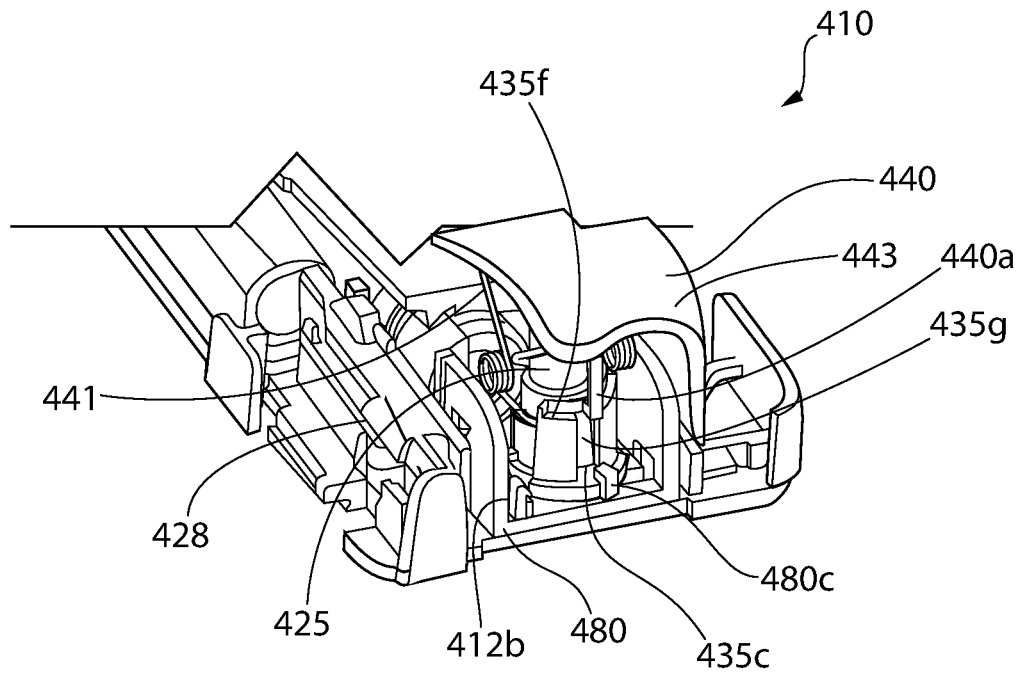
FIG. 9E is a trimetric view of the fluid delivery device of FIG. 9B showing the cartridge and needle assembly in the engaged position.

Referring to FIG. 9E, once the lock member 435 is in the second position and the pivot arm 435e is out of the way, the user may press the assembly body 480 along the axis of the cartridge 422 back into the fluid delivery device 410. This motion moves the fluid coupling end 430a of needle 430 into the fluid reservoir 420 fluidly coupling the needle 430 with the fluid reservoir 420. Pushing the assembly body 480 fully into the fluid delivery device 410 causes the cam member 412a to engage end 435k of the lock member 435 to further rotate the lock member 435 clockwise to the third position. In the third position, the one or more retaining members 412b engage with the assembly body 480 to retain the needle assembly 443 in place. Once the lock member 435 is in the third position, the device can be activated and secured to the user and deployed before loss of any significant volume of medicament due to the low basal flow rate.

Figure 10A:
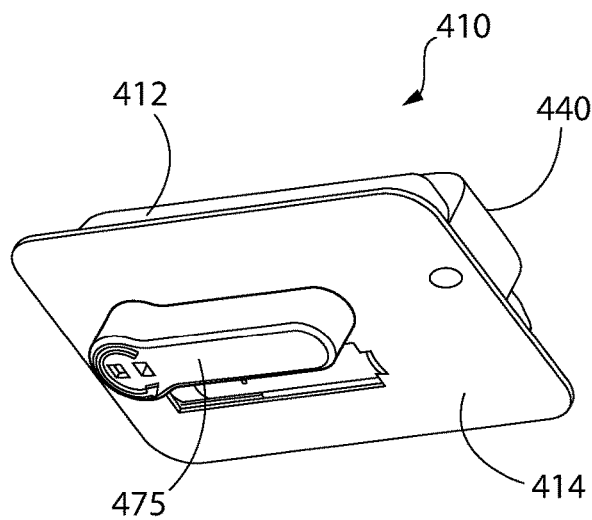
FIG. 10A is a bottom trimetric view of the fluid delivery device of FIG. 9B in the initial position.
Figure 10B:
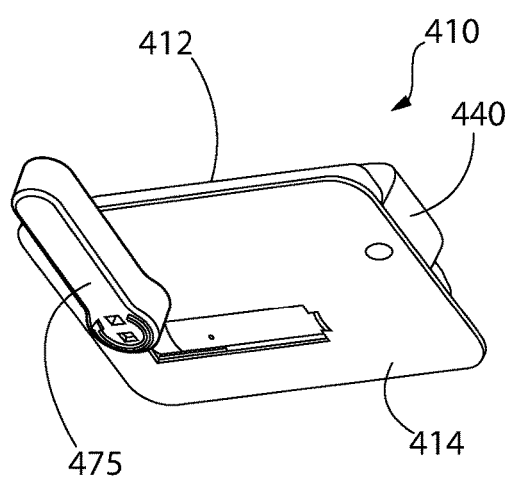
FIG. 10B is a bottom trimetric view of the fluid delivery device of FIG. 9B in the engaged position.

Referring to FIGS. 5, 10A and 10B, in one embodiment, the fluid delivery device 410 is hydraulically driven with a viscous hydraulic liquid pressing on the proximal side of the plunger 424 within the cartridge 422 to push the medicament through the fluid path where the hydraulic fluid is contained by a valve 460. In one embodiment, the valve 460 is similar to the valve 3060 as shown and described in FIG. 30G. In one embodiment, the valve 460 is similar to the valve 3160 as shown and described in FIG. 31J. In one embodiment, once at least in the second position and preferably in the third position, the valve 460 between the stored hydraulic liquid and the inside of the reservoir 420 can be opened. In one embodiment, the valve 460 is a rotary valve coupled to a lever 475 that extends outside of the housing 412. The valve 460 may be opened by the user turning the lever 475 a sufficient rotational distance such as 90°.

The lever 475 may be releasably coupled to the valve 460 by a pair of radially deformable prongs 475a (see FIG. 5). In one embodiment, rotation of the lever 475 aligns the prongs 475a with an aperture that allows the prongs 475a to be pulled out and released from the housing 412. In one embodiment, the lever 475 is prevented from being moved before the cartridge assembly 450 is inserted. In one embodiment, the lever 475 is prevented from being removed before it is turned sufficiently by a keyed opening in the fluid delivery device 410 that only lines up with the shape of the lever 475 in a position where the valve 460 is open. In one embodiment, the lever 475 extends out of the base of the fluid delivery device 410. In another embodiment, the lever 475 extends out of the top of the fluid delivery device 410. In another embodiment the lever 475 extends out of the top of the fluid delivery device 410 and extends to near the end of the fluid delivery device such that it interferes with the button 440 of the cartridge assembly 450 preventing the button 440 from being depressed until the lever 475 is removed. In one embodiment the lever 475 is prevented from being removed before a basal actuator 226 has been activated. In one embodiment rotating the lever 475 activates a basal actuator 226.

Figure 9F:
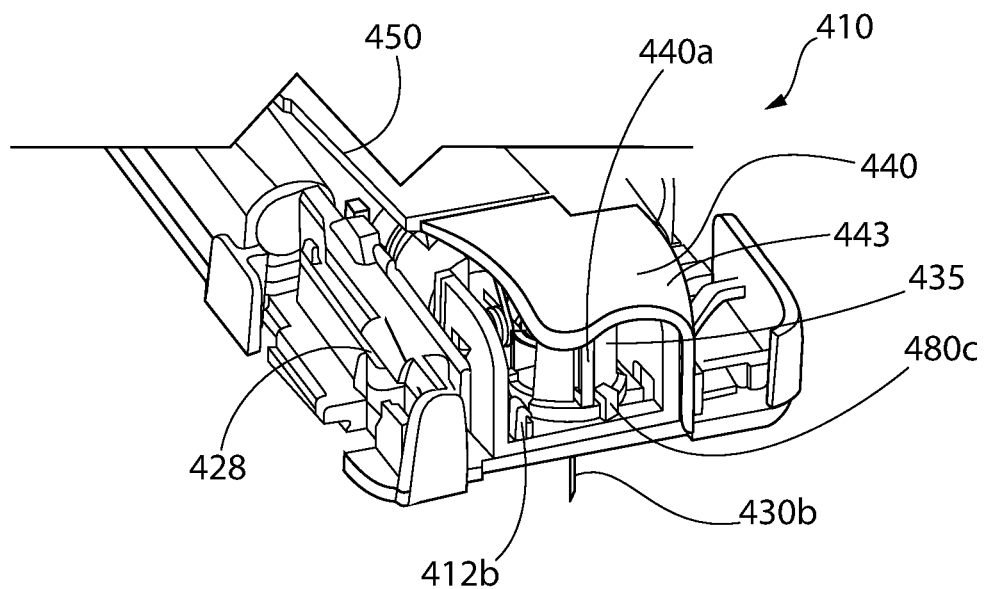
FIG. 9F is a trimetric view of the fluid delivery device of FIG. 9B showing the needle assembly in the deployed and locked position.

Referring to FIG. 9F, once the lock member 435 is in the third position, the latch 440a is no longer blocked by the first top lip 435f. In the third position, the button 440 and needle 430 can be depressed deploying the delivery end 430b of the needle 430 from the bottom of the fluid delivery device 410 and into the patient as described previously so the medicament can be delivered through the needle 430 until the user is ready to retract the needle 430.

Figure 9G:
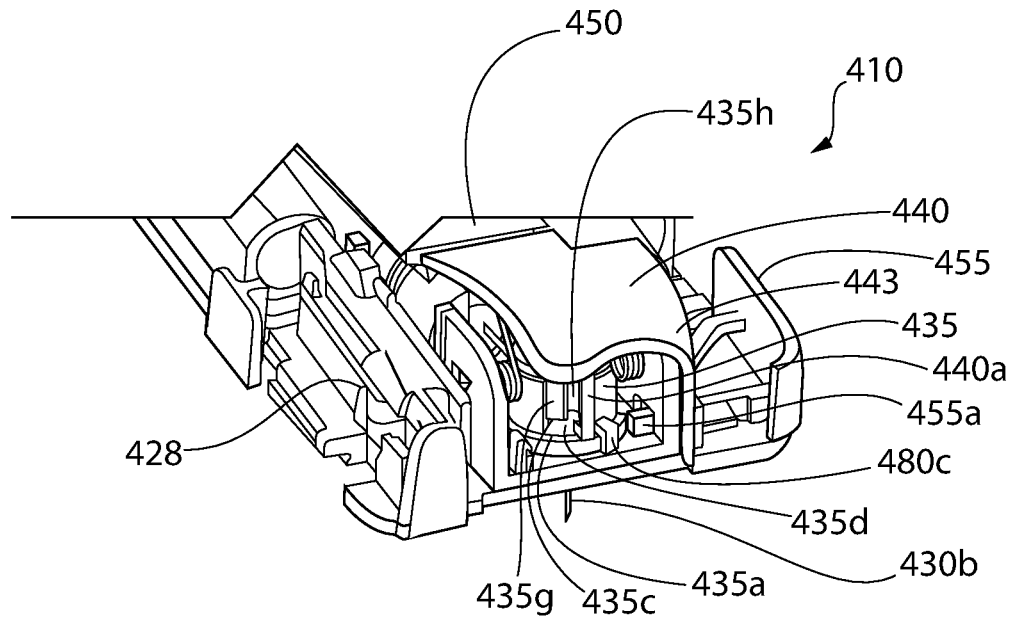
FIG. 9G is a trimetric view of the fluid delivery device of FIG. 9B showing the needle assembly in the deployed and released position.
Figure 9H:
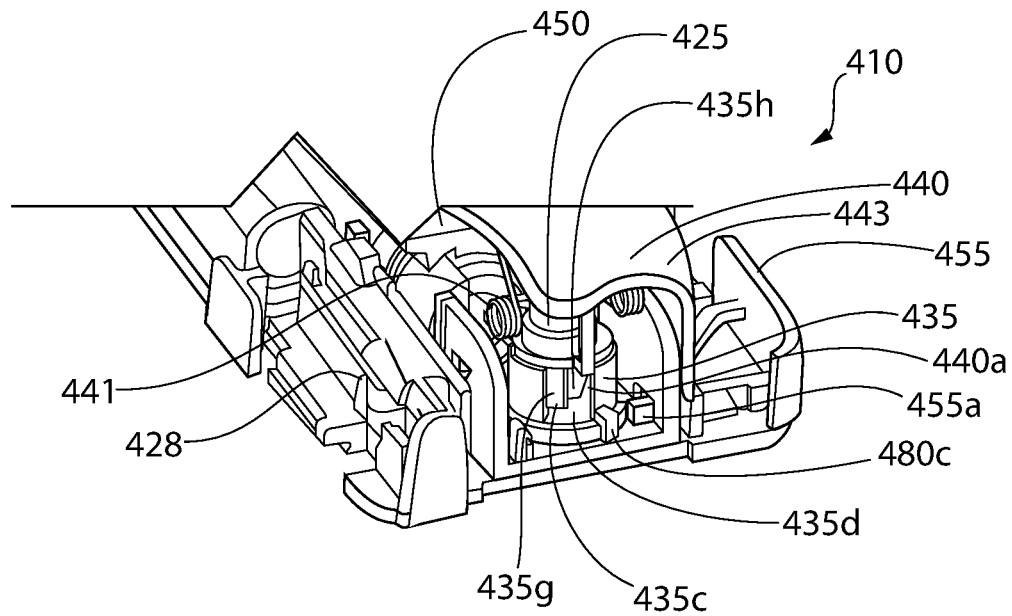
FIG. 9H is a trimetric view of the fluid delivery device of FIG. 9B showing the needle assembly in the disengaged and locked position.

Referring to FIGS. 9G and 9H, once the medicament has been delivered, the user may actuate the needle release button 455. A protrusion 455a extending from the needle release button 455 may extend through an opening 440c (see FIG. 8) in the assembly body 480 proximate the lock member 435. Pressing the needle release button 455 may cause the protrusion 455a to contact the end 435k of the base lip 435a of the lock member 435 to rotate the lock member 435 clockwise and into the fourth position. As the lock member rotates from the third position to the fourth position, the latch 440a travels along the transition space 435d of the lock member 435 to the second ramp 435h. When the latch 440a is aligned with the second ramp 435h, the latch 440a is no longer axially retrained by the bottom lip 435c and the biasing member 441 causes the needle 430 and button 440 to move upwardly relative to the assembly body 480. As the latch 440a slides up the second ramp 435h, the latch 440a is biased outwardly until it passes the second top lip 435j (see FIG. 7) and then the latch 440a springs back inwardly and engages the second top lip 435j preventing the needle 430 from being redeployed. In another embodiment, the protrusion 455a may not extend into the assembly body 480 but presses on a flexible portion of the assembly body 480 that then contacts the base lip 435a of the lock member 435 to rotate the lock member 435 clockwise and into the fourth position.

In an alternate embodiment, a protrusion from the depressed needle release button 455 extends under a portion of the needle 430, the needle core 425 and/or the button 440 after it retracts to block the needle 430 from being redeployed.

Figure 11:
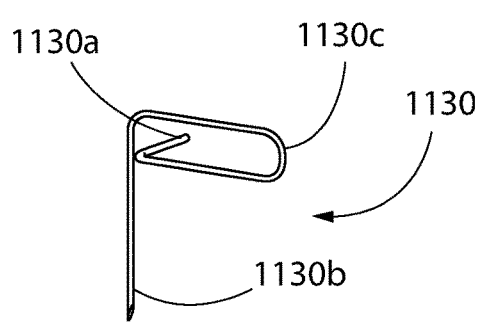
FIG. 11 is a trimetric view of a needle in accordance with an exemplary embodiment of the present invention.

Referring to FIG. 11, another exemplary embodiment of the needle 1130 is shown. The needle 1130 is similar to needle 430 discussed above except that the center section 1130c of needle 1130 bends about an axis parallel with the fluid coupling end 1130a of the needle 1130. The center section 1130c allows the delivery end 1130b of the needle 1130 to be deployed in and out of tissue generally linearly. The center section 1130c distributes strain in the needle 1130c allowing the translation of the needle 1130 with less force to keep the travel linear.

In one embodiment, the fluid coupling end 1130a of the needle 1130 does not rotate when the delivery end 1130b is deployed into or retracted from the user's tissue.

In one embodiment, the center section 1130c is substantially in a plane coplanar with delivery end 1130b of the needle 1130. In one embodiment, the center section 1130c is substantially in a plane generally normal to the fluid coupling end 1130a of the needle 1130. In one embodiment, the center section 1130c of the needle 1130 is essentially in a plane that is not normal to the fluid coupling end 1130a of the needle 1130 or parallel to the delivery end 1130b of the needle 1130. In one embodiment, the center section 1130c is not in a single plane.

Figure 12:
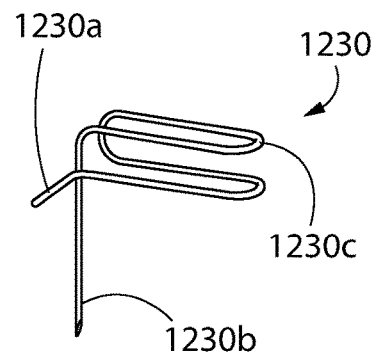
FIG. 12 is a trimetric view of a needle in accordance with an exemplary embodiment of the present invention.

Referring to FIG. 12, there is shown another exemplary embodiment of the needle 1230. The needle 1230 is similar to the needle 1130 discussed above except that the length of the center section 1230c is extended further through additional bends in the needle 810. Such additional bends in the needle 1230 may allow even more length to distribute the strain and lower bending forces on the center section 1230c as the delivery end 1230b is deployed along a generally linear path.

In one embodiment, by aligning the axes of curvature of the bends in the center section 1230c, fabrication is simplified as a single linear form and reduced steps are necessary to make the additional bends in the needle 1230.

Figure 13A:
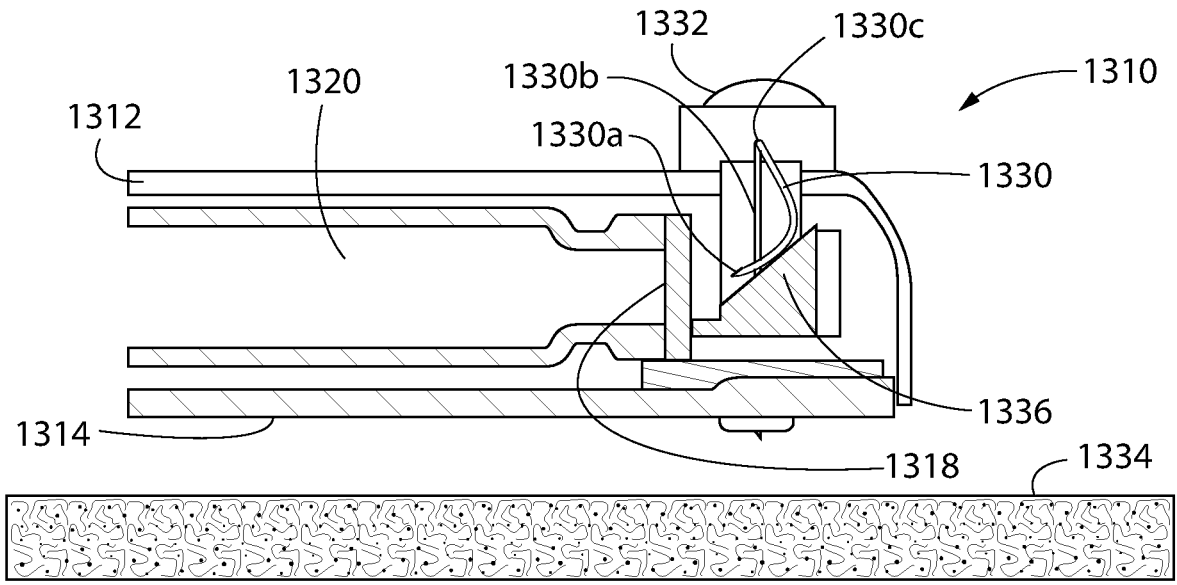
FIG. 13A is a side cross sectional view of a fluid delivery device in accordance with an exemplary embodiment of the present invention.
Figure 13B:
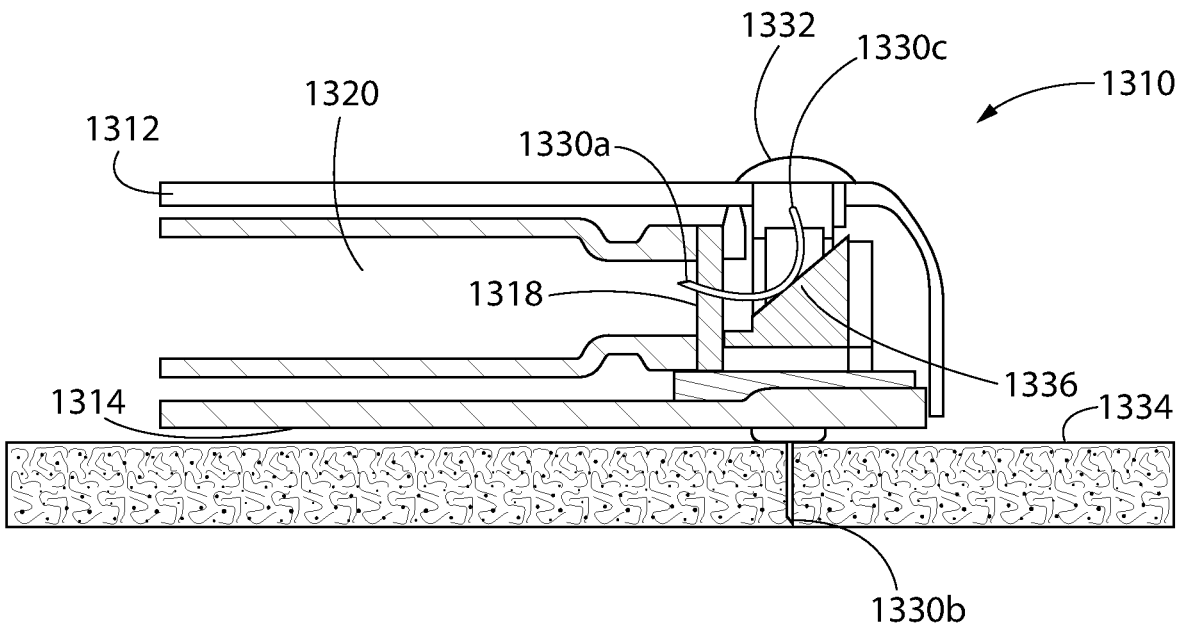
FIG. 13B is a side cross sectional view of the fluid delivery device of FIG. 13A shown in a deployed position.

Referring to FIGS. 13A and 13B, another exemplary embodiment of a fluid delivery device 1310 is shown.

In one embodiment, needle 1330 has a three dimensional curved shape. In one embodiment, needle 1330 is bent in at least two planes, and needle 1330 is straight in at least one of the at least two planes. In one embodiment, delivery end 1330b of needle 1330 is generally straight and generally perpendicular to bottom surface 1314 of fluid delivery device 1310. In one embodiment, at the top end of the delivery end 1330b, needle 1330 bends and a transverse section 1330c travels under button 1332. In one embodiment, once needle 1330 reaches an approximate centerline of fluid reservoir 1320, fluid coupling end 1330a of needle 1330 bends to be generally perpendicular with delivery end 1330b and then follows a curved path into the septum 1318. In one embodiment, the curve in delivery end 1330b is a non-uniform radius curve.

In one embodiment, extending delivery end 1330b of needle 1330 from bottom surface 1314 in the deployed position forces a portion of needle 1330 close to the fluid coupling end 1330a of needle 1330 (the curved portion) against a surface 1336 to direct fluid coupling end 1330a of needle 1330 into the fluid reservoir 1320.

In one exemplary use, when actuated by pressing button 1332, delivery end 1330b transverses linearly into skin 1334. Simultaneously, fluid coupling end 1330a of needle 1330 travels against ramp form surface 1336 and deforms transverse section 1330c, predominantly through twisting deformation, resulting in fluid coupling end 1330a of needle 1330 penetrating septum 1318 and making a fluid connection with fluid reservoir 1320. A catch mechanism may be used to hold button 1332 in place and needle 1330 in the deployed position for the duration of use (FIG. 13B).

Once finished, the catch on button 1332 may be released and a return spring (not shown) may be used to urge button 1332 and needle 1330 to their original position (FIG. 13A). In addition or alternatively, once the catch releases button 1332, the torsional spring tension in transverse section 1330c may cause needle 1330 to return to its original shape and rotate fluid coupling end 1330a back out of fluid reservoir 1320 allowing fluid coupling end 1330a to travel up surface 1336 and return needle 1330 to its original position.

Referring to FIG. 14A-14B, another exemplary embodiment of a fluid delivery device 1410 is shown.

In order to pierce a septum 1418 that is generally perpendicular to the skin 1434, a septum attachment 1460 may be provided to add a pierceable portion 1466 at an angle less than 90 degrees relative to the skin surface 1434 in the engaged position. In one embodiment pierceable portion 1466 is generally parallel with skin surface 1434 in the engaged position such that fluid coupling end 1430a and delivery end 1430b are generally parallel in both the initial and deployed positions. In one embodiment, pierceable portion 1466 is comprised of an elastomeric material.

In one embodiment, septum attachment 1460 has an internal cavity 1460a and a fluid channel 1462 that fluidly couples fluid reservoir 1420 and cavity 1460a in the assembled position. In one embodiment, fluid channel 1462 is a needle having a beveled tip 1462a. In one embodiment, cavity may be at least partially compressed prior to coupling with septum 1418. Once coupled to septum 1418 and cavity 1460a is fluidly coupled with fluid reservoir 1420, cavity 1460a expands as fluid from fluid reservoir fills cavity 1460a. In one embodiment, cavity 1460a is substantially collapsed prior to coupling with septum 1418 to reduce the amount of air delivered through needle 1430.

In another embodiment, septum attachment 1460 includes a vent 1464 fluidly coupled with cavity 1460a prior coupling septum attachment 1460 with septum 1418. In one embodiment, vent 1464 is sealed by septum 1418 once septum attachment 1460 is coupled to septum 1418. In one embodiment vent 1464 is a needle having a beveled tip 1464a.

During use, cartridge 1422 and septum attachment 1460 may be coupled prior to insertion into fluid delivery device 1410 or they may be coupled as a result of inserting cartridge 1422 into fluid delivery device 1410.

Figure 16A:
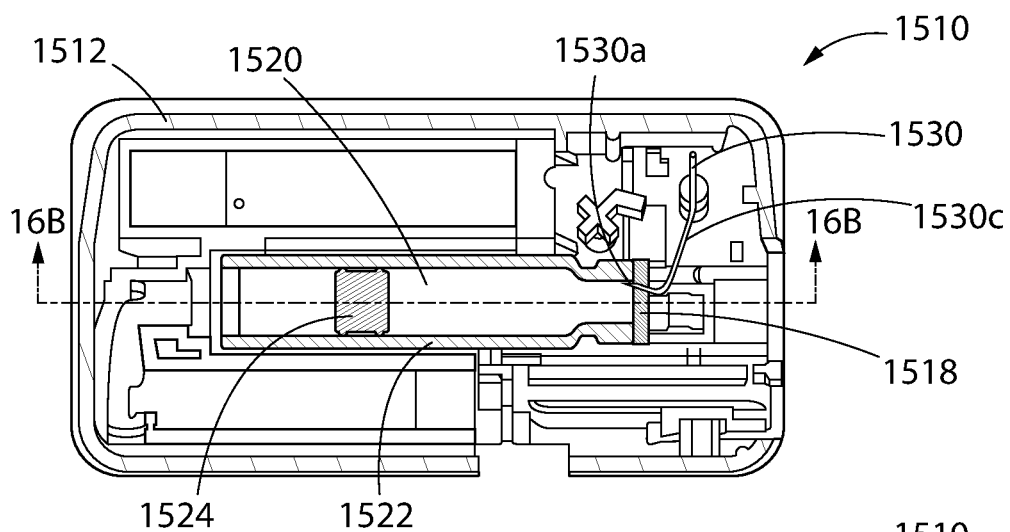
FIG. 16A is a top cross sectional view of the fluid delivery device of FIG. 15 taken along a plane indicated by line 16A-16A of FIG. 16C.
Figure 16B:
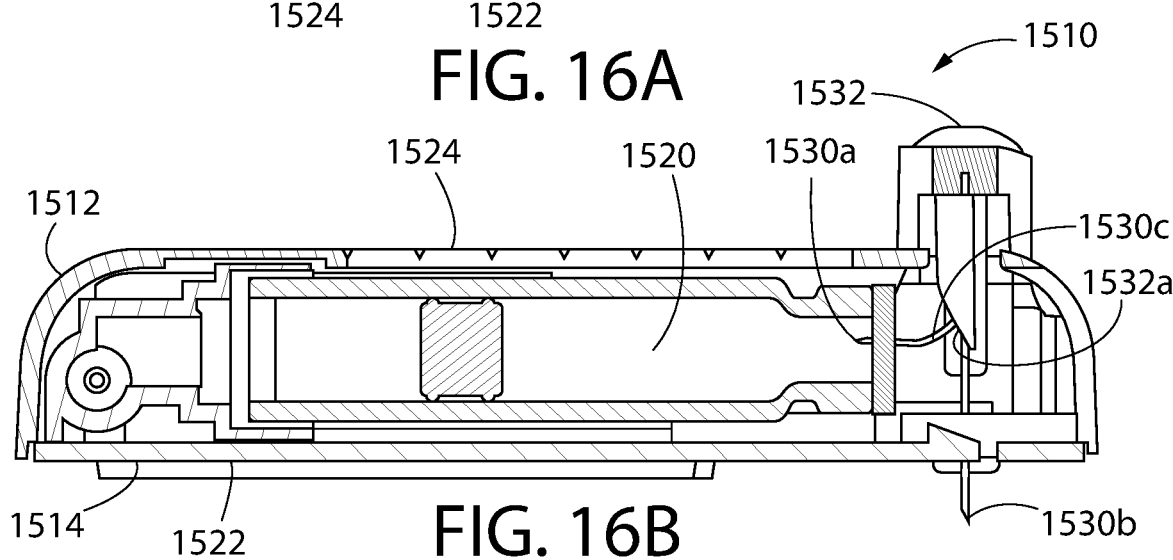
FIG. 16B is a side cross sectional view of the fluid delivery device of FIG. 15 shown in a deployed position.
Figure 16C:
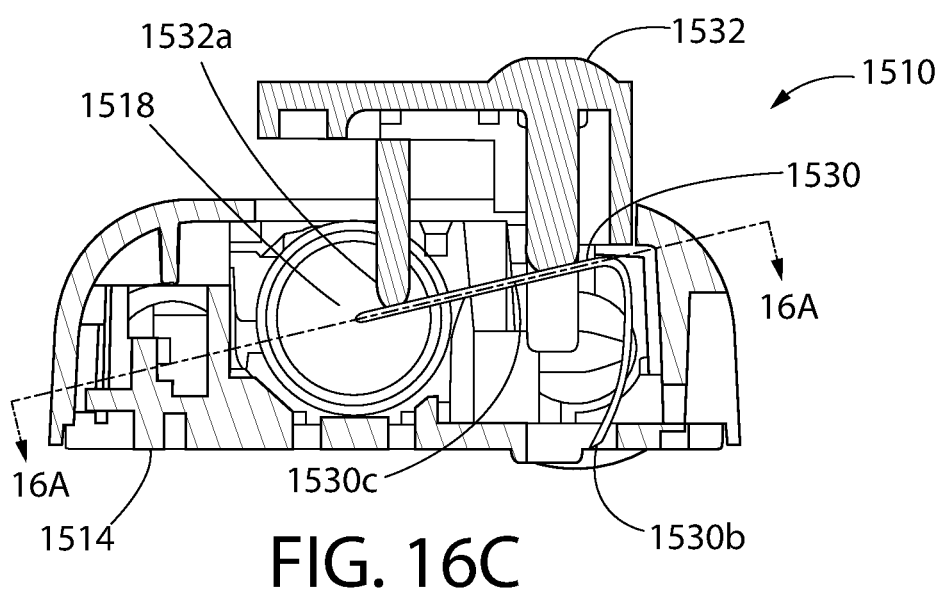
FIG. 16C is a front cross sectional view of the fluid delivery device of FIG. 15 shown in an initial position.
Figure 18E:
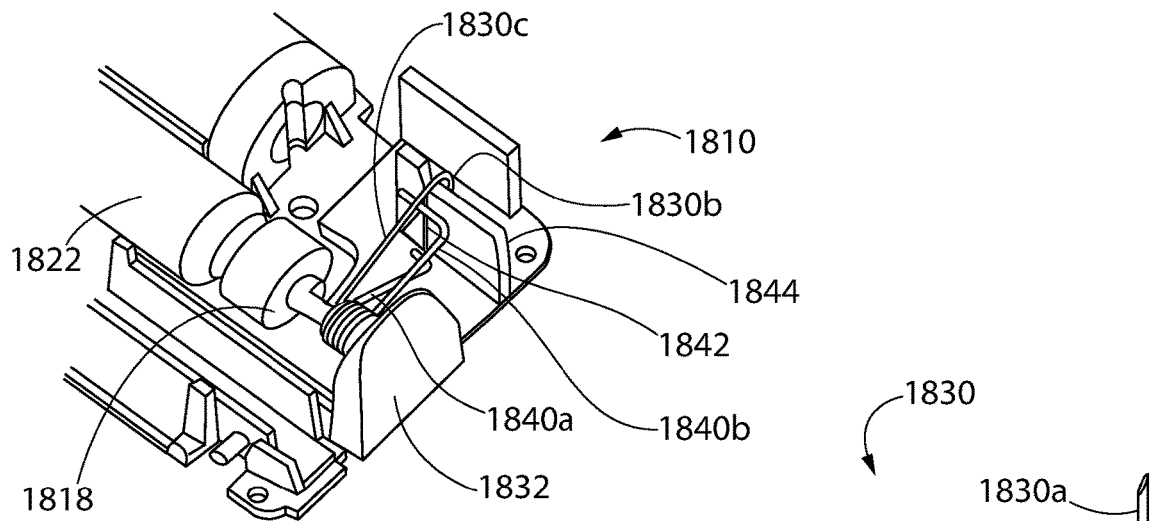
FIG. 18E is a trimetric view of the fluid delivery device of FIG. 18A shown in the locked position.
Figure 18F:
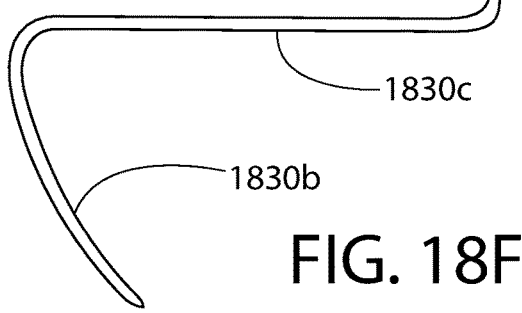
FIG. 18F is a trimetric view of the needle from the fluid delivery device of FIG. 18A.

Referring to FIGS. 15-16C, another exemplary embodiment of a fluid delivery device 1510 is shown.

In one embodiment, needle 1530 has a three dimensional curved shape. In one embodiment, fluid coupling end 1530a of needle 1530 is straight. In other embodiments, fluid coupling end 1530a is curved. In one embodiment, needle 1530 bends from fluid coupling end 1530a to a transverse section 1530c then travels under button 1532 to delivery end 1530b. In one embodiment delivery end 1530b is curved. In one embodiment, fluid coupling end 1530a is the center of the radius of the curve of the delivery end 1530b. In one embodiment, the curve of delivery end 1530b has a constant radius such that delivery end 1530b follows a generally continuous track as delivery end 1530b is moved from the initial position (FIG. 16C) to the deployed position (FIG. 7B).

In one embodiment, fluid coupling end 1530a of needle 1530 extends at least partially into septum 1518 while delivery end 1530b of needle 1530 is moved from the initial position to the deployed position. In one embodiment, fluid coupling end 1530a is fluid coupled with the fluid reservoir prior to delivery end 1530b moving from the initial position. In one embodiment, button 1532 has a ramp 1532a configured to engage needle transverse section 1530c of needle 1530 and move fluid coupling end 1530a of needle 1530 from the initial position to the deployed position. In one embodiment, the movement of needle 1530 from the initial position to the deployed position is the result of one motion of button 1532 in a single direction. In one embodiment, the direction button 1532 moves is generally perpendicular to the bottom surface 1514.

In one exemplary use, when actuated by pressing button 1532, ramp 1532a forces fluid coupling end 1530a into and through septum 1518 making a liquid connection with fluid reservoir 1520. While needle 1530 moves into fluid reservoir 1520, delivery end 1530b of needle 1530 is then rotated about the septum penetration point and delivery end 1530b travels in an arc and penetrates the skin surface stopping at the subcutaneous depth.

A catch mechanism may be provided to hold button 1532 and the needle 1530 in the deployed position for the duration of use. Once the infusion is finished, the catch on button 1532 may be released and a return spring (not shown) presses on button 1532 and rotates delivery end 1530b of needle 1530 back out of the skin.

Referring to FIGS. 17A-17D, another exemplary embodiment of a fluid delivery device 1710 is shown.

In one embodiment, needle 1730 has a three dimensional curved shape. In one embodiment, fluid coupling end 1730a is generally straight. In one embodiment, delivery end 1730b is generally curved. In one embodiment, delivery end 1730b is curved in an arc with a centerline collinear with fluid coupling end 1730a. In one embodiment, a transverse section 1730c extends between fluid coupling end 1730a and delivery end 1730b. In another embodiment, fluid coupling end 1730a may be curved, and the initial translation replaced by a rotation around a center of curvature.

A needle button 1732 may be used to cause needle 1730 to translate parallel to fluid coupling end 1730a and pierce a septum 1718 to make a liquid connection with the fluid reservoir inside of cartridge 1722. After this linear motion has completed, a cam 1738 may be used to cause needle 1730 to rotate around the axis of fluid coupling end 1730a, causing delivery end 1730b to travel into the skin tissue. Once finished, cam 1738 may be moved further to cause needle 1730 to rotate around the axis of fluid coupling end 1730a causing delivery end 1730b to retract out of the skin tissue. In one embodiment, button 1732 and cam 1738 are independently operated. In another embodiment, cam 1738 is coupled with or part of button 1732.

In one embodiment, the motion of pushing fluid coupling end 1730a of the needle 1732 into septum 1718 does not extend delivery end 1730b of needle 1730 from bottom surface 1714. In other embodiments, fluid coupling end 1730a and delivery end 1730b are moved simultaneously.

In one embodiment, cam 1738 has a track that needle 1730 extends through to guide fluid coupling end 1730b relative to bottom surface 1714. In one embodiment, cam 1738 has a first track 1738a sloped downwardly such that when cam 1738 is urged into fluid delivery device 1710, first track 1738a guides fluid coupling end in the deployed position. In one embodiment, cam 1738 has a second track 1738b extending upwardly that guides fluid coupling end 1730b back into the housing after use (e.g. a storage position). In one embodiment, cam 1738 is moved in a single direction relative to fluid delivery device 1710 to guide fluid coupling end 830b into the deployed position and into the storage position (e.g. the track is V-shaped). In an embodiment, the direction of cam 1738 is reversed between the deployed position and the storage position (e.g. the track is the shape shown). In one embodiment, an additional mechanism (not shown) moves needle 1730 from the deployed position to the storage position.

Referring to FIGS. 18A-18F, a fourth exemplary embodiment of a fluid delivery device 1810 is shown.

In one embodiment, needle 1830 has a three dimensional curved shape. In one embodiment, fluid coupling end 1830a is generally straight and generally perpendicular to septum 1818. In one embodiment, delivery end 1830b is curved. In one embodiment, the curve of delivery end 1830b is bent in an arc with the centerline collinear with fluid coupling end 1830a. In one embodiment, fluid coupling end 1830a is coupled with delivery end 1830b by a transverse section 1830c.

The movement of delivery end 1830b of needle 1830 from the initial position to the deployed position may be actuated by a spring 1840. In one embodiment, spring 1840 is a torsion spring and includes a first leg 1840a resting on the top of transverse portion 1830c of needle 1830. In one embodiment, torsion spring 1840 includes a second leg 1840b initially restrained by some combination of a needle release 1844 and/or other components. In other embodiments, first and second legs 1840a, 1840b of torsion spring 1840 can be separate springs.

A needle button 1832 may be used to cause needle 1830 to translate toward septum 1818 and pierce septum 1818 with fluid coupling end 1830a to make a liquid connection with the fluid reservoir inside of the cartridge 1822. As fluid coupling end 1830a is inserted into septum 1818, or once fluid coupling end 1830a is completely in the deployed position, transverse portion 1830c of needle 1830 reaches a slot 1842, or the end of a support in a separate part, which allows delivery end 1830b to rotate about fluid coupling end 1830a and travel into the skin tissue, pushed by first leg 1840a of torsion spring 1840.

Once delivery is finished, needle release 1844 may be moved by the user such that it pushes first leg 1840a of torsion spring 1840 off from the top of needle 1830. Next, needle release 1844 may be moved in such a way (either by the user or a release mechanism) that second leg 1840b of torsion spring 1840 pushes transverse portion 1830c of needle 1830 up and retract delivery end 1830b of needle 1830 out of the skin tissue. In other embodiments, different components can push first leg 1840a off of needle 1830, and retract needle 1830. In other embodiments, first leg 1840a of torsion spring 1840 can be left pressing down on needle 1830, and a stronger spring be used to counteract first leg 1840a and retract needle 1830.

Figure 19:
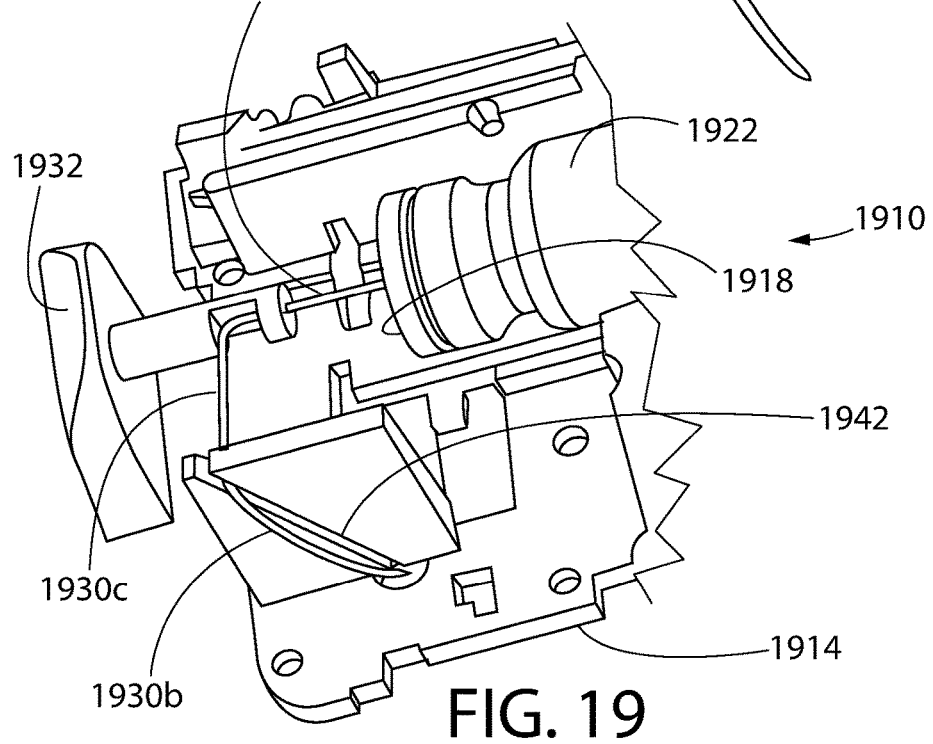
FIG. 19 is a trimetric view of a fluid delivery device in accordance with an exemplary embodiment of the present invention with the housing removed and in an initial position.
Figure 20A:
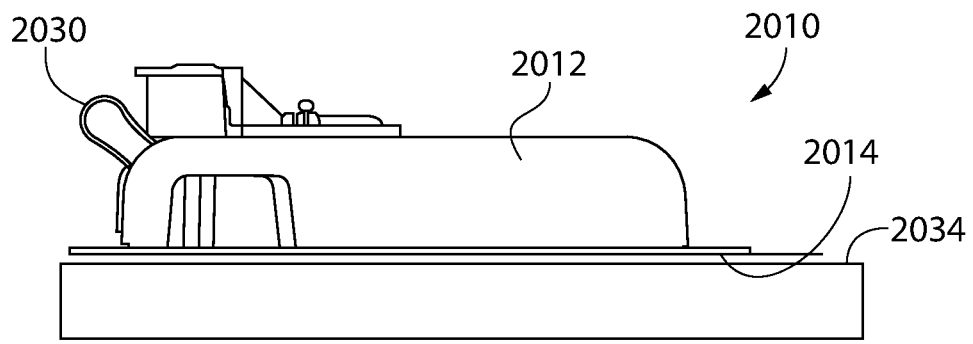
FIG. 20A is a side view of a fluid delivery device in accordance with an exemplary embodiment of the present invention in an initial position.
Figure 20B:
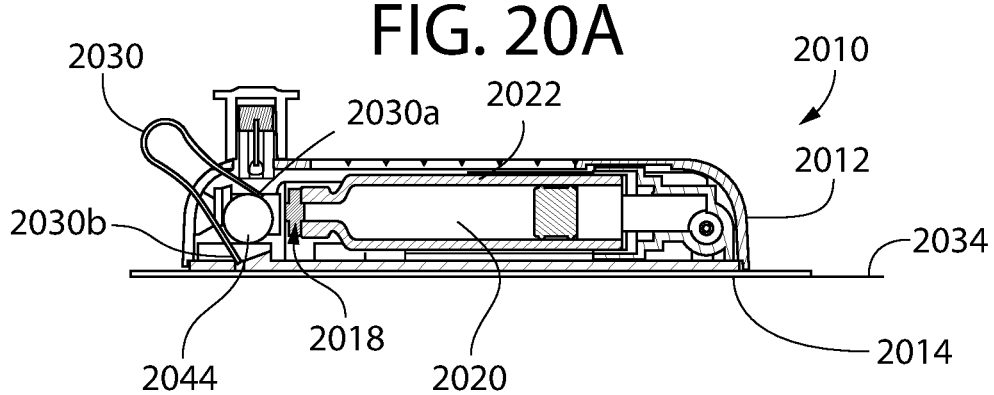
FIG. 20B is a side cross sectional view of the fluid delivery device shown in FIG. 20A.
Figure 20C:
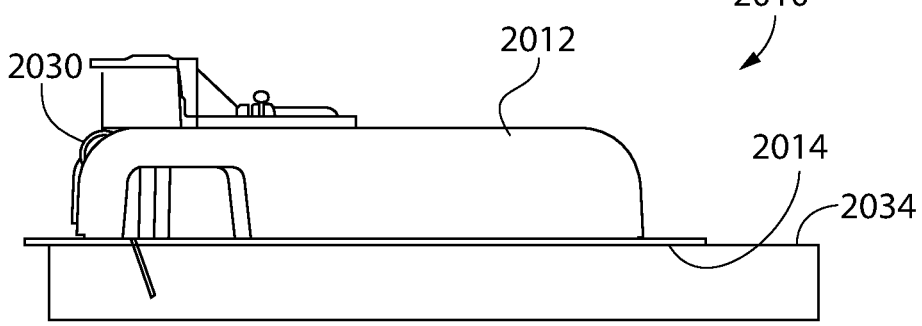
FIG. 20C is a side view of the fluid delivery device of FIG. 20A shown in a deployed position.
Figure 20D:
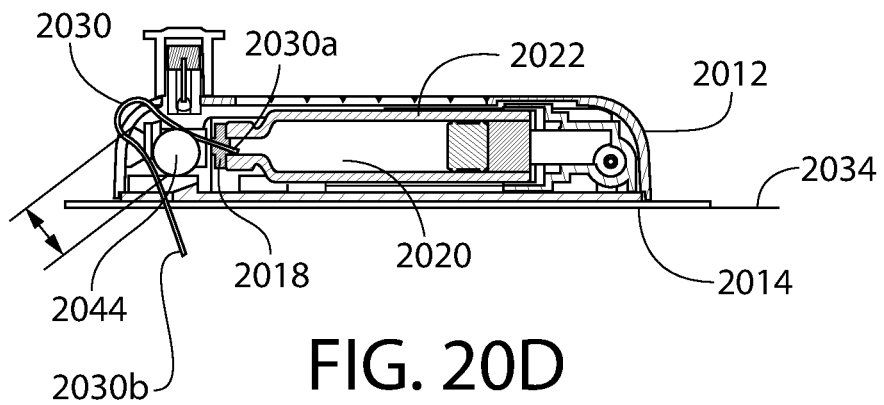
FIG. 20D is a side cross sectional view of the fluid delivery device shown in FIG. 20C.
Figure 21A:
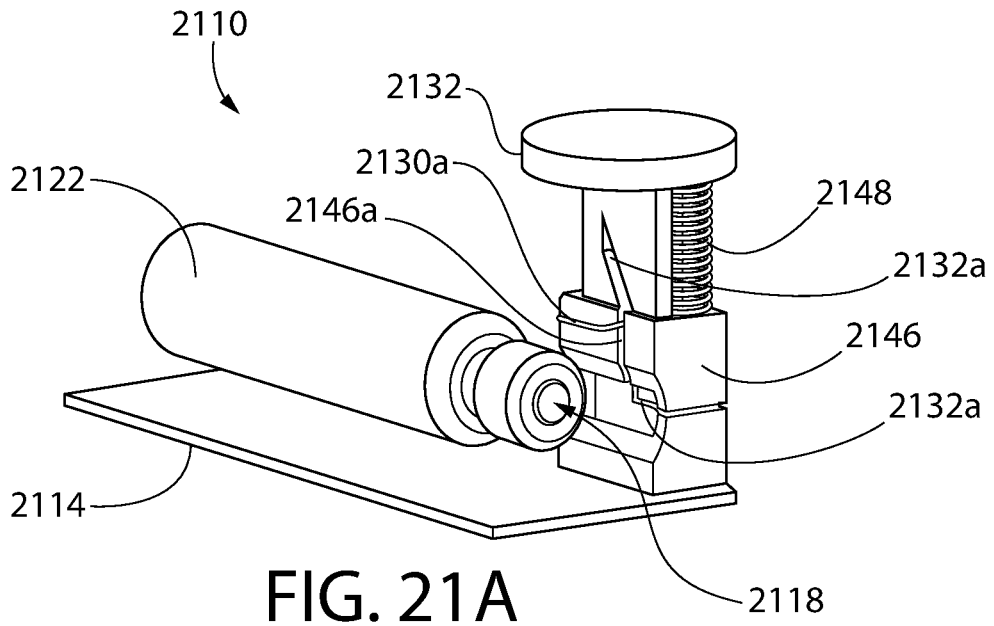
FIG. 21A is a trimetric view of a fluid delivery device in accordance with an exemplary embodiment of the present invention with the housing removed and in an initial position.
Figure 21B:
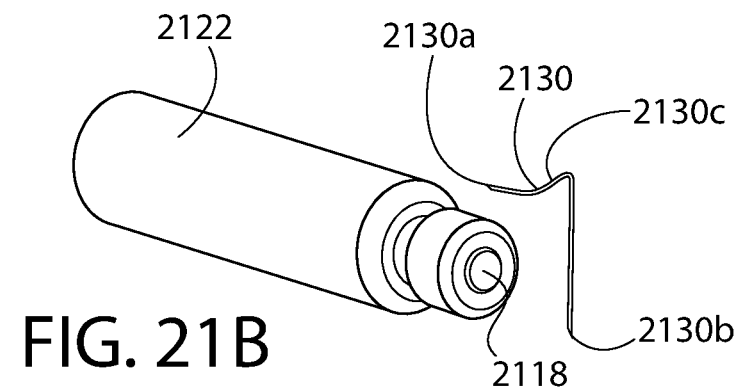
FIG. 21B is a trimetric view of the fluid delivery device shown in 21A with the button removed.
Figure 21C:
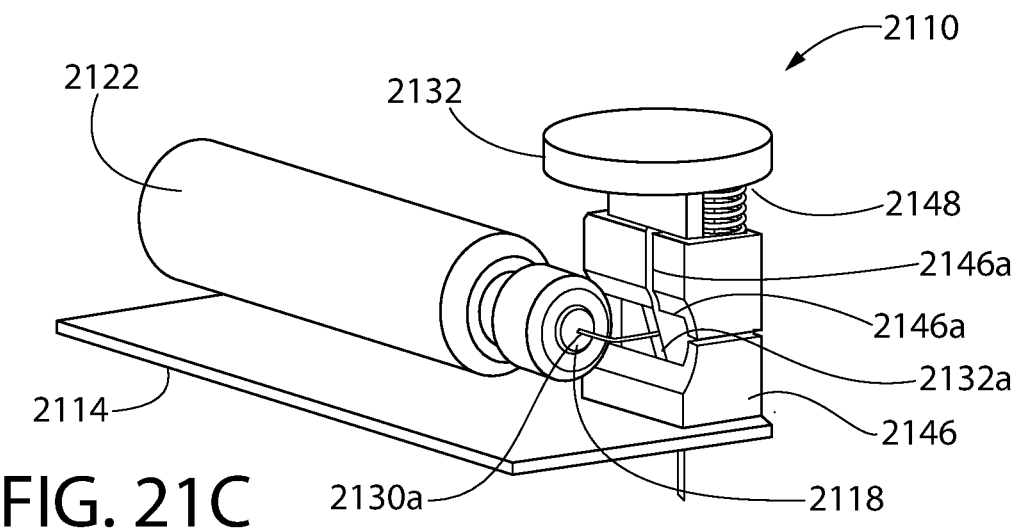
FIG. 21C is a trimetric view of the fluid delivery device of FIG. 21A shown in a partially deployed position.
Figure 21D:
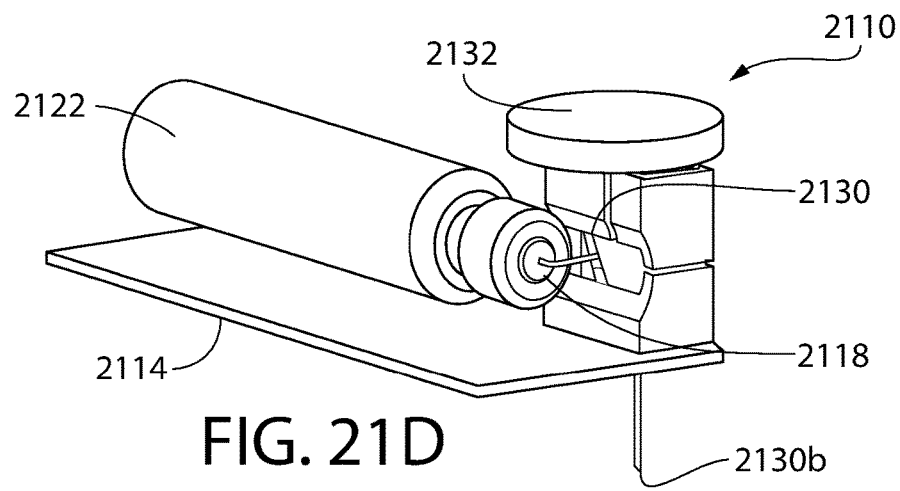
FIG. 21D is a trimetric view of the fluid delivery device of FIG. 21A shown in a deployed position.
Figure 22A:
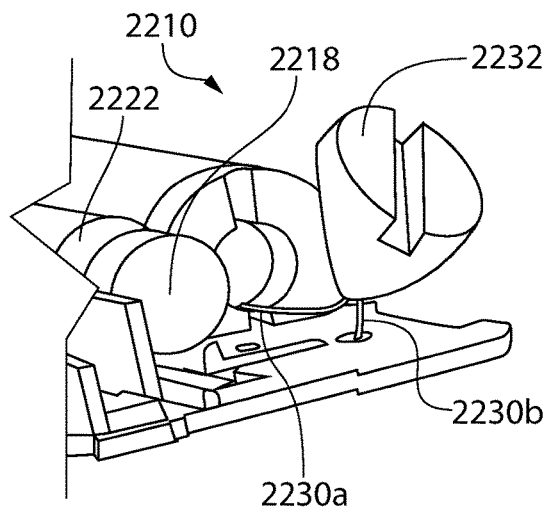
FIG. 22A is a trimetric view of a fluid delivery device in accordance with an exemplary embodiment of the present invention with the housing removed and in an initial position.
Figure 22B:
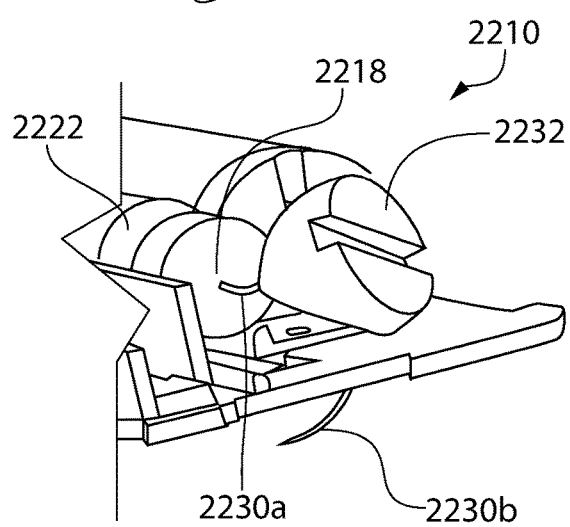
FIG. 22B is a trimetric view of the fluid delivery device of FIG. 22A shown in a deployed position.
Figure 23A:
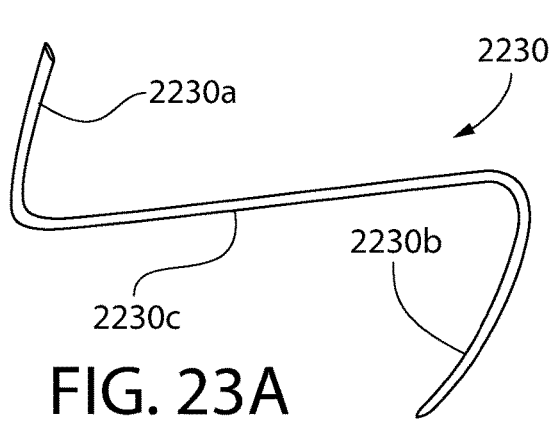
FIG. 23A is a front view of a needle from the fluid delivery device of FIG. 22A.
Figure 23B:
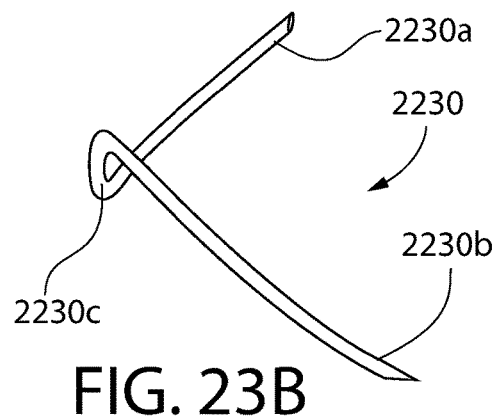
FIG. 23B is a side view of the needle shown in FIG. 23A.

Referring to FIG. 19, a fifth exemplary embodiment of a fluid delivery device 1910 is shown.

In one embodiment, a needle 1930 with one or more transverse sections 1930c connects a fluid coupling end 1930a that will pierce a septum 1918 and a helically shaped delivery end 1930b that will pierce the skin. In one embodiment, the axis of the helically shaped delivery end 1930b is coaxial with fluid coupling end 1930a. In one embodiment, fluid coupling end 1930a of needle 1930 is generally straight. A track 1942 may be provided to guide delivery end 1930b. In one embodiment, delivery end 1930b of needle 1930 is disposed within track 1942 that guides delivery end 1930b of needle 1930 from the initial position to the deployed position. In one embodiment, track 1942 is generally straight. In one embodiment, track 1942 is at an oblique angle relative to bottom surface 1914.

When actuated, a button 1932 and needle 1930 move in a single screw-like motion to insert fluid coupling end 1930a of needle 1930 into septum 1918 and rotate delivery end 1930b downwardly about fluid coupling end 1930a to penetrate the skin. In one embodiment, needle 1930 can be removed from septum 1918 and the skin by reversing the motion of button 1932, which could be accomplished by a spring or other mechanism. A latch may be provided to temporarily hold button 1932 in the deployed position.

Referring to FIG. 20A-21B, another exemplary embodiment of a fluid delivery device 2010 is shown.

In one embodiment, a needle 2030 has a fluid coupling end 2030a that extends in generally the same direction as a delivery end 2030b in the initial position. In one embodiment, needle 2030 is formed to have a V or U-turn shape similar to a bobby pin in the initial position. In one embodiment, needle 2030 includes a bend in one plane of more than approximately 135°.

In one embodiment, needle 2030 is purposely deformed elastically and potentially plastically while moving from the initial position to the second position. In one embodiment, a deforming element 2044 is provided between fluid coupling end 2030a and delivery end 2030b. In one embodiment, as needle 2030 is deployed, fluid coupling end 2030a and delivery end 2030b slide along deforming element 2044 to spread the fluid coupling end 2030a from the delivery end 2030b. In one embodiment, deforming element 2044 is generally circular in cross section. In other embodiments, deforming element is oval, square, triangular or any other shape in cross section.

In one embodiment, deforming element 2044 is not fixed relative to fluid delivery device 2010 in the deployed position allowing needle 2030 to be coupled to the remainder of fluid delivery device by septum 2018 only. In such an embodiment, needle 2030 may stay generally stationary relative to the subcutaneous tissue of the patient if housing 2012 moves with the skin surface. In such an embodiment, needle 2030 may move relatively independently of the housing 2012 minimizing the force on the tissue.

In one embodiment, fluid coupling end 2030a and delivery end 2030b are each curved to allow their travel to follow constant paths either into septum 2018 or into the patient or both. In one embodiment, fluid coupling end 2030a and delivery end 2030b are each curved in non-constant radius curves to allow their travel to follow constant paths either into septum 2018 or into the patient or both. In one embodiment, fluid coupling end 2030a and delivery end 2030b have equal lengths and similar opposing curvature. In other embodiments, fluid coupling end 2030a and delivery end 2030b are not symmetric.

A needle button or cover (not shown for clarity) may be provided over the bend in needle 2030. In one embodiment, needle 2030 is pressed at an oblique angle relative to bottom surface 2014 during deployment. In one embodiment, the angled force on needle 2030 during deployment is collinear with the force applied by the user. In other embodiments, the angled force on needle 2030 during deployment is the result of a redirection from a slanted button base or other configuration over needle 2030.

During deployment, the depressing of needle 2030 forces fluid coupling end 2030a and delivery end 2030b over deforming element 2044 which deforms one or both of the legs to direct them to their deployed positions. In one embodiment, a latch or other retention mechanism retains needle 2030 in the deployed position. In one embodiment, when infusion is complete, the latch is released and a return mechanism such as a spring between needle 2030 and deforming element 2044 can force needle 2030 back to its retracted position. In one embodiment, when infusion is complete, the latch is released and the stored strain in needle 2030 can force needle 2030 back to its retracted position.

Referring to FIG. 21A-21D, a seventh exemplary embodiment of a fluid delivery device 2110 is shown.

In one embodiment, a needle 2130 bent into three dimensions is pressed into the skin and then needle 2130 is rotated to penetrate septum 2118. In one embodiment, needle 2130 includes three sections: a straight delivery end 2130b for penetrating the skin, a transverse section 2130c and a curved fluid coupling end 2130a for penetrating septum 2118. In one embodiment, needle 2130 extends through a base 2146 that allows translation and rotation of fluid coupling end 2130a of needle 2130. In one embodiment, transverse section 2130c of needle 2130 passes through a slot 2146a in base 2146 that controls the rotational position of needle 2130. A button 2132 with an angled slot 2132a is held by base 2146 and can travel perpendicular to the skin. Transverse section 2130c of needle 2130 may pass through angled slot 2132a. In one embodiment, there is a return force element 2148 (e.g., a spring) that acts to force button 2132 back into the storage position. In one embodiment, a latch or retaining mechanism may be provided to temporarily retain button 2132 in the deployed position.

When actuated, button 2132 is depressed, button 2132 acts on transverse section 2130c of needle 2130. Slot 2146a pushes needle 2130 an angle toward septum 2118 and bottom surface 2114. Initially, needle 2130 does not rotate due to the limitation set on it by slot 2146a in base 2146. Once needle 2130 has reached a certain depth, such as full deployment depth, fluid coupling end 2130a is moved horizontally into septum 2118 because slot 2146a no longer restricts horizontal motion. In the final deployed position, button 2132 is fully depressed and fluid coupling end 2130a has rotated into septum 2118 as a result of the force on needle 2130 by slot 2132a in button 2132.

For withdrawal, a latch or retaining mechanism on button 2132 would be released and return force element 2148 forces button back up and into the storage position.

In another embodiment, delivery end 2130b could be prevented from rotating and needle 2130 could be bent essentially elastically to be inserted into septum 2118.

In another embodiment, fluid coupling end 2130a may be, in whole or in part, helical, and all or a portion of the rotation of needle 2130 may occur while the delivery end 2130b is moving into the tissue.

In another embodiment, insertion and/or removal of fluid coupling end 2130a is accomplished by a spring or springs, instead of an angled slot 2132a in button 2132.

Referring to FIG. 22A-23B, another exemplary embodiment of a fluid delivery device 2210 is shown.

In one embodiment, a needle 2230 with a transverse section 2230c connects a helical fluid coupling end 2230a and a helical delivery end 2230b. In one embodiment, helical fluid coupling end 2230a and a helical delivery end 2230b the axes of the helices being coincident. In one embodiment, helical fluid coupling end 2230a and a helical delivery end 2230b and have the same pitch.

When actuated, a button 2232 and needle 2230 move in a single screw-like motion to transition needle 2230 from the initial position to the deployed position. In one embodiment, needle 2230 can be transitioned to the storage position by reversing the motion, either manually or by a return mechanism such as a spring. In one embodiment, a latch or retaining mechanism temporarily retains needle 2230 in the deployed position.

Figure 24A:
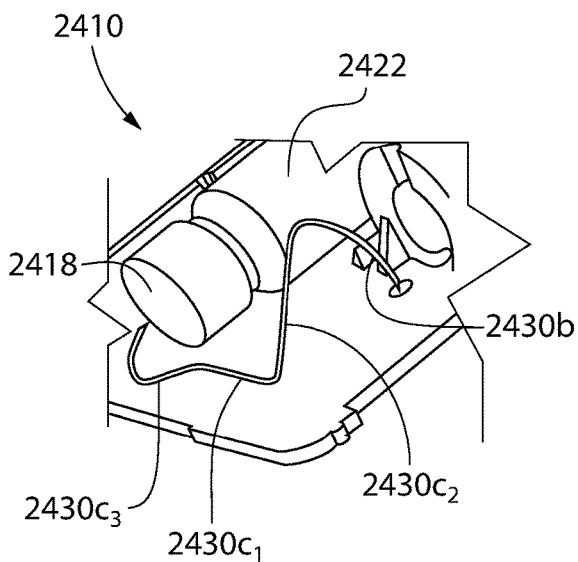
FIG. 24A is a trimetric view of a fluid delivery device in accordance with an exemplary embodiment of the present invention with the housing removed and in an initial position.
Figure 24B:
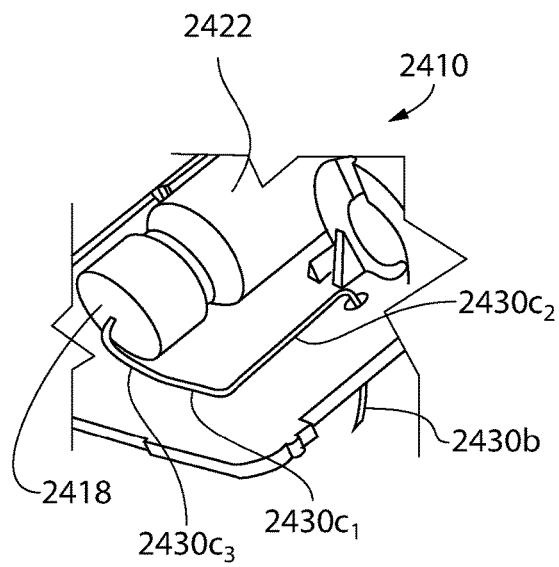
FIG. 24B is a trimetric view of the fluid delivery device of FIG. 24A shown in a deployed position.

Referring to FIG. 24A-24B, a ninth exemplary embodiment of a fluid delivery device 2410 is shown.

In one embodiment, a needle 2430 includes one or more transverse sections 2430 that connects fluid coupling end 2430a and delivery end 2430b. In one embodiment, fluid coupling end 2430a and delivery end 2430b are curved. In one embodiment, fluid coupling end 2430a and delivery end 2430b lie essentially on parallel planes. In one embodiment, fluid coupling end 2430a and delivery end 2430b each have circular arc geometry with the axes of the arcs being coincident. In one embodiment, transverse section 2430c has three linear sections 2430c1, 2430c2 and 2430c3, with the first transverse section 2430ci coaxial with the axis of rotation. Transverse section 2430c may instead have other bends.

When actuated, needle 2430 may rotate about a common axis, such as first transverse section 2430c₁ to move needle 2430 into the deployed position. In one embodiment, a needle button is provided. The needle can be removed from both by reversing the motion, which could be accomplished by a spring. In one embodiment, needle 2430 can be transitioned to the storage position by reversing the motion, either manually or by a return mechanism such as a spring. In one embodiment, a latch or retaining mechanism temporarily retains needle 2430 in the deployed position.

Figure 25A:
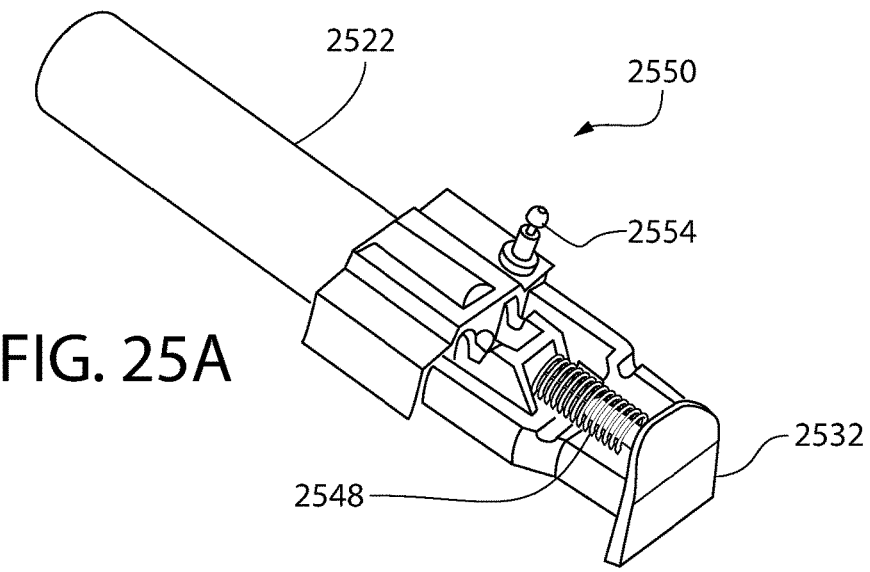
FIG. 25A is a trimetric view of a vial assembly for use with a fluid delivery device in accordance with an exemplary embodiment of the present invention with the housing removed.
Figure 25B:
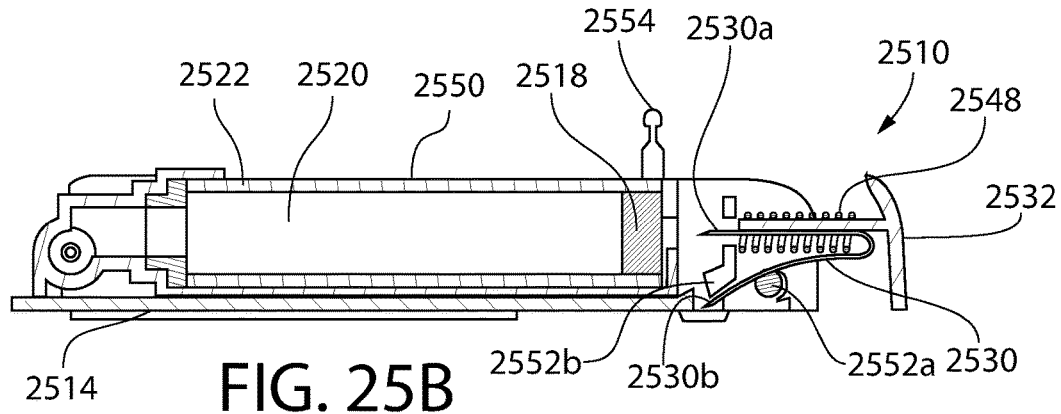
FIG. 25B is a side cross sectional view of the fluid delivery device shown in FIG. 25A.
Figure 25C:
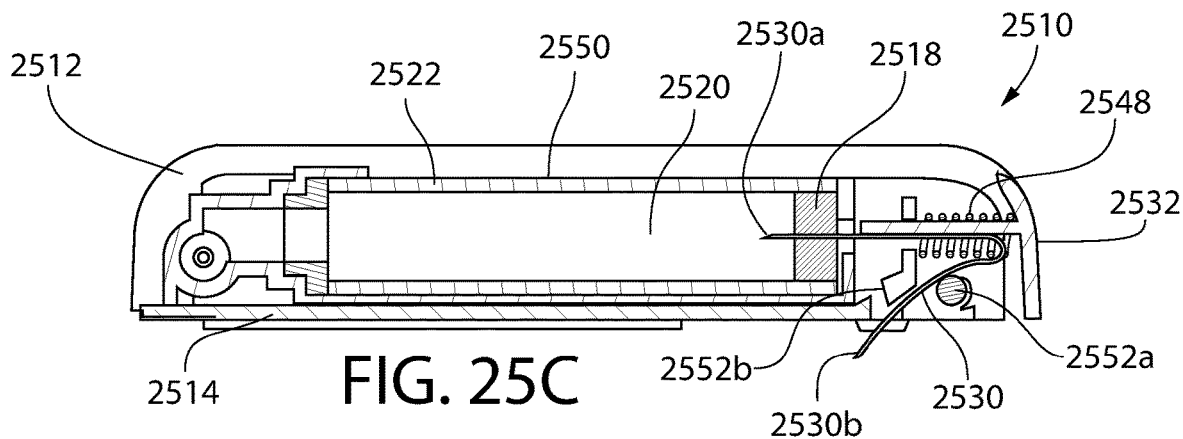
FIG. 25C is a side cross sectional view of the fluid delivery device of FIG. 25A shown in the deployed position.
Figure 26A:
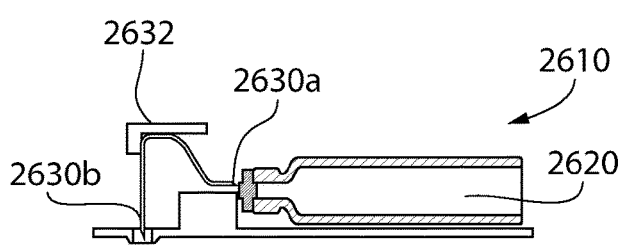
FIG. 26A is a side cross sectional view of a fluid delivery device in accordance with an exemplary embodiment of the present invention shown in an initial position.
Figure 26C:
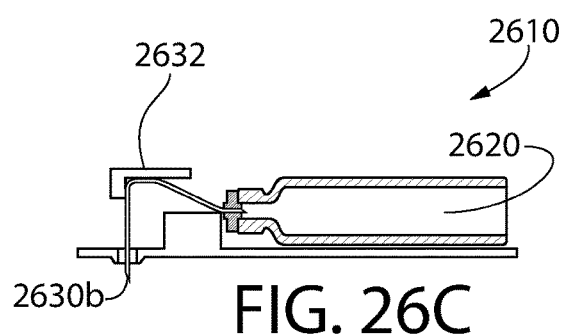
FIG. 26C is a side cross sectional view of the fluid delivery device of FIG. 26A shown in a second partially deployed position.
Figure 26B:
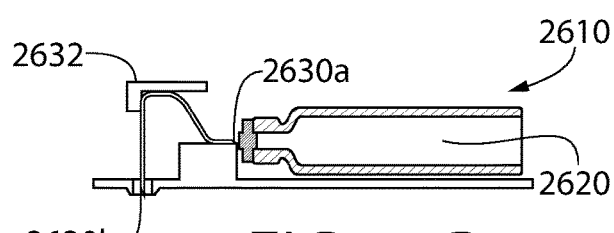
FIG. 26B is a side cross sectional view of the fluid delivery device of FIG. 26A shown in a first partially deployed position.
Figure 26D:
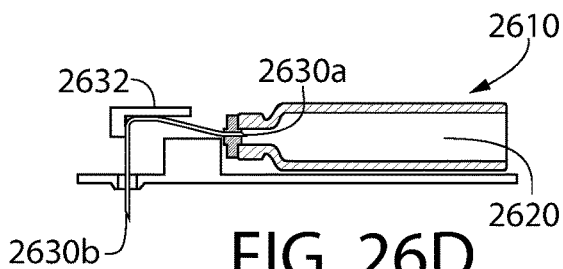
FIG. 26D is a side cross sectional view of the fluid delivery device of FIG. 26A shown in a deployed position.

Referring to FIG. 25A-25C, a tenth exemplary embodiment of a fluid delivery device 2510 is shown.

In one embodiment, the needle mechanism and the vial are combined as a vial assembly 2550 that may be inserted into a fluid delivery device 2510. In one embodiment, vial assembly 2550 is pre-filled with a medicament before being coupled with the fluid delivery device 2510.

In one embodiment, needle 2530 is preformed to have a generally straight fluid coupling end 2530a and a curved delivery end 2530b. In one embodiment, one or more deforming surfaces 2552a, 2552b are provided to guide delivery end 2530b into the deployed position. In one embodiment, deforming surfaces 2552a, 2552b on provided on opposing sides of delivery end 2530b. In one embodiment, deforming surfaces 2552a, 2552b are moveable relative to bottom surface 2514 such that needle 2530 is moveable in the deployed position.

In one embodiment, needle 2530 includes a bend in one plane more than 100°. In one embodiment, fluid coupling end 2530a is generally straight and delivery end 2530b is curved in a direction opposite to the bend between fluid coupling end 2530a and delivery end 2530b.

During use, after removing a locking pin 2554 and pressing button 2532 forces fluid coupling end 2530a into septum 2518 and forces delivery end 2530b over deforming surfaces 2552a, 2552b along a slanted or curved path out of bottom surface 2514 and into the deployed position. In another embodiment, releasing locking pin 2554 causes button 2532 to be deployed automatically without a separate action step by the user.

When infusion is complete, a latch or retaining mechanism may be released and a return mechanism 2548, e.g., a spring, forces needle 2530 into the storage position.

Referring to FIG. 26A-26D, an eleventh exemplary embodiment of a fluid delivery device 2610 is shown.

In one embodiment, fluid coupling end 2630a is deformed during deployment and delivery end 2630b is generally straight. In one embodiment, the needle button 2632 is driven along the axis of delivery end 2630b during deployment and fluid coupling end 2630a is deformed to translate in a direction generally perpendicular to the axis of delivery end 2630b during deployment.

In other embodiments, both fluid coupling end 2630a and delivery end 2630b are deformed during deployment.

Figure 27A:
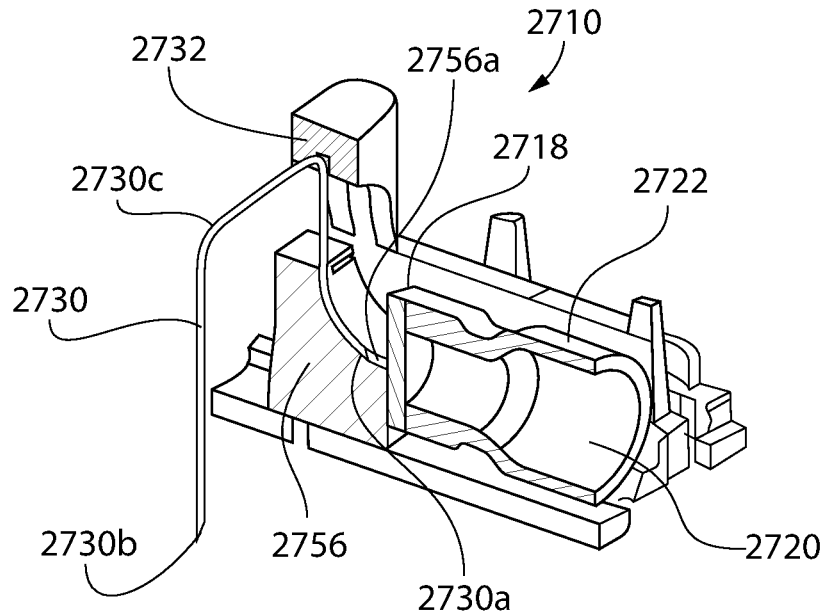
FIG. 27A is a trimetric cross sectional view of a portion of a fluid delivery device in accordance with an exemplary embodiment of the present invention shown in an initial position.
Figure 27B:
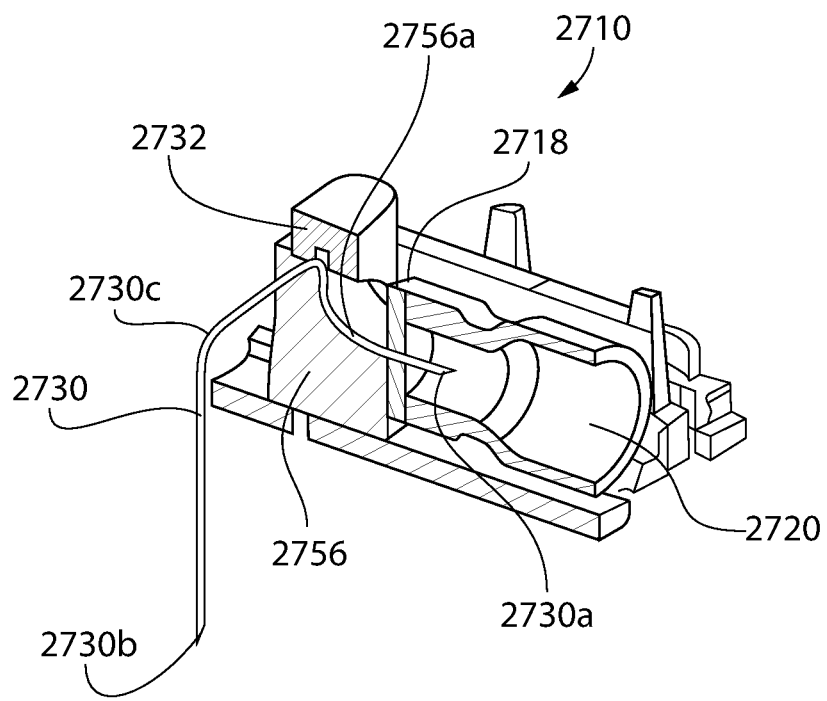
FIG. 27B is a trimetric cross sectional view of the fluid delivery device of FIG. 27A shown in a deployed position.

Referring to FIG. 27A-27B, a twelfth exemplary embodiment of a fluid delivery device 2710 is shown.

In one embodiment, fluid coupling end 2730a is flexible. Fluid coupling end 2730a may be comprised of a different, more flexible material from the remainder of needle 2730 and/or may have smaller gauge than delivery end 2730b. In one embodiment, fluid coupling end 2730a is guided through a curve by a needle guide 2756. In one embodiment needle guide 2756 includes a channel 2756a that guides fluid coupling end 2730a toward septum 2718.

During use, a downward force is applied to button 2732 along an axis of delivery end 2730b forcing delivery end 2730b into the deployed position. Simultaneously, the downward force on button 2732 forces fluid coupling end 2730a through needle guide 2756 and into septum 2718.

In one embodiment, needle guide 2756 assists in retaining cartridge 2722 within fluid delivery device 2710.

When infusion is complete, a latch or retaining mechanism may be released and a return mechanism, e.g., a spring, forces needle 2730 into the storage position.

Referring to FIGS. 28A-28D, there is shown another exemplary embodiment of a needle assembly for use with the fluid delivery device 2810. A cartridge 2822, including a fluid reservoir, may be inserted into the drug delivery device 2810. In one embodiment, the cartridge 2822 is prefilled with a fluid such as insulin prior to being inserted into the drug delivery device 2810. In one embodiment, the cartridge 2840 is slid into a channel inside of the drug delivery device 2810 through an opening 2800a. The fluid delivery device 2810 may include a closure, such as a pivoting door 2805, that closes the opening 2800a once the cartridge 2822 has been installed. In one embodiment, door 2805 includes a needle assembly 2801 having a needle 2830. In alternative embodiments, the cartridge 2822 is preinstalled in the drug delivery device 2810, or the cartridge 2822 is inserted through an opening in a top or bottom or different end of the drug delivery device 2810.

The door 2805 may be pivotably attached to the fluid delivery device 2810, e.g., such as with a hinge. The hinge may be a living hinge constituted by a thin section in the door 2805 and/or the housing of the fluid delivery device 2810. In one embodiment, the hinge and the door 2805 or co-molded with the housing 2812.

In alternative embodiments, the door 2805 is a separate assembly from the fluid delivery device 2810 and couples to the fluid delivery device 2810 after the cartridge 2822 is inserted into the fluid delivery device 2810. In one embodiment, the door 2805 is pre-attached to the septum 2818 of the cartridge 2822 and latches to the fluid delivery device 2810 after the cartridge 2822 has been inserted into the fluid delivery device 2810. In one embodiment, the door 2805 is pre-attached to the septum seal of the cartridge 2822 and slides over the cartridge 2822 after the cartridge 2822 has been inserted into the fluid delivery device 2810.

The attachment of the door 2805 to the housing of the fluid delivery device 2810 such as by a hinge, may have a degree of play such that the door 2805 may be shifted relative to the housing. The needle assembly 2801 may include an alignment feature 2807 that is configured to essentially nest around the end of the cartridge 2822. In one embodiment, alignment feature 2807 shifts the cartridge 2822 and/or the door 2805 into the proper position and ensures alignment of the needle 2830 and the septum 2818. In one embodiment, the alignment feature 2807 has a taper in the inside leading edge to allow the alignment feature 2807 to more easily move over the end of the cartridge 2822. In one embodiment, alignment feature 2807 snap fits onto cartridge 2822 in the initial position and/or primed state.

Figure 28A:
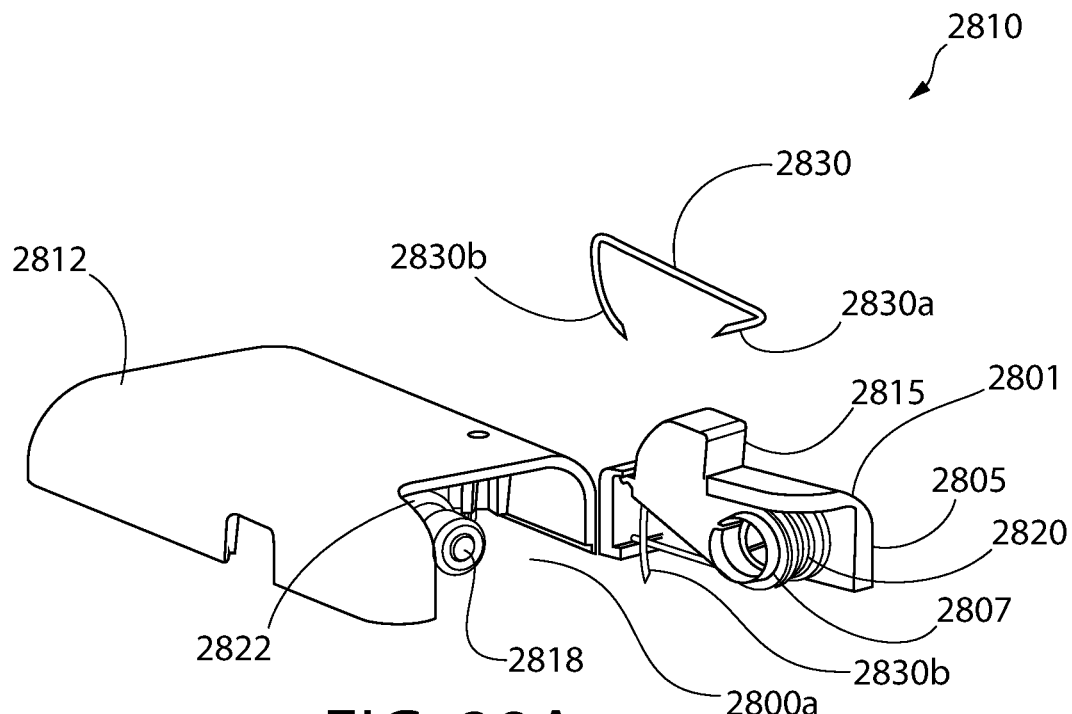
FIG. 28A is a trimetric view of a front of a fluid delivery device in accordance with an exemplary embodiment of the present invention.
Figure 28B:
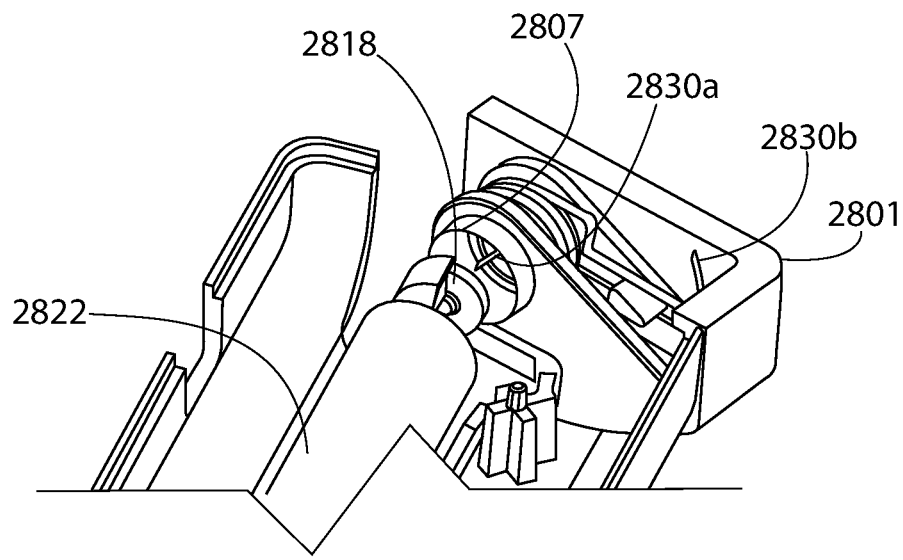
FIG. 28B is a trimetric view of a bottom of the fluid delivery device shown in FIG. 28A with the bottom of the housing and a portion of the cartridge removed for clarity.
Figure 28C:
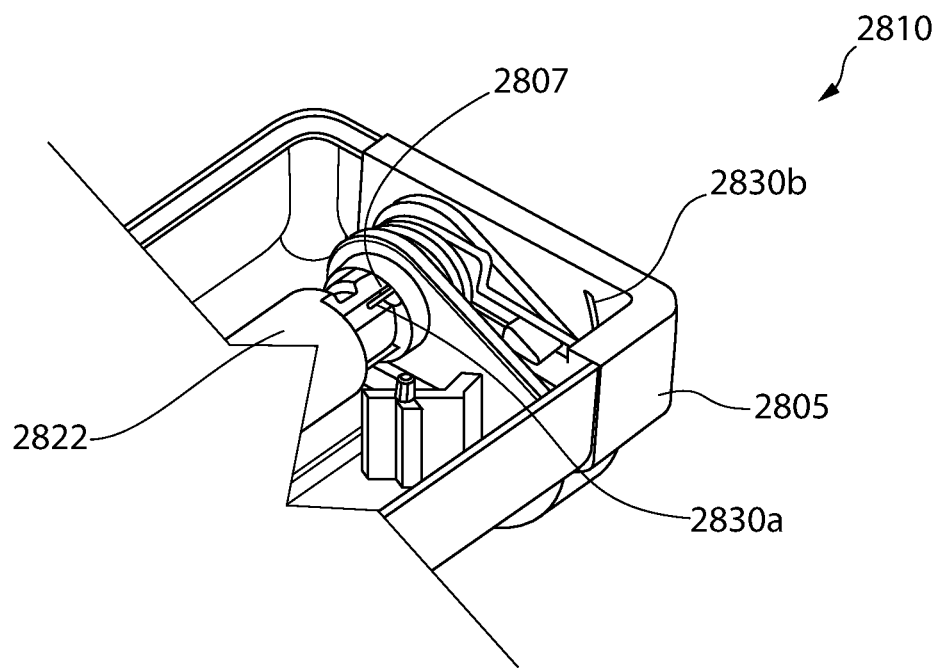
FIG. 28C is a trimetric view of a bottom of the fluid delivery device shown in FIG. 28B with the door closed.
Figure 28D:
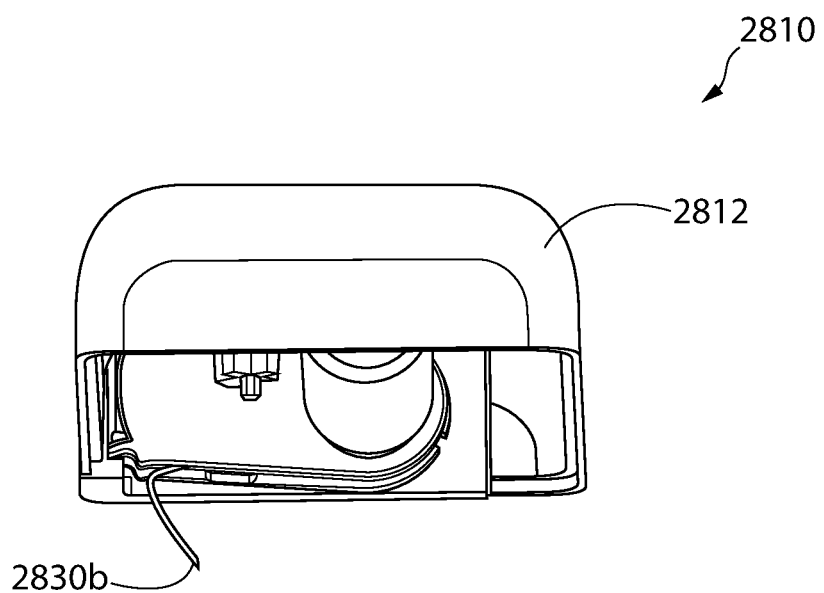
FIG. 28D is a trimetric view of a rear of the fluid delivery device shown in FIG. 28B in the deployed state.
Figures 29A, 29B:
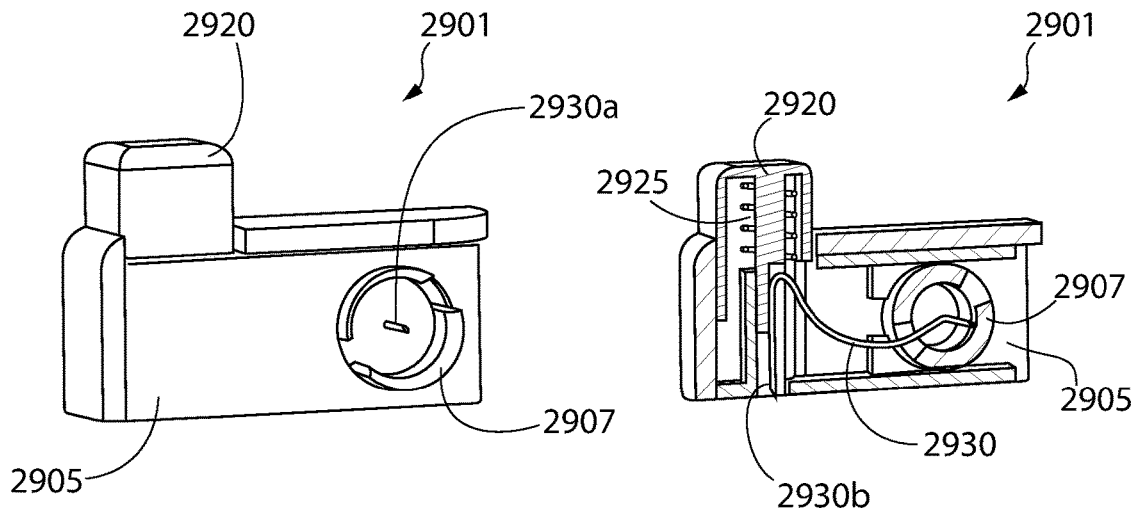
FIG. 29A is a trimetric view of a needle assembly in accordance with an exemplary embodiment of the present invention.
FIG. 29B is a cross sectional view of the needle assembly shown in FIG. 29A.
Figures 29C, 29D:
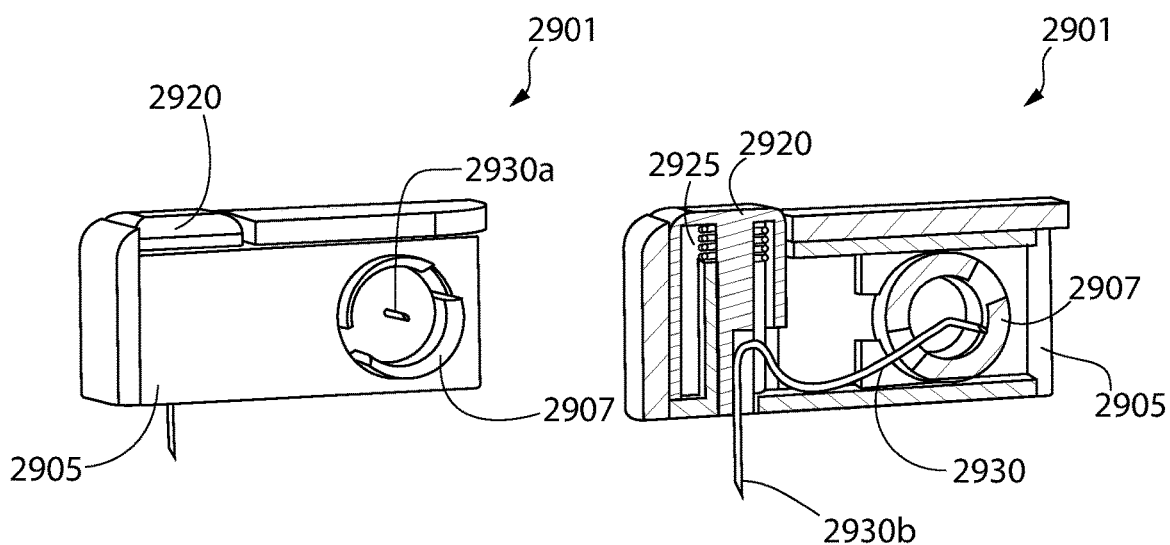
FIG. 29C is a trimetric view of the needle assembly shown in FIG. 29C in the deployed position.
FIG. 29D is a cross sectional view of the needle assembly shown in FIG. 29C.

A fluid coupling end 2830a of the needle 2830 that is configured to penetrate the septum 2818 may be curved with a radius generally centered with the axis of the hinge. In one embodiment, the needle 2830 is bent in two dimensions as shown in the detail of FIG. 28A. The fluid coupling end 2830a may be bent at essentially a right angle and positioned to penetrate the fluid reservoir septum 2818 when the door 2805 is being closed (FIG. 28B and FIG. 28C). The end of the cartridge 2822 is shown sectioned for clarity). For example, in some embodiments, fluid coupling end 2830a may be positioned within alignment feature 2807 and configured to penetrate the septum 2818 as or when alignment feature 2807 is engaged with cartridge 2822. The delivery end 2830b of the needle 2830 may also be bent so that it is in a plane substantially perpendicular to the bottom surface of the fluid device 2810 and thus the surface of the skin. In one embodiment, the delivery end 2830b of the needle 2830 has a radius of curvature that is essentially centered on the axis of the fluid coupling end 2830a of the needle 2830. In one embodiment, the needle assembly is designed to first rotate the fluid coupling end 2830a of the needle 2830 generally about the axis of the delivery end 2830b of the needle 2830 into the septum 2818 and then rotate the delivery end 2830b of the needle 2830 generally about the axis of the fluid coupling end 2830a of the needle 2830 out of the fluid delivery device 2810 and into the patient's skin.

The needle assembly 2801 may include an actuation trigger or button 2815 coupled to the needle 2830. The needle assembly 2801 may include a return element 2820 such as a spring for biasing the needle 2830 toward an initial or retracted position.

In one embodiment, closing the door 2805 over open end 2800a forces the fluid coupling end 2830a of the needle 2830 to penetrate the septum 2818 and fluidly couple the fluid reservoir and the needle 2830. This position may be referred to as a primed state. (See FIG. 28C).

Depressing the button 2815 may extend the delivery end 2830b of the needle 2830 from the housing and into the patient's skin. This position may be referred to as the deployed or delivery position. (See FIG. 28D). In one embodiment, depressing the button 2815 rotates the button 2815 around the axis of the fluid coupling end 2830a of the needle 2830. In one embodiment, there is a catch mechanism (not shown for clarity) that is configured to retain the button 2815 at the end of its travel holding the needle 2830 in its fully deployed position.

Once the user is done with the delivery device 2810, the needle 2830 is removed from their tissue. In one embodiment, there is a return element 2820 that is further deformed when the button is depressed. Once the return element 2820 is released, the return element 2820 returns to its more relaxed state lifting the needle 2830 out of the tissue back to the primed state. In one embodiment, the needle 2830 is secured to the button 2815 and the return element 2820 returns both the button 2815 and the return element 2820 to positions where needle 2830 is no longer in the tissue. In one embodiment, after retraction the needle 2830 is secured in a groove within the button 2815 to prevent further use of the needle 2830. In an alternative embodiment, the button 2815 remains depressed at the end of delivery but the return element 2820 retracts the needle 2830 back into the housing. In one embodiment, the return element 2820 is a torsion spring. In one embodiment, the return element 2820 is a compression spring. In one embodiment, once the needle 2830 has been retracted, the delivery end 2830b is retained within the fluid delivery device 2810 to prevent further exposure of the delivery end 2830b and avoid accidental needle sticks.

In one embodiment, the button 2815 is integrated with the fluid delivery device 2810 and the needle 2830 is carried by the door 2805. In such an embodiment, the needle 2830 and the button 2815 interface once the door 2805 is closed. In one embodiment, the door 2805 slides on a track or tracks that hold and guide the cartridge 2822 during insertion. In one embodiment, the door 2805 slides on a track or tracks independent of the cartridge 2822 insertion process.

Referring to FIGS. 29A-29D, there is shown a second exemplary embodiment of a needle assembly 2901. Needle assembly 2901 is similar to needle assembly 2801 discussed above except that in needle assembly 2901 the needle 2930 enters the skin in a generally straight line rather than through an arc. In one embodiment, the needle 2930 bends during deployment.

In one embodiment, the delivery end section 2930b of the needle 2930 is guided to enter the skin in a generally straight line. In one embodiment, there is a bend or arc in the center section 2930c of the needle 2930 and the fluid coupling end section 2930a of the needle is allowed to rotate in the septum of the cartridge. During deployment, the distance between the fluid coupling end section 2930a of the needle 2930 and the delivery end section 2930b of the needle 2930 varies as the needle path is not following an arc of constant radius. The curve of the center section 2930c of the needle 2930 can flex to take in and/or let out space between the fluid coupling end section 2930a and the delivery end section 2930b of the needle 2930. In one embodiment, there is more than one bend or arc in the center section 2930c of the needle 2930.

In one embodiment, the center section 2930c curves generally in the same direction as the delivery end section 2930b of the needle 2930 to minimize height of the center section 2930c when the needle 2930 is in the deployed position. In one embodiment, the center section 2930c curves generally in the opposite direction as the delivery end section 2930b of the needle 2930 to minimize interference with other device mechanisms or features when the needle 2930 is in the deployed position. In one embodiment, the center section 2930c and the first and delivery end sections 2930a, 2930b are formed such that the needle 2930 is not under any bending stress when the needle 2930 is in the deployed position.

In one embodiment, an actuation button 2920 and a return element 2925, such as a spring 2925 are also mounted to the door 2905.

In one embodiment, the door 2905 is pre attached to the cartridge and latches to the housing of the fluid delivery device upon insertion of the cartridge. In one embodiment, door 2905 is rotatably attached to the housing and closes over and couples with the cartridge after the cartridge is inserted into the fluid delivery device.

Prefilled cartridges commonly have septum seals on one end and pistons or plungers inside at an opposite end. The medicament is delivered by fluidly connecting the material inside of the cartridge through the septum with the patient's body and then pressing on the piston.

In most fluid delivery systems, and especially in hydraulically driven fluid delivery devices, the accurate and effective delivery of the medicament requires that there be little, and preferably no, compressible gaps between the drive mechanism and the piston, little, and preferably no, pre-delivery pressure on the piston and that the needle be accurately inserted into the septum.

Inserting a cartridge in a delivery device can result in performance issues due to the length tolerance of the cartridge resulting in unacceptably large gaps that are compressible between the drive mechanism and the piston and a misaligned needle insertion system.

In addition, temperature changes in storage and transport may cause changes in component dimensions and liquid volumes. If there is a significant difference in the coefficients of thermal expansion between components, then there may be significant changes in the components positions which could exacerbate tolerance issues. This is especially significant in hydraulically driven systems where the fluid is likely to have much greater thermal expansion characteristics than the solid components of the device.

It is therefore desired to have a simple to use mechanism that allows a prefilled cartridge to be inserted in a delivery device and can accommodate a cartridge minimizing compressible gaps between the drive mechanism and the piston. In one embodiment, the length tolerance of the cartridge usable with the delivery device is at least +/−0.4 mm. The delivery device may allow for minimal pressure in the system due to insertion or the insertion mechanism. The delivery device may allow for proper alignment between the cartridge septum seal and the needle mechanism. It is also beneficial if the delivery device can compensate for thermal expansion effects.

Referring to the drawings in detail, wherein like reference numerals indicate like elements throughout, there is shown in FIGS. 4A-14B fluid delivery devices in accordance with exemplary embodiments of the present invention.

Referring to FIGS. 30A-30I, an exemplary embodiment of a fluid delivery device 3010 is shown.

Figure 30A:
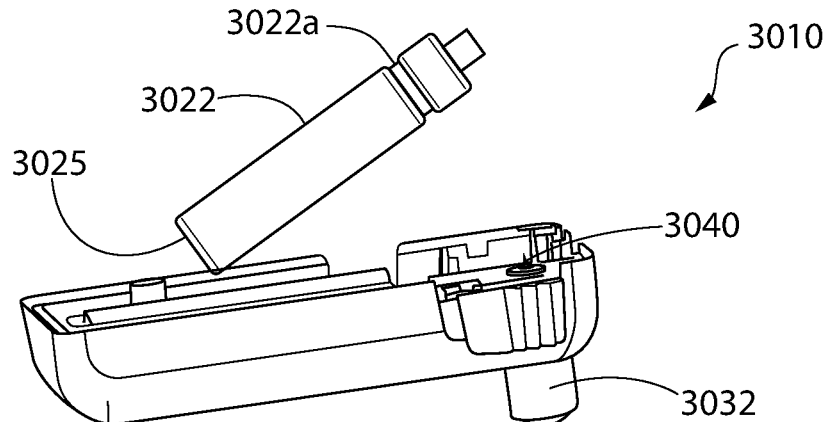
FIG. 30A is a trimetric view of the bottom of a fluid delivery device in accordance with an exemplary embodiment of the present invention with the cartridge ready to be inserted and the base is removed for clarity.
Figure 30B:
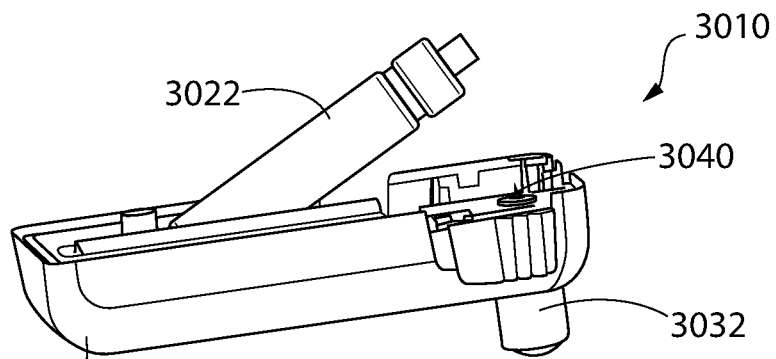
FIG. 30B is a trimetric view of the bottom of the fluid delivery device shown in FIG. 30A with the cartridge being inserted.
Figure 30C:
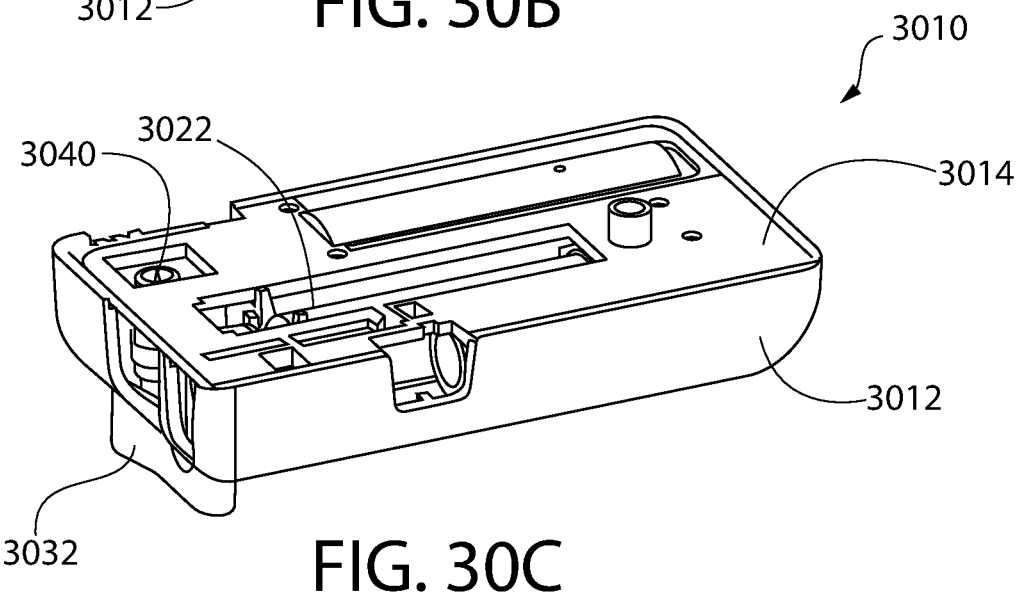
FIG. 30C is a reversed trimetric view of the bottom of the fluid delivery device shown in FIG. 30A with the cartridge inserted.
Figure 30D:
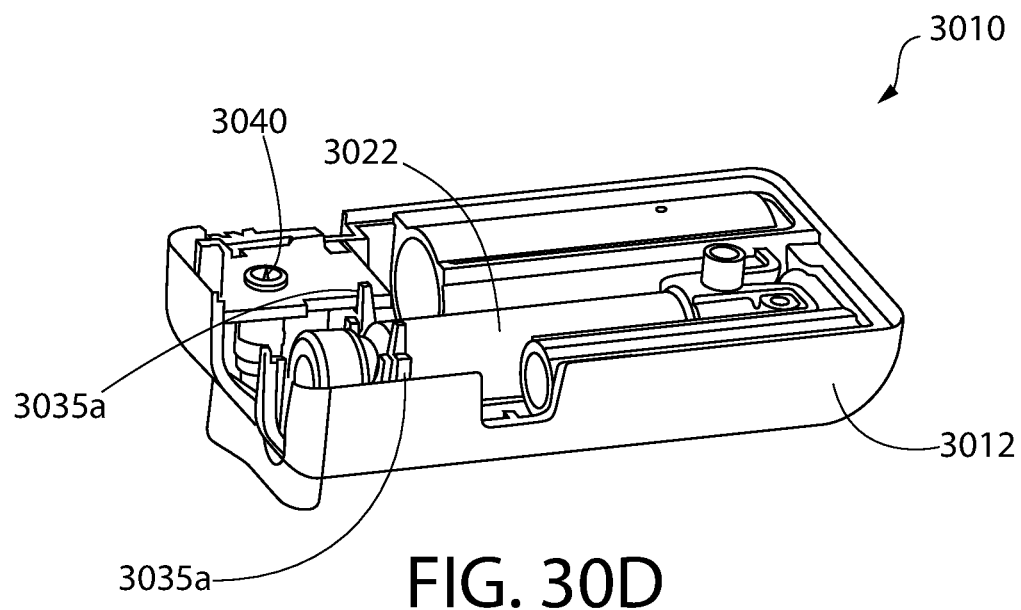
FIG. 30D is a reversed trimetric view of the bottom of the fluid delivery device shown in FIG. 30C with the cartridge inserted and the base plate removed for clarity.
Figure 30E:
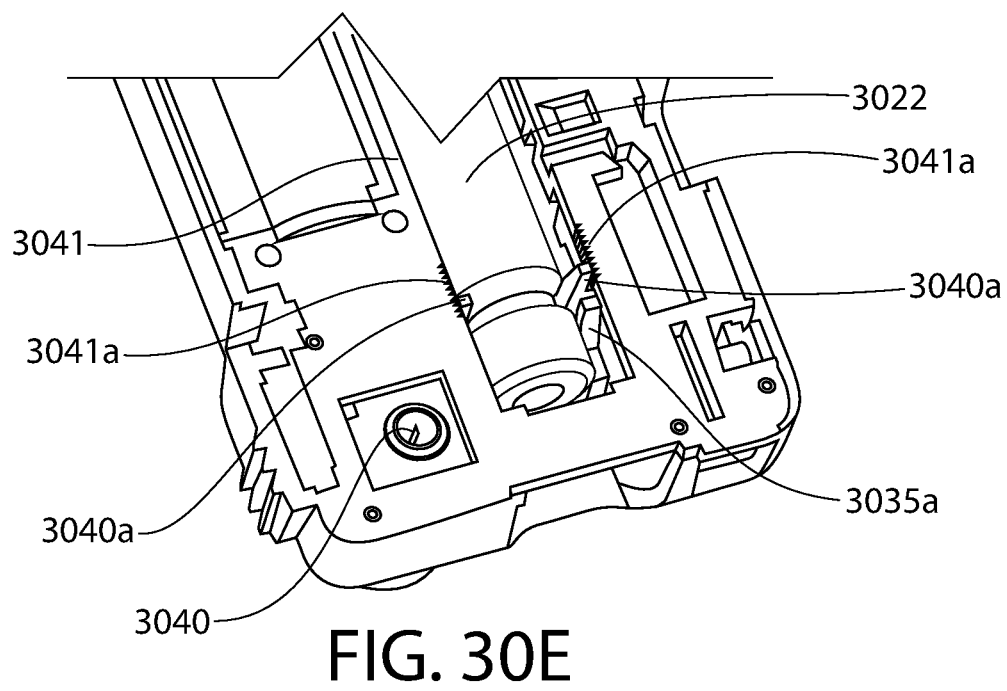
FIG. 30E is an enlarged partial trimetric view of the bottom of the fluid delivery device shown in FIG. 30C.
Figure 30F:
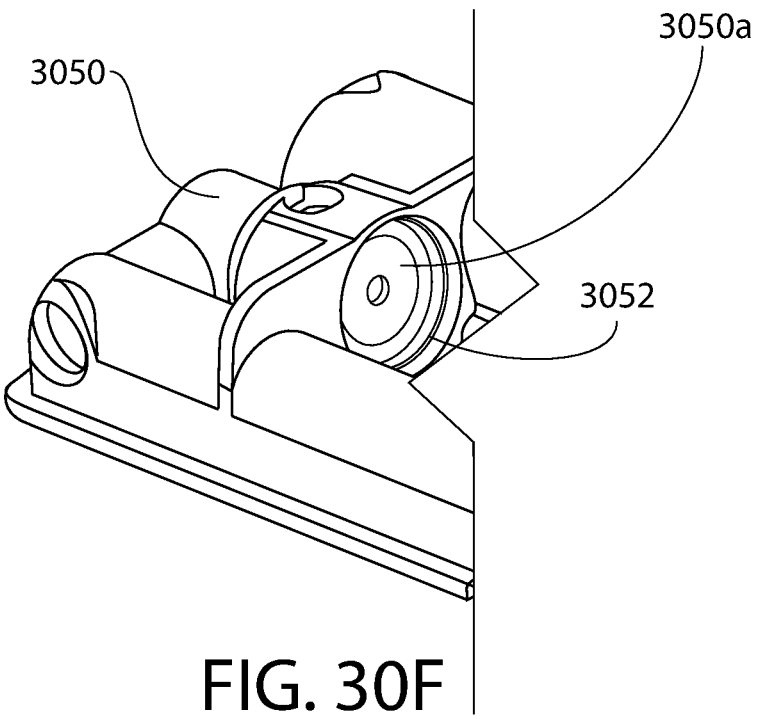
FIG. 30F is an enlarged partial trimetric view of the fluid delivery device shown in FIG. 30A showing the cartridge interface of the manifold.
Figure 30G:
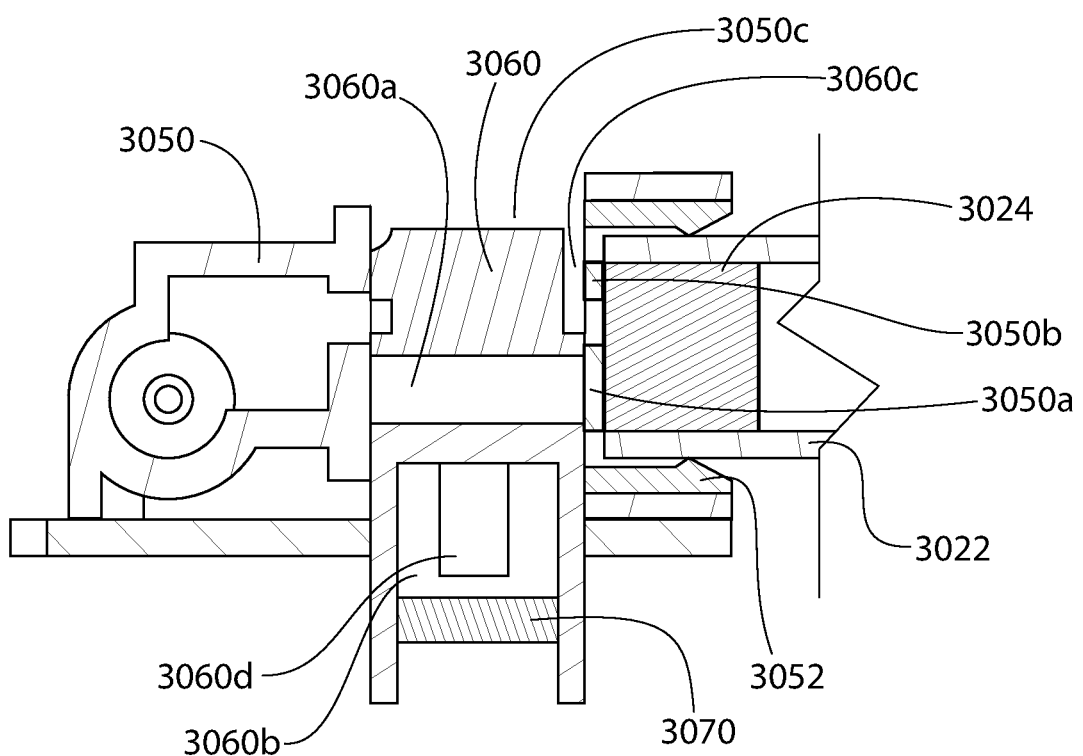
FIG. 30G is a partial cross sectional trimetric view of fluid delivery device shown in FIG. 30A showing the cartridge interface and oil trumpet seal when closed.
Figure 30H:
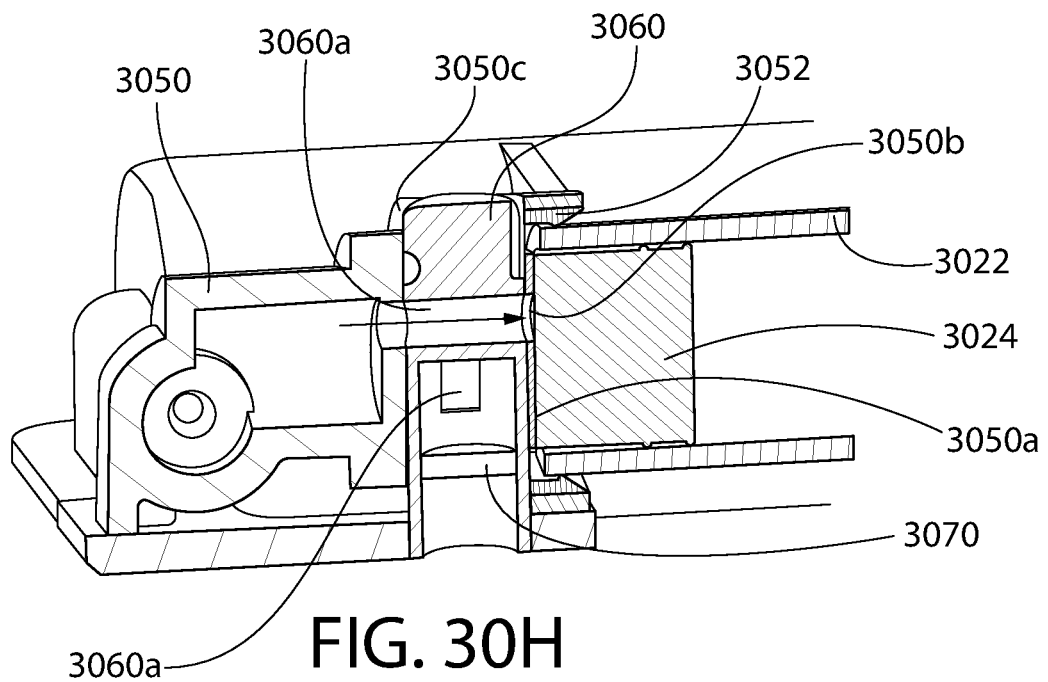
FIG. 30H is a partial cross sectional trimetric view of the fluid delivery device shown in FIG. 30G with the oil trumpet seal open.

In one embodiment, the fluid reservoir piston 3025 or a spacer proximal to the piston 3025 extends beyond or is essentially flush with the open end of the cartridge 3022. The cartridge is inserted into the device 3010 (FIG. 30A) through an opening in the housing base 3030 with the piston 3025 or spacer pressed up against the fluid manifold surface 3050a (FIGS. 30G and 30H). As an alternative, the piston 3025 or spacer is recessed inside of the cartridge 3022 and the fluid manifold surface 3050a extends out to come into close proximity or contact the piston 3025 or spacer. The cartridge 3022 septum end is pressed down into the device (FIG. 30B) and the cartridge neck 3022a is engaged by a retaining mechanism such as prongs 3040a. The prongs 3040a may be part of the floating needle mechanism 3040 so by engaging the cartridge neck 3022a, the needle mechanism 3040 is aligned with the septum seal end of the cartridge 3022 despite any length variation of the cartridge 3022.

In one embodiment, the fluid reservoir piston 3025 or spacer is pressed up against the fluid manifold surface 3050a by a spring element such as spring fingers 3035a part of the device cover 3035. This or these spring element(s) press the entire cartridge 3022 by pressing on the floating needle assembly prongs 3040a. In one embodiment, the spring element(s) press directly on the cartridge neck 3022a or on the cartridge septum end, such that the piston 3025 or spacer is axially forced up against the fluid manifold surface 3050a.

In one embodiment, where the fluid reservoir piston 3025 is moved by a fluid when the delivery device 3010 is activated, the cartridge 3022 is sealed to the fluid manifold 3050 by an eternal sliding seal 3052. This allows the fluid reservoir piston 3025 to be pressed against the fluid manifold surface 3050a reducing and preferably eliminating any gap that is compressible (e.g., an air gap or an additional elastic spacer) between the drive mechanism and the cartridge piston 3025.

In one embodiment, the cartridge piston 3025 or spacer is pressed up against the fluid manifold surface 3050a by a spring element 3035a as the cartridge 3022 is inserted into the delivery device 3010. When the cartridge 3022 is fully pressed into the floating needle assembly prongs 3040a, the prongs 3040a are spread as the gap between the prongs 3040a is slightly smaller than the cartridge neck 3022a. When the floating needle assembly prongs 3040a are spread, features such as teeth on their outer edges engage with mating features such as teeth 3030a on the inside edge of the base opening 3030. This engagement locks the axial movement of the cartridge 3022 as the floating needle assembly prongs 3040a and thus the cartridge neck 3022a can no longer move relative to the fluid manifold. Angling or otherwise shaping the mating features to pull the cartridge piston 3025 or spacer slightly away from the fluid manifold surface 3050a while locking the cartridge piston 3025 or spacer reduces and preferably eliminates any residual force from the spring elements 3035a that could affect the medicament delivery rate once the delivery needle 30400 penetrates the septum.

Figure 30I:
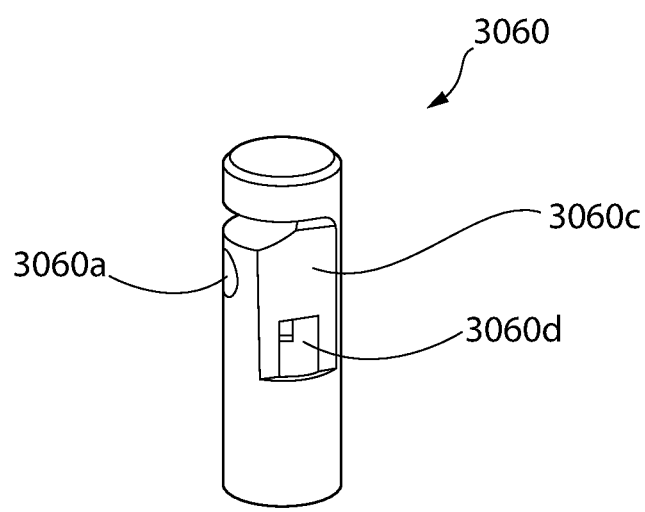
FIG. 30I is a trimetric view of the valve stem of the fluid delivery device shown in FIG. 30A.

Referring to FIGS. 30G-30H, in one embodiment, where the fluid reservoir piston 3025 is moved by a fluid when the delivery device 3010 is activated, the fluid is contained in the fluid manifold 3050 by a trumpet valve 3060. The trumpet valve stem can slide or rotate with similar effects but will be described here as translations, rotation only requires a change in passage positions and will be described more specifically later. The trumpet valve 3060 slides in a tight fitting cylinder 3050c in the manifold 3050. The manifold 3050 has a cross path 3050b that connects on one side to the interior of the manifold 3050 and continues to the fluid manifold surface 3050a. The trumpet valve 3060 has a passage 3060a that, prevents the flow of fluid from inside the manifold 3050 to the back of the fluid reservoir piston 3025 when not aligned with cross path 3050b (FIG. 30G). In one embodiment, the trumpet valve 3060 has a path or recess 3060c allowing the opening in the manifold 3050a to vent to atmosphere when the passage 3060a is not aligned with cross path 3050b. This prevents air pressure build up when the cartridge 3010 is inserted. In one embodiment, when the trumpet valve 3060 is moved or rotated such that trumpet valve passage 3060a is aligned with cross path 3050b fluid can pass freely from inside of the fluid manifold 3050 to the back of the fluid reservoir piston 3025 and the air vent path 3060c is sealed (FIG. 30I). In one embodiment, the trumpet valve passage 3060a is filled with drive fluid prior to cartridge insertion to minimize any air in the drive fluid path.

To prevent the hydraulic fluid from leaking through the hydraulic fluid reservoir before the fluid reservoir is inserted into the fluid delivery device, a hydraulic fluid seal may be provided. In one embodiment, where the fluid reservoir piston 3025 is moved by a drive fluid when the delivery device 3010 is activated, the drive fluid is contained in the fluid manifold 3050 by a trumpet valve 3060 acting as the hydraulic fluid seal and an additional accumulator chamber 3060b is provided to allow the thermal expansion and contraction of the drive fluid prior to inserting cartridge 3022. The chamber 3060b is located within the trumpet valve 3060 and is interconnected with the fluid manifold 3050 by a path around the trumpet valve stem 3060c, through opening 3060d and into the chamber 3060b. In one embodiment chamber 3060b is located within the trumpet valve 3060 and is interconnected with the fluid manifold 3050 by a direct path. In one embodiment, there is a piston 3070 in the chamber 3060b to contain the drive fluid but allow the chamber size to change as the drive fluid expands and contracts. In one embodiment, the chamber 3060b is sealed but there is a compressible or deformable element in the chamber to absorb the volume change of the drive fluid. In one embodiment, the chamber 3060b is sealed by a membrane. In one embodiment, the chamber is not a part of the trumpet valve 3060, but is interconnected by 3060c when passage 3060a is not aligned with cross path 3050b. In one embodiment there are one or more elastomeric components that are used to create seals between the valve components.

In one embodiment, the act of inserting the fluid reservoir into the fluid delivery device causes the hydraulic fluid seal to be opened. In some embodiments, the hydraulic fluid seal is a floating seal or a foil seal that is punctured similar to the embodiments disclosed in U.S. Patent Application Publication No. 2011/0306929 which is hereby incorporated by reference in its entirety. The hydraulic fluid seal may include a mechanical seal valve.

Referring to FIGS. 31A-31H, another exemplary embodiment of a fluid delivery device 3110 is shown. The hydraulic fluid seal may include a mechanical seal valve such as a rotating stem 3160. The stem 3160 may include a fluid path 3160a that is rotated to fluidly selectively couple the hydraulic fluid reservoir 3140a with the piston 3124 (see FIG. 31C) of the cartridge 3122. The stem 3160 may be located in a socket 3150 that is fluidly connected to the hydraulic fluid manifold 3140. The socket 3150 may be integral with the hydraulic fluid manifold 3140. In other embodiments, the socket 3150 is a separate component that is attached to the manifold 3140.

The stem 3160 may have one or more fluid paths 3160a that enter one side of the stem 3160 and leave the other. In its initial position, the stem 3160 may be positioned so that the fluid path 3160a is not aligned with the fluid path 3150a through the socket 3150 thus blocking flow of the hydraulic fluid out of the hydraulic fluid reservoir 3140a (see FIG. 31C). In the activated position, the stem 3160 may be rotated to a position where the fluid path 3160a in the stem 3160 is essentially aligned or fluidly coupled with the fluid paths 3150a through the socket allowing the hydraulic fluid to flow out of the hydraulic fluid reservoir 3140a (see FIG. 31C). In one embodiment, the fluid path 3160a may be open to the hydraulic fluid reservoir 3140a when closed to the piston 3124 (see FIG. 31F). In one embodiment, the fluid path 3160a may be closed to the hydraulic fluid reservoir 3140 when closed to the piston 3124 (see FIG. 31G-I).

Initially, stem 3160 may be rotated such that fluid path 3160a is not aligned with the fluid path 3150a through the socket thus blocking flow of the hydraulic fluid. The cartridge 3122, which is pre-filled with a fluid, is then inserted into the fluid delivery device 3110 and the stem 3160 is rotated to fluidly couple the fluid path 3160a with the hydraulic fluid reservoir 3140a.

In one embodiment the stem hydraulic fluid passage 3160a is filled with hydraulic fluid prior to cartridge insertion and prior to rotation.

Figure 31A:
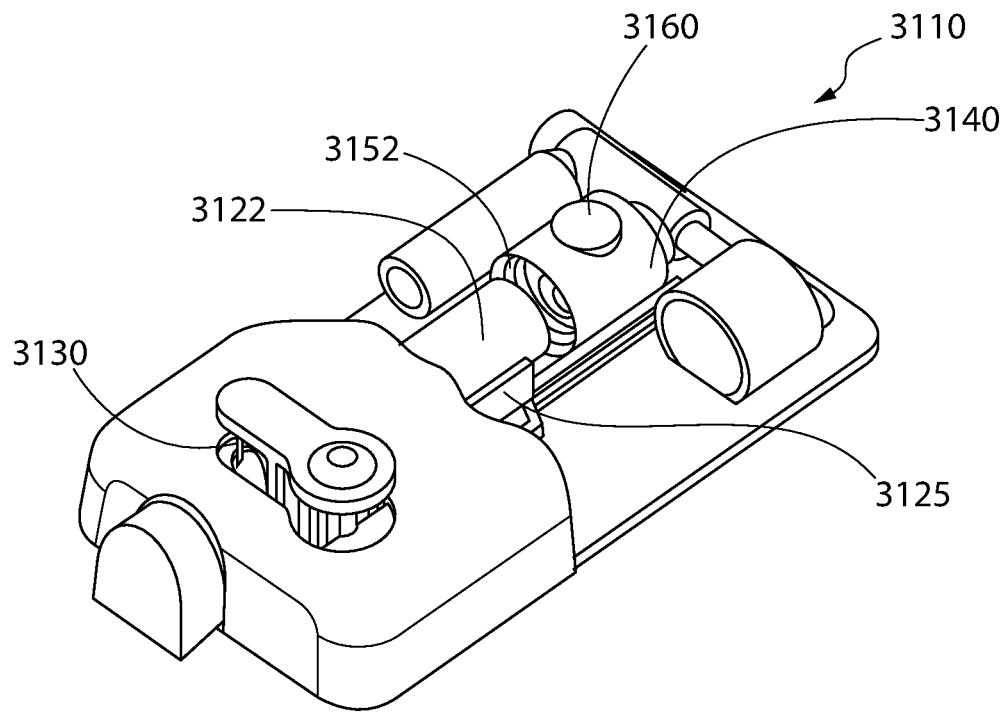
FIG. 31A is a trimetric view of a fluid delivery device in accordance with an exemplary embodiment of the present invention with the cover partially cut away, the fluid reservoir partially inserted and the hydraulic fluid path closed.
Figure 31B:
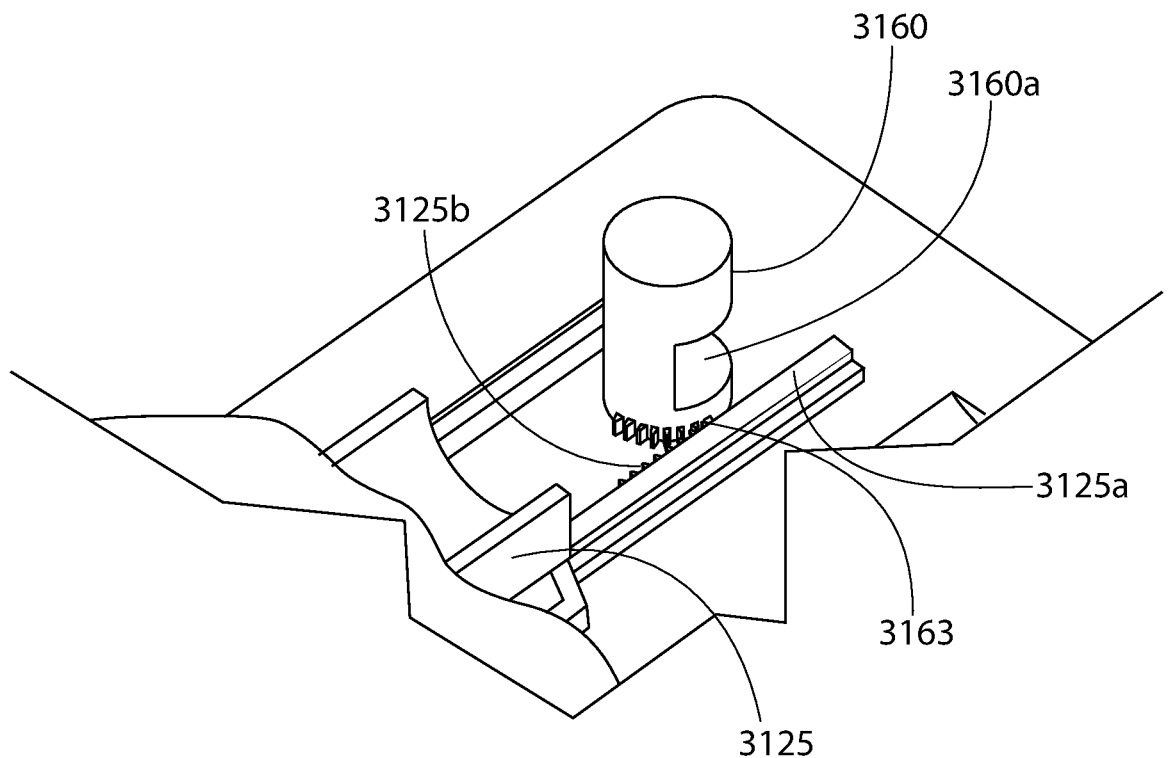
FIG. 31B is a trimetric detail view of a fluid delivery device shown in FIG. 31A with the fluid manifold, fluid reservoir, seal and cover removed for clarity.
Figure 31C:
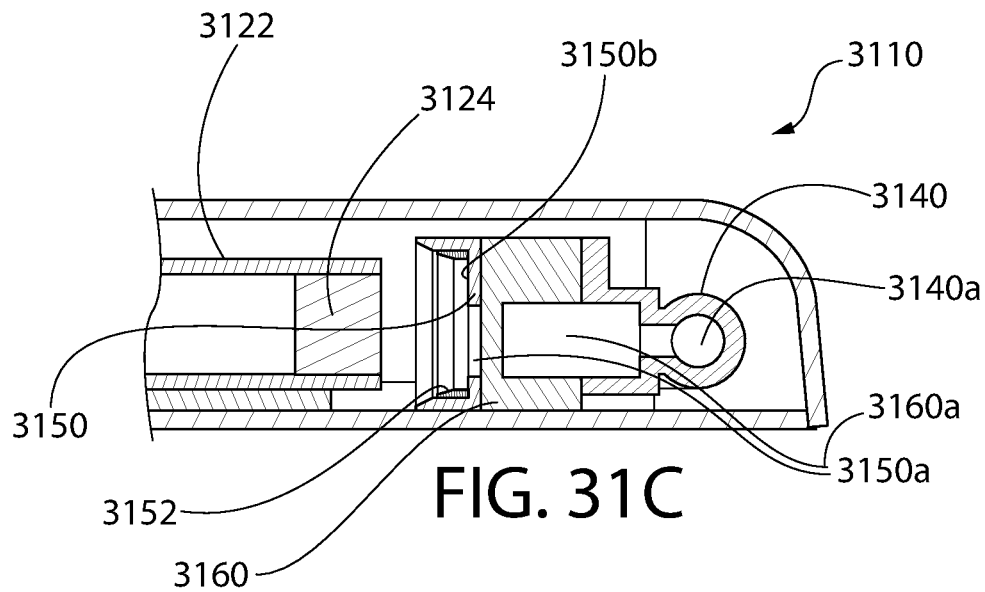
FIG. 31C is a partial cross section view of a fluid delivery device shown in FIG. 31A with the fluid reservoir partially inserted, the hydraulic fluid path closed, and an accumulation chamber connected.
Figure 31D:
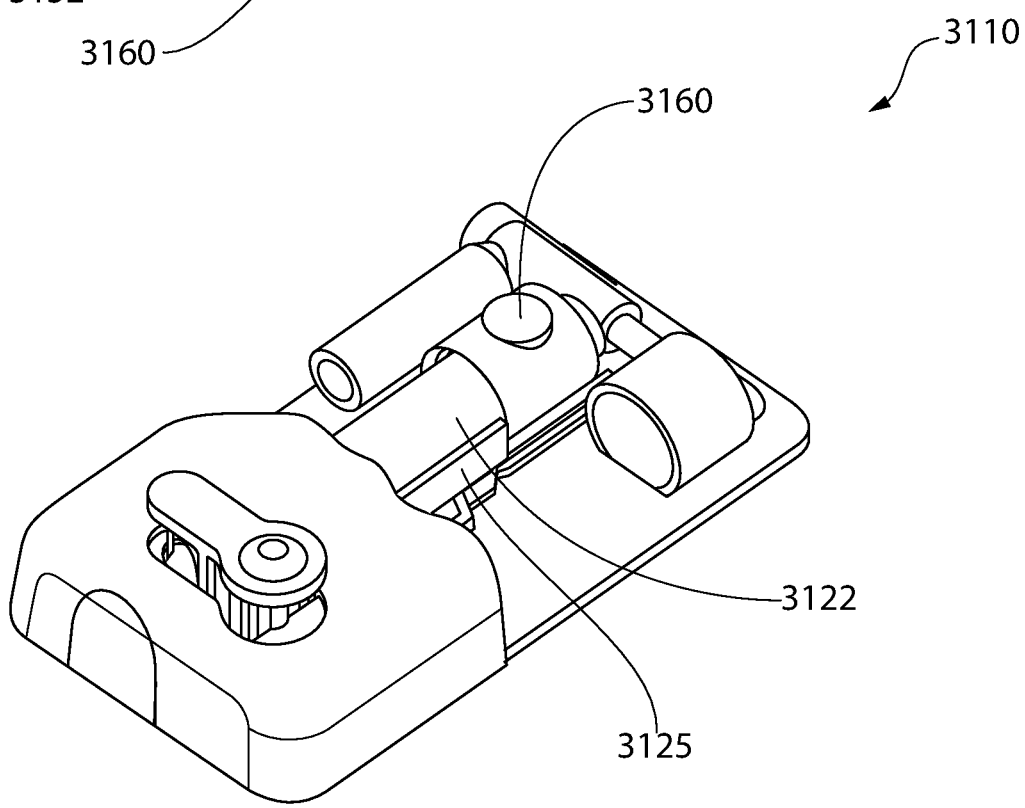
FIG. 31D is a trimetric view of a fluid delivery device shown in FIG. 31A with the cover partially cut away, the fluid reservoir fully inserted, and the hydraulic fluid path open.
Figure 31E:
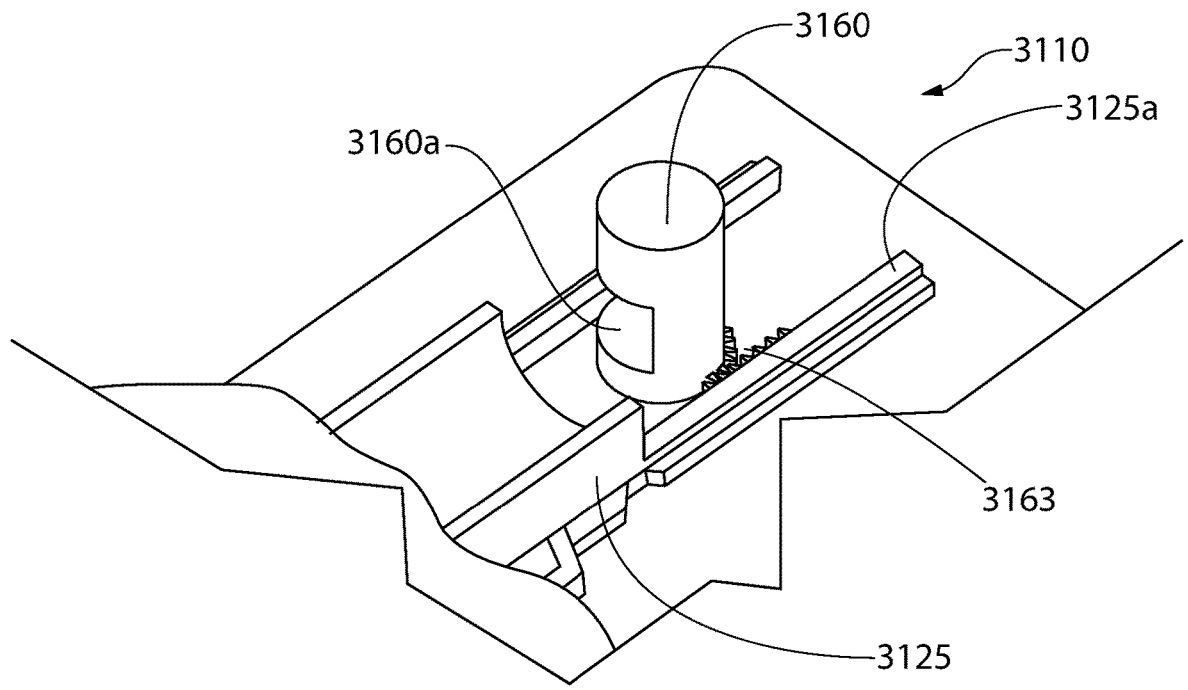
FIG. 31E is a trimetric detail view of a fluid delivery device shown in FIG. 31D with the fluid manifold, fluid reservoir, seal and cover removed for clarity.
Figure 31F:
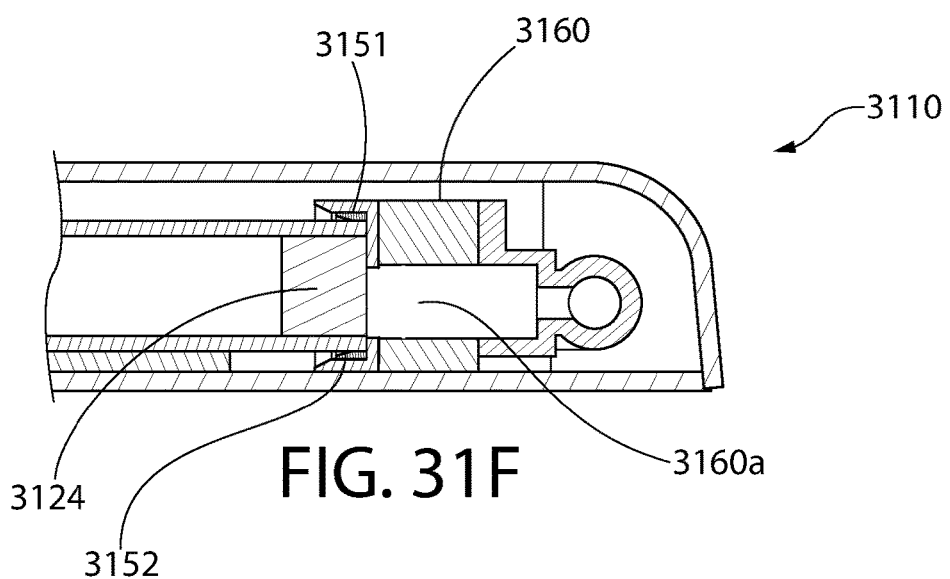
FIG. 31F is a partial cross section view of a fluid delivery device shown in FIG. 31D with the fluid reservoir fully inserted, and the hydraulic fluid path open.
Figure 31G:
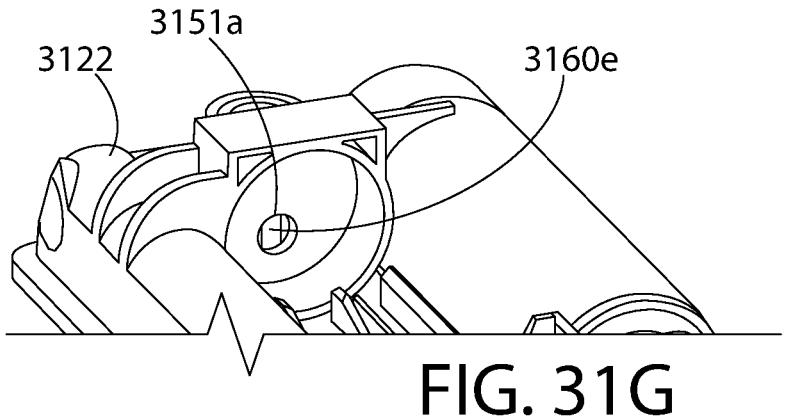
FIG. 31G is a partial trimetric view of a fluid delivery device shown in FIG. 31A with the hydraulic fluid path closed.
Figure 31H:
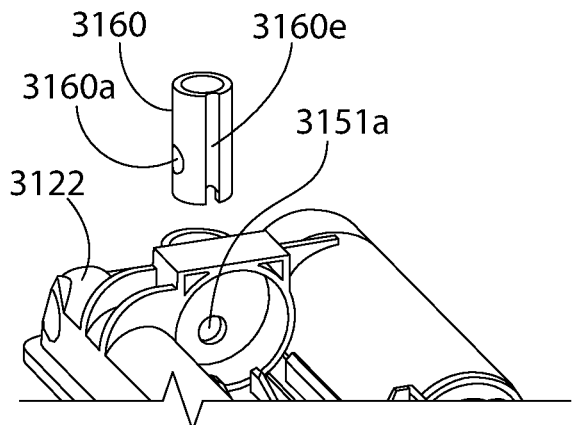
FIG. 31H is a partial trimetric exploded view of a fluid delivery device shown in FIG. 31A with the stem above the manifold.
Figure 31I:
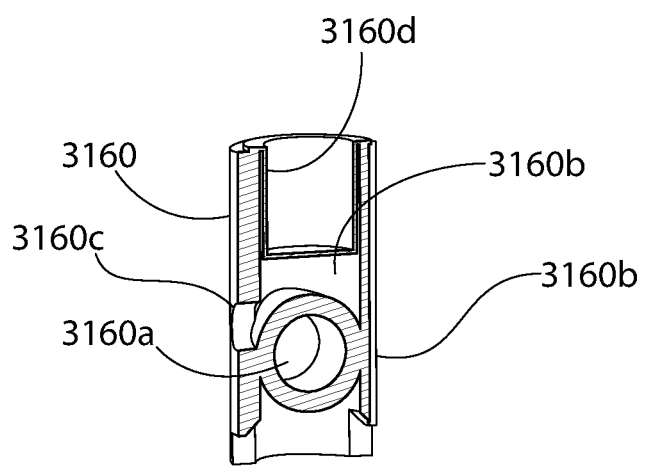
FIG. 31I is a trimetric section view of the stem of the fluid delivery device shown in FIG. 31A.

Referring to FIG. 31I, in one embodiment, the stem 3160 may contain a sealed but deformable chamber 3160b that is interconnected with the hydraulic fluid in the initial sealed position through passage 3160c. This chamber would be disconnected from the hydraulic fluid by the rotation of the stem. The chamber 3160c is deformable through the flexing of membrane 3060d or the motion of a piston in the same space. In one embodiment it is possible to have both passage 3160c and passage 3106a connected from the hydraulic fluid simultaneously.

Referring to FIG. 31A, in one embodiment, the cartridge 3122 is inserted into the fluid delivery device 3110 through an opening in one end of the fluid delivery device 3110, piston end first. In one embodiment, the cartridge 3122 is inserted into the fluid delivery device 3110 through an opening in one side of the fluid delivery device 3110. In one embodiment, the cartridge 3122 is inserted into the fluid delivery device 3110 through an opening in the body side of the fluid delivery device 3110. In one embodiment, the cartridge 3122 is inserted into the fluid delivery device 3110 through an opening in the side opposite the body side of the fluid delivery device 3110.

Referring to FIG. 31B, in one embodiment, the act of inserting cartridge 3122 into the fluid delivery device 3110 may cause the stem 3160 to rotate open. In other embodiments, the stem 3160 is manually opened (e.g., the user twists a component coupled to the stem 3160) or opened upon conducting a second action, such as closing a cartridge 3122 retaining device or deploying the needle.

The cartridge 3122 may be coupled to a sliding drawer 3125 that guides the cartridge 3122 to its final position where the fluid cartridge 3122 seals with the output fluid path 3150a of the socket. Moving the drawer 3125 to its final position may act to rotate the stem 3160 from its initial or sealed position to its activated or open position. In one embodiment, the sliding drawer 3125 has a drawer feature 3125a that interacts with the stem 3160 to rotate the stem 3160 from its initial position to its activated position. In one embodiment, the drawer feature 3125a is a toothed rack and the stem 3160 has a toothed pinion 3163 that interact to move the stem 3160 from its initial position to its activated position when the sliding drawer 3125 is moved to its final position. In one embodiment, the stem 3160 has a lever that a drawer feature 3125a pushes on when the drawer 3125 is moved to its final position moving the stem 3160 from its initial position to its activated position.

The fluid reservoir piston 3124 may be moved by the hydraulic fluid when the fluid delivery device 3110 is activated. The cartridge 3122 may be sealed to a socket 3150 of the hydraulic fluid manifold 3140 by a sliding seal 3152. This may allow the fluid reservoir piston 3124 to be pressed against the hydraulic fluid manifold surface 3150b eliminating any air gap between the reservoir piston 3124 and the hydraulic fluid.

As similarly shown in FIGS. 31G-31I, in one embodiment, the stem 3160 has a path or recess 3160e allowing the opening in the socket 3150a to vent to atmosphere when the passage 3160a is not aligned with cross path 3051a. This prevents air pressure build up when the cartridge 3122 is inserted and enters the socket 3150a.

In one embodiment, when the stem 3160 is rotated such that the fluid path 3160a is aligned with the socket fluid path 3150a within the socket 3150 and fluid can pass freely from inside of the hydraulic fluid manifold 3140 to the back of the fluid reservoir piston 3124, the air vent path from the socket element 3160e is sealed. In one embodiment, the stem fluid path 3160a is filled with hydraulic fluid prior to cartridge 3122 insertion to eliminate or at least minimize any air in the drive fluid path.

In one embodiment, cartridge 3122 contains two or more fluid reservoirs. Each of the two or more fluid reservoirs may include a piston. One or more of the pistons in the fluid reservoirs may be moved under the influence of a drive fluid that is stored within a drive fluid reservoir within or part of the housing.

Figure 32A:
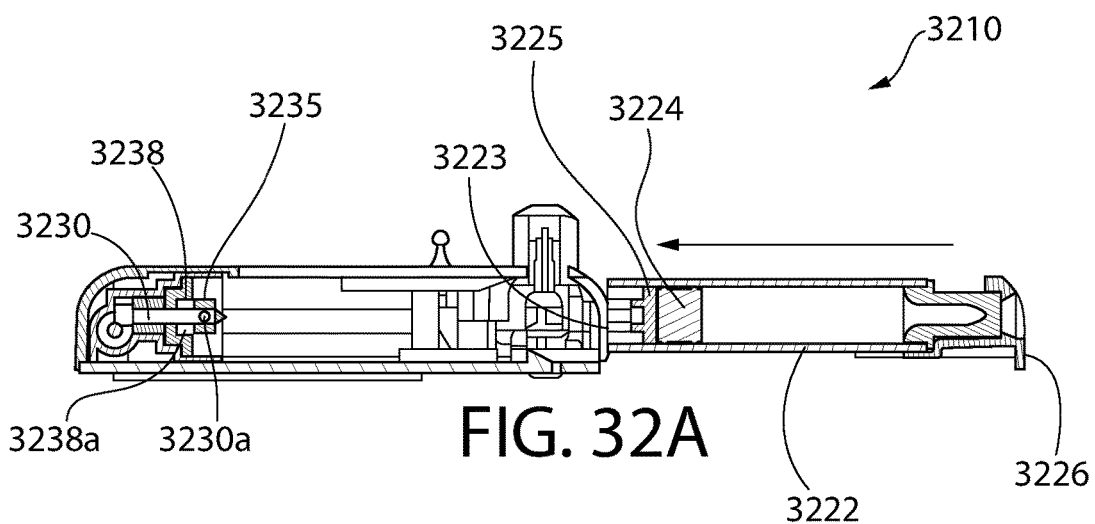
FIG. 32A is a cross sectional view of a fluid delivery device in accordance with an exemplary embodiment of the present invention with the cartridge ready to be inserted.
Figure 32B:
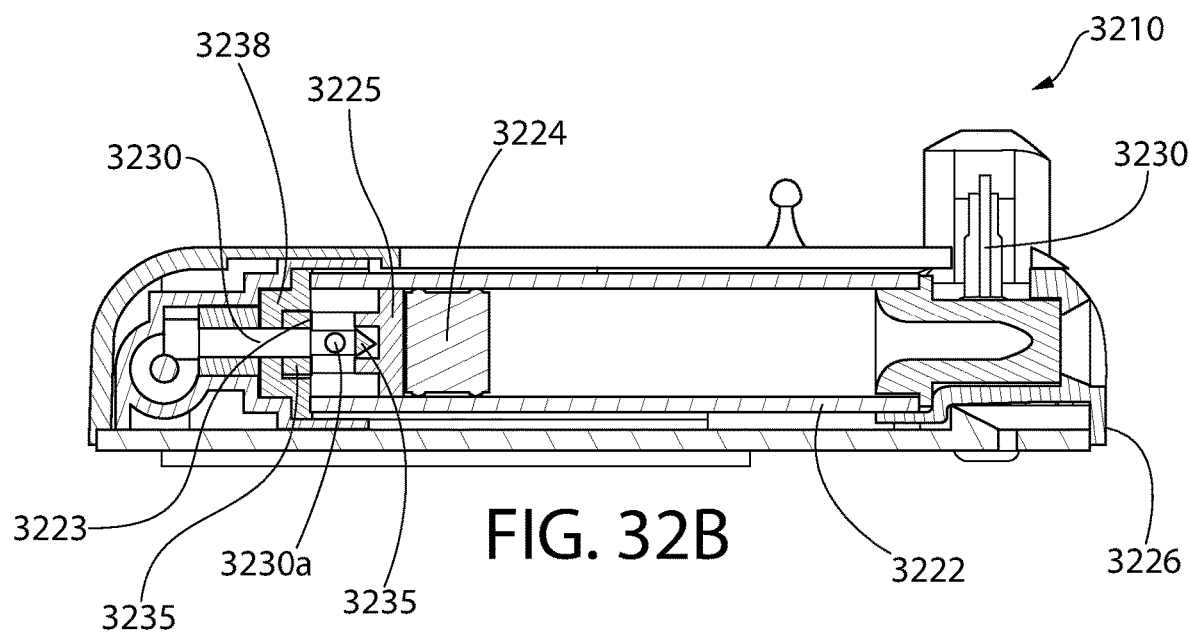
FIG. 32B is a cross sectional view of the fluid delivery device shown in FIG. 32A with the cartridge inserted.

Referring to FIGS. 32A-32B, in one embodiment where the piston 3224 is moved by a drive fluid when the delivery device 3210 is activated, the cartridge 3222 is shown in its initial insertion position. The cartridge 3222 is inserted essentially axially into delivery device 3210, in the direction of the arrow shown. In one embodiment the cartridge 3222 is retained in place by features in the cartridge cap 3226. During insertion, the fluid transfer needle 3230 will penetrate the cartridge seal 3223. In one embodiment, the stopper 3225 in conjunction with seal 3223 will relocate the needle dam 3235, exposing the drive fluid transfer opening 3230a in the fluid transfer needle 3230, (FIG. 32B), into the receiver cavity 3238a located in the face seal 3238. Air vent holes in the base of the recess in face seal 3238 will allow the air to be vacated from the receiver cavity 3238a until needle dam 235 is pressed against the base of the recess in face seal 238 sealing them. In one embodiment, the cavity around the outer side of stopper 3225 will be filled with drive fluid (e.g., any incompressible fluid) minimizing the volume of air captured. The cartridge 3222 is shown in its captured position within the pump assembly 3210 (FIG. 32B). The needle dam 3235 is shown in its active position exposing the fluid transfer opening 3230a in the fluid transfer needle 3230.

Figure 33A:
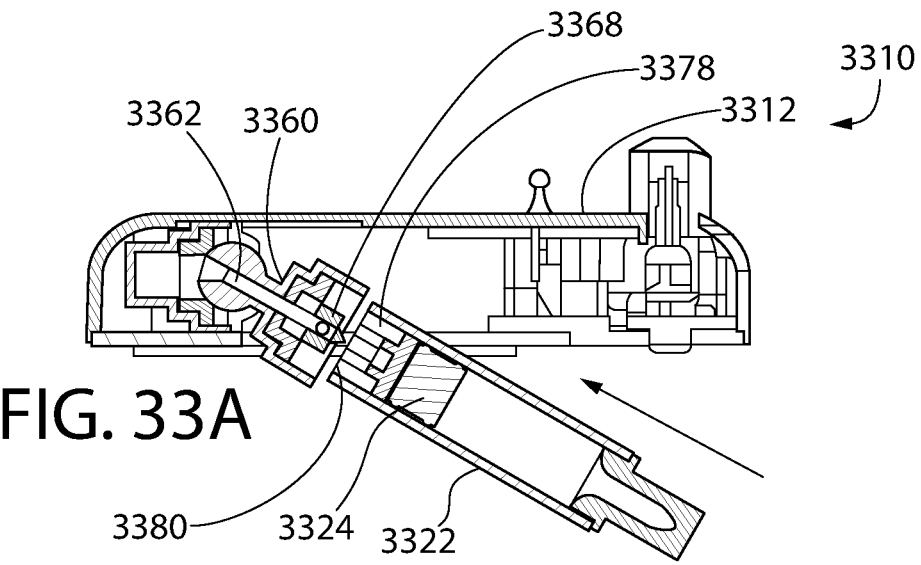
FIG. 33A is a cross sectional view of a fluid delivery device in accordance with an exemplary embodiment of the present invention with the cartridge ready to be inserted.
Figure 33B:
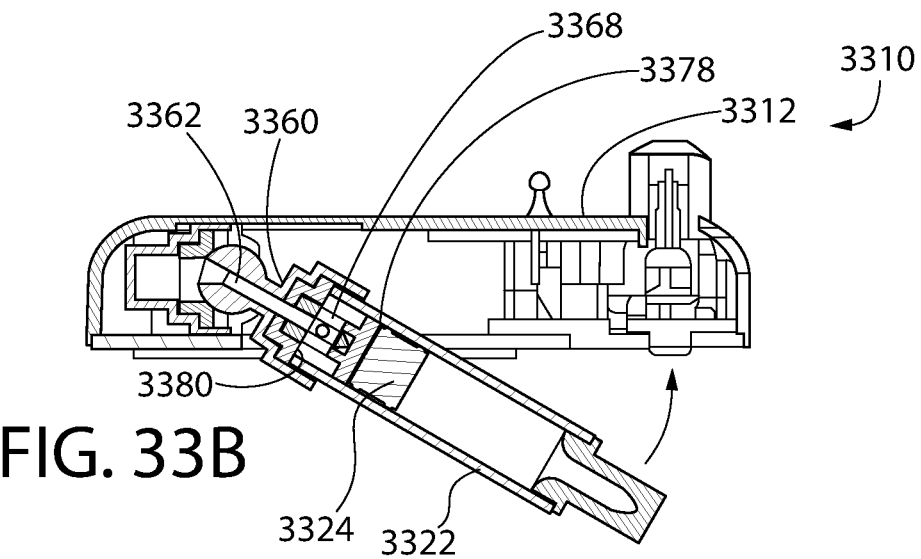
FIG. 33B is a cross sectional view of a fluid delivery device shown in FIG. 33A with the cartridge when inserted but not yet rotated into the housing.
Figure 33C:
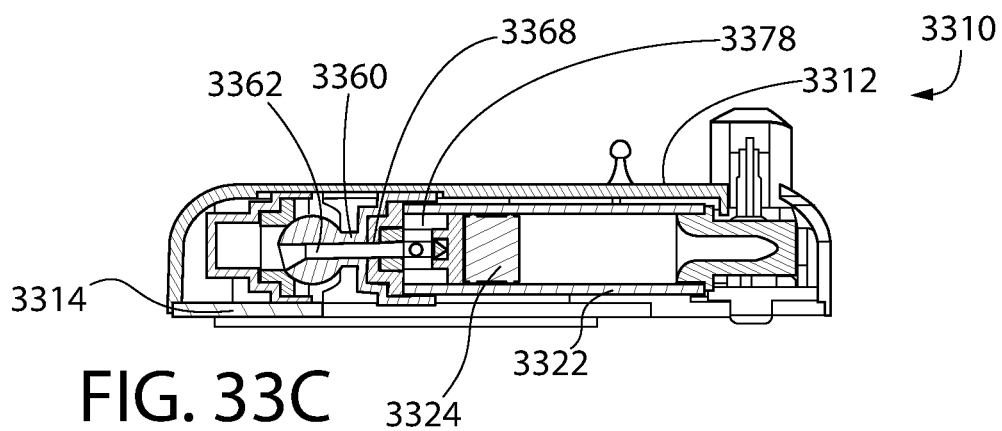
FIG. 33C is a cross sectional view of a fluid delivery device shown in FIG. 33A with the cartridge inserted and rotated into the housing.

Referring to FIGS. 33A-33C, in one embodiment, where a fluid reservoir piston 3324 is moved by a drive fluid when the delivery device 3310 is activated, an end of the cartridge 3322 is inserted and coupled to the manifold and then rotated into position. The delivery device 3310 is shown in its initial insertion position in FIG. 33A with the cartridge 3322 in its initial insertion position. In one embodiment, the cartridge 3322 is inserted into a ball joint receiver 3360, at an acute angle relative to the bottom surface of the housing (e.g., in the direction of the arrow shown in FIG. 33A), until cartridge 3322 is retained in place. In one embodiment, during, and as a result of, this motion, the fluid transfer needle 3362 will penetrate the seal 3380. In one embodiment, the stopper 3378 in conjunction with seal 3380 will relocate the needle dam 3368, exposing the fluid transfer opening in the fluid transfer needle 3362, (FIG. 33B), into the receiver cavity 3365a located in the seal 3365. Air vents in the face seal 3365 will allow the air to be vacated from the receiver cavity. In one embodiment, space around the outer side of stopper 3378 will be filled with a drive fluid minimizing the volume of air captured.

In one embodiment, the cartridge 3322 is rotated into the housing of the device (FIG. 33C). When the cartridge 3322 is in its final position, clips in the device cover 3312 or device base 3357 retain the cartridge 3322 in position.

Figure 34A:
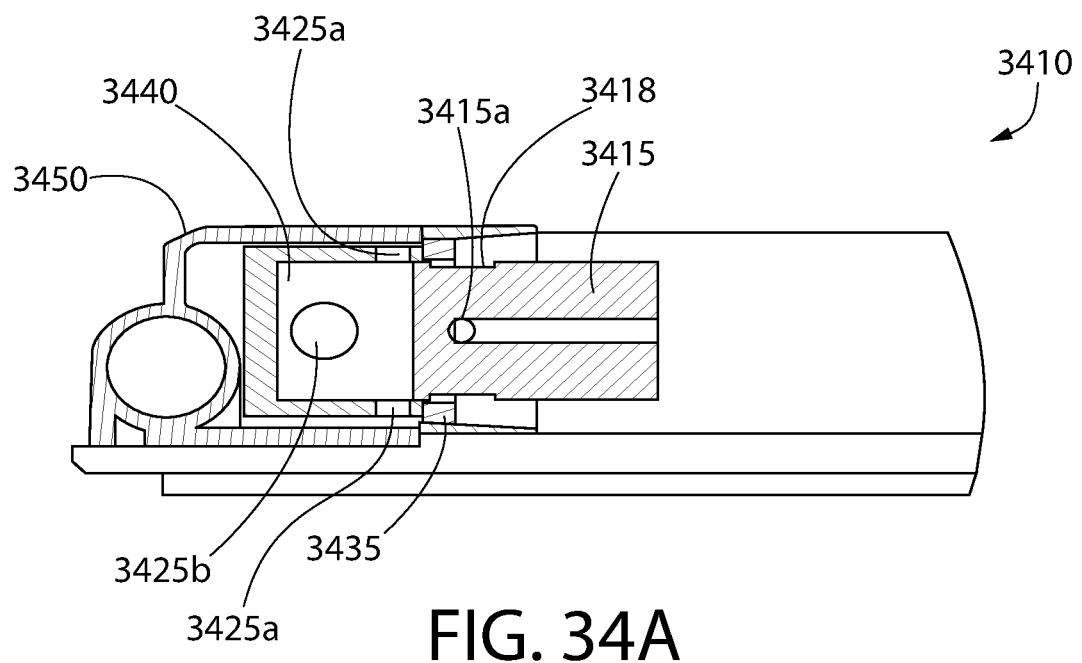
FIG. 34A is a partial cross sectional view of a fluid delivery device in accordance with an exemplary embodiment of the present invention with no cartridge inserted and the accumulator fluidly connected.
Figure 34B:
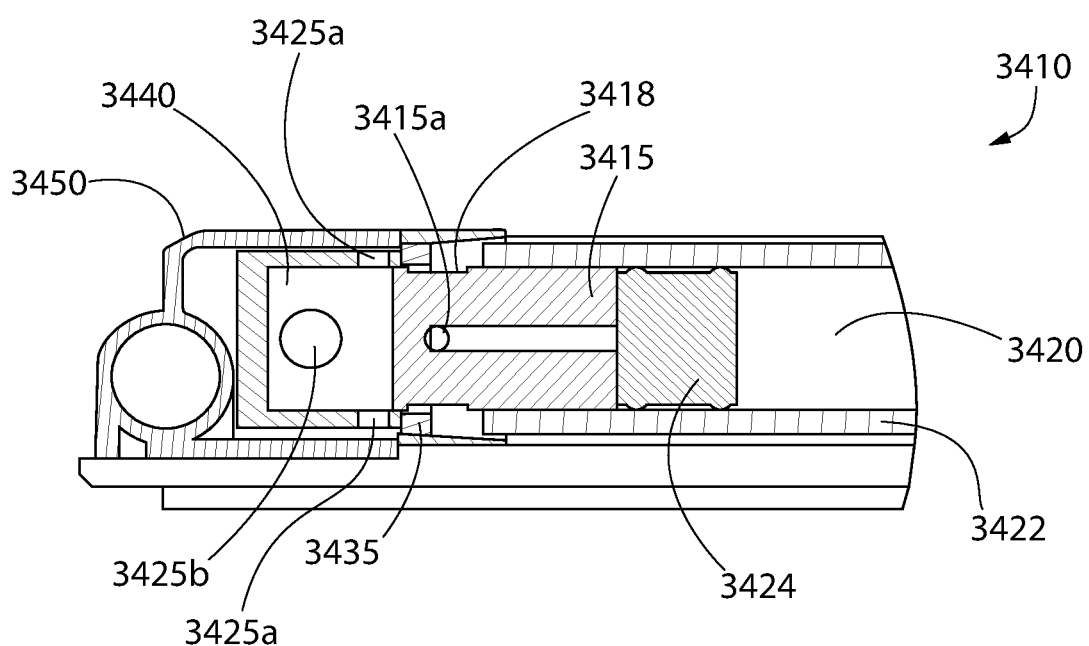
FIG. 34B is a partial cross sectional view of the fluid delivery device shown in FIG. 34A with the cartridge partially inserted.
Figure 34C:
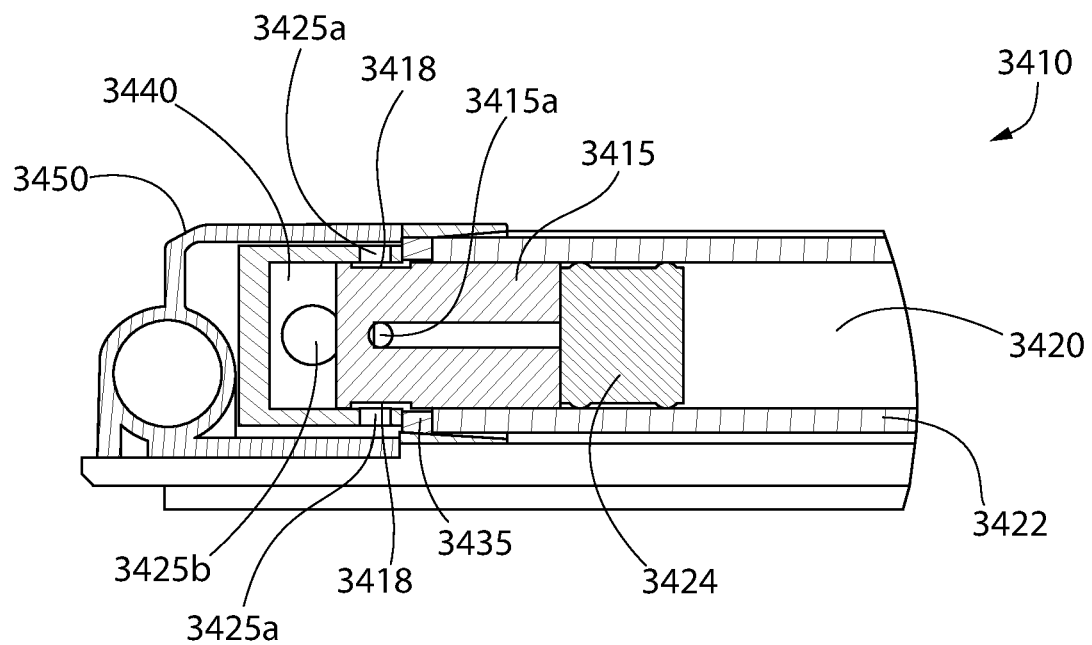
FIG. 34C is a partial cross sectional view of the fluid delivery device shown in FIG. 34A with the cartridge fully inserted and the accumulator isolated.
Figure 35A:
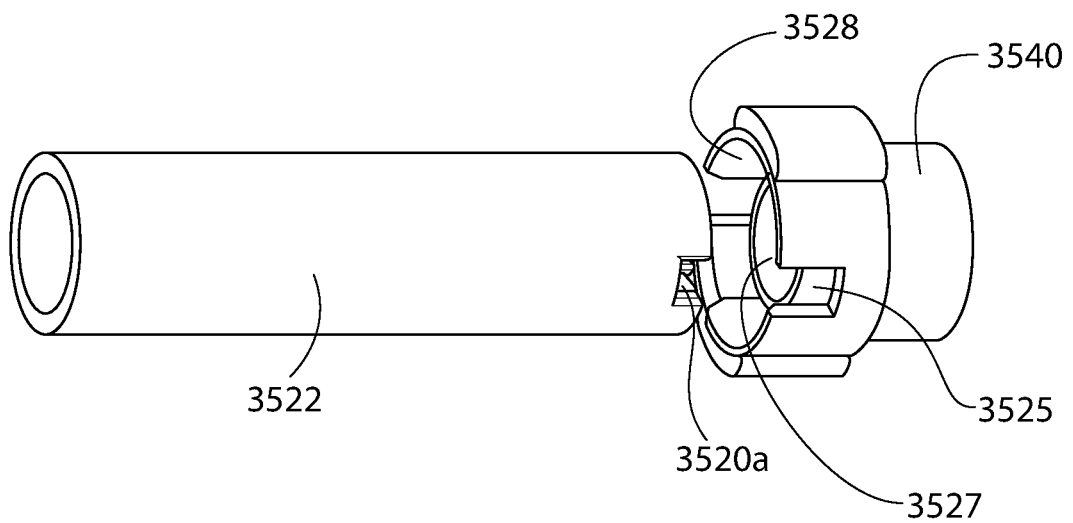
FIG. 35A is a trimetric view of a cartridge and manifold of a fluid delivery device in accordance with an exemplary embodiment of the present invention with the cartridge ready to be inserted.
Figure 35B:
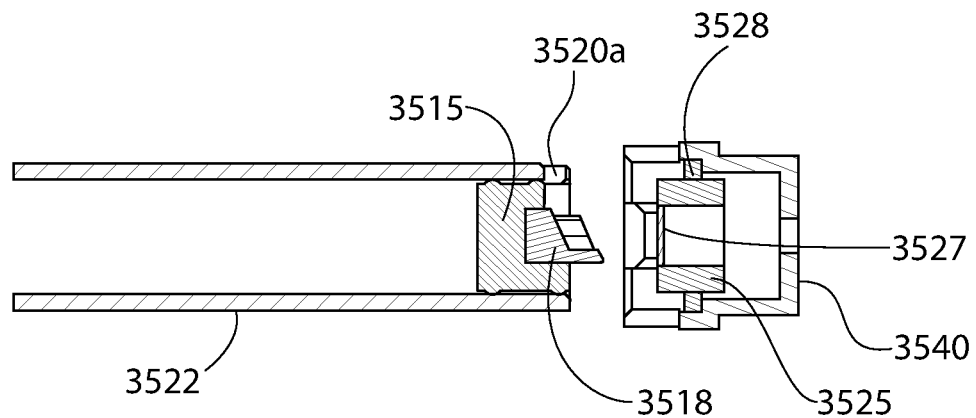
FIG. 35B is a cross section side view of the cartridge and manifold shown in FIG. 35A with the cartridge ready to be inserted.
Figure 35C:
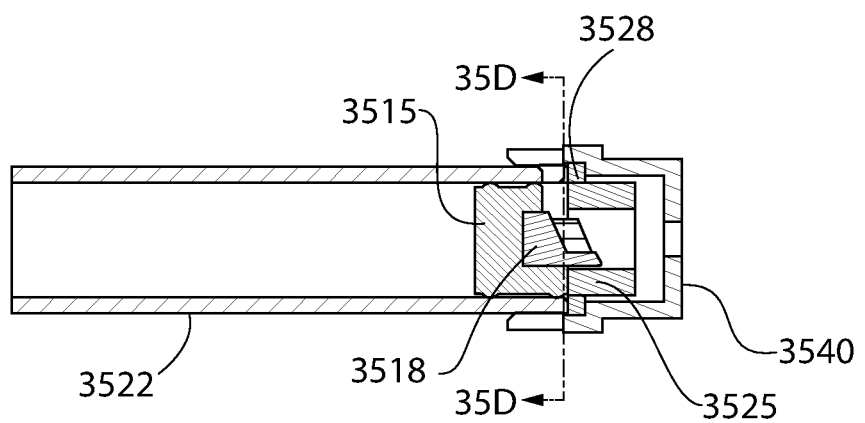
FIG. 35C is a cross section side view of the cartridge and manifold shown in FIG. 35A with the cartridge inserted.
Figure 35D:
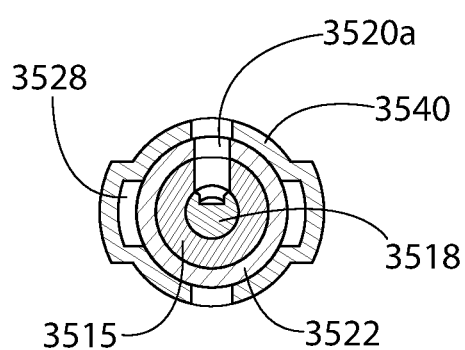
FIG. 35D is a cross section end view of the cartridge and manifold shown in FIG. 35C.
Figure 35E:
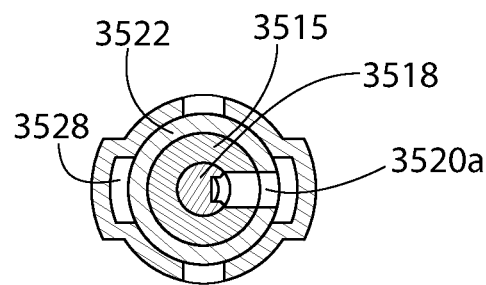
FIG. 35E is a cross section end view of the cartridge and manifold shown in FIG. 35C with the cartridge inserted and rotated.

Referring to FIGS. 34A-34C, in one embodiment, a linearly actuated valve, actuated by the insertion of the cartridge 3420 into the delivery device 3410, opens flow to the cartridge 3420 while shutting off communication to a storage temperature compensation system. The stem 3415 is inserted into an opening of a valve seat 3425. The stem 3415 inserted into the top of the valve seat 3425 seals the drive system during storage, before use. The internal volume of the manifold 3430 fluidly communicates to an internal chamber 3440 of the valve body 3425 through ports 3425a. During storage these ports can communicate to the storage temperature compensation system through port 3425b (see FIG. 34A).

When the cartridge 3420 is installed, the cartridge piston 3445 pushes on the valve stem 3415. As the valve stem 3415 moves into the valve body 3425, ports 3425a are isolated from the storage temperature compensation system and allowed to communicate with the internal path 3415a of the valve stem 3415, though annulus 3418. The excess drive oil from chamber 3440 is pushed into the storage temperature compensation system (see FIG. 34B). In one embodiment, alternately, the storage temperature compensation system, could be located within the stem, and includes air.

Once the cartridge 3420 is seated completely into the delivery device 3410 (FIG. 34C) the end 3443 of the cartridge 3420 seals against a face seal 3435. This allows for oil flowing from the manifold through ports 3425a and annulus 3418 and up the internal passage of the valve stem 3415a to displace the cartridge piston 3445 and not leak out of the system.

Referring to FIGS. 35A-35E, in one embodiment, cartridge 3520 has a notch 3520a in the leading edge of the wall. This notch 3520a lines up substantially with a channel in the cartridge piston 3515, and a channel in the rigid spike 3518. In one embodiment, when the cartridge 3520 is initially inserted, the spike 3518 will pierce the foil 3527 adhered to the face of the accumulator piston 3525. This allows the drive fluid to flow into the channel in the spike 3518 and the piston, and out through the notch 3520a in the cartridge 3520, as the accumulator piston is pushed in. In one embodiment, the outer diameter of the cartridge 3520 slides against the "wings" of the face seal 3528, pushing the accumulator piston 3525 in until the end of the cartridge 3520 compresses the face seal against the manifold 3540.

In one embodiment, after the cartridge 3520 is inserted, and the accumulator piston 3525 is pushed back until the end of the cartridge 3520 is making a seal axially against the face seal 3528 and there is a path for excess working fluid to leave the manifold through the notch 3520a in the cartridge 3520.

In one embodiment, after the cartridge has been inserted, it can be rotated such that the notch in the cartridge 3520 is covered by one of the "wings" on the face seal 3528, blocking the path for the working fluid to leave the manifold, and sealing the cartridge 3520.

In one embodiment, alternately, the notch 3520a in the leading edge of the wall of the cartridge could be a hole in the wall of the cartridge, with the leading edge un-interrupted. In one embodiment, alternately, the spike 3518 could be integral with the cartridge piston 3515.

Referring to FIGS. 36A-36E, in one embodiment, the cartridge 3622 has a port (through hole) 3620b in the wall. This port 3620b lines up substantially with a channel 3630a in the cartridge piston 3630, and the channel 3635a in the spike 3635. When the cartridge 3622 is initially inserted, the spike 3635 will pierce the foil 3642 adhered to the face of the accumulator piston 3641. In one embodiment, this allows the drive fluid to flow into the channel 3635a in the spike 3635 and the channel 3630a, and out through the port 3620b in the cartridge 3622, as the accumulator piston 3641 is pushed into the body of the manifold 3645. In one embodiment, the outer diameter of the cartridge 3622 slides against the wings of the radial seal 3647, pushing the accumulator piston 3641 in until the end of the cartridge 3622 has passed through the radial seal 3647, and reaches its fully inserted position. This compresses the radial seal 3647 between the cartridge 3622 and the manifold 3645, creating a seal around the entire perimeter of the end of the cartridge 3622.

In one embodiment, after the cartridge 3622 is inserted, and the accumulator piston 3641 is pushed back past the radial seal 3647, there is a path for excess drive fluid to leave the manifold 3645.

Figure 36A:
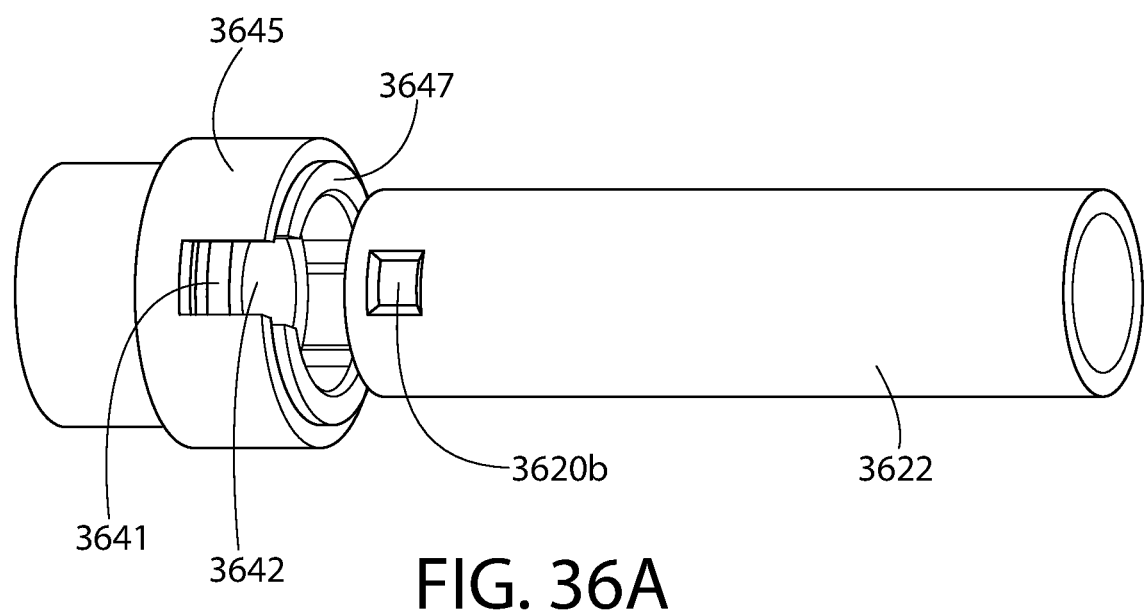
FIG. 36A is a trimetric view of the cartridge and manifold of a fluid delivery device in accordance with an exemplary embodiment of the present invention with the cartridge ready to be inserted.
Figure 36B:
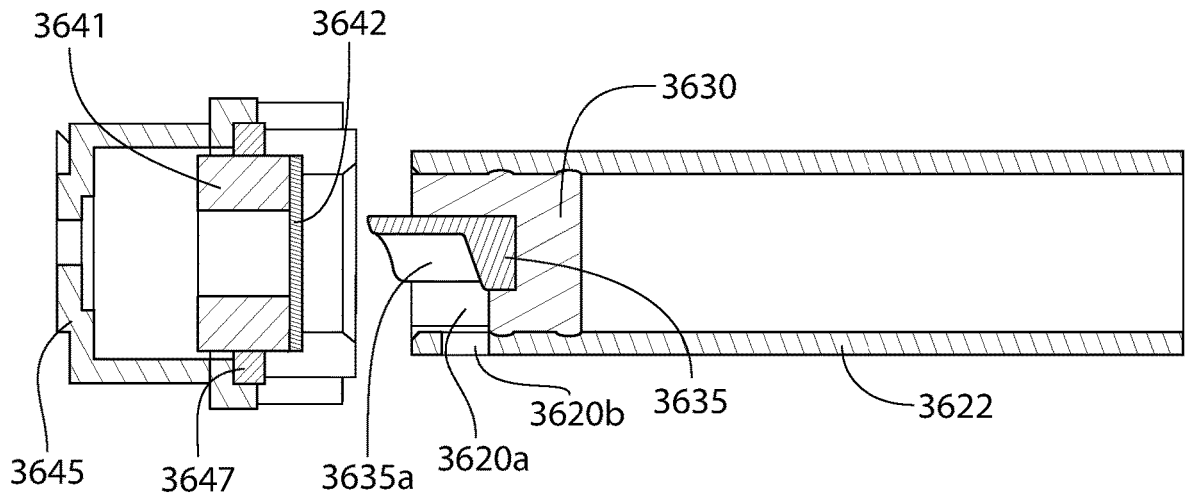
FIG. 36B is a cross section side view of the cartridge and manifold shown in FIG. 36A with the cartridge ready to be inserted.
Figure 36C:
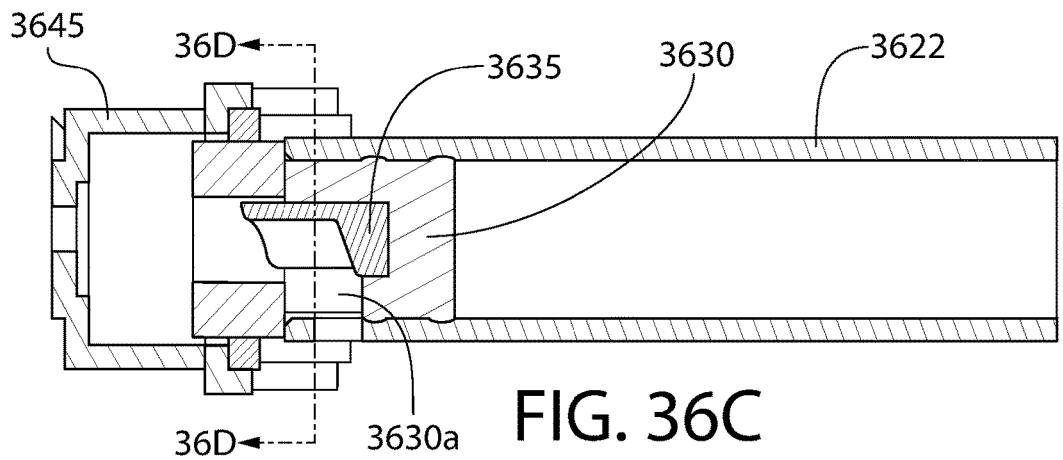
FIG. 36C is a cross section side view of the cartridge and manifold shown in FIG. 36A with the cartridge inserted.
Figure 36D:
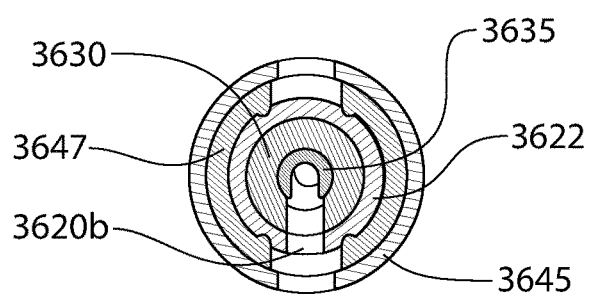
FIG. 36D is a cross section end view of the cartridge and manifold shown in FIG. 36A with the cartridge inserted.
Figure 36E:
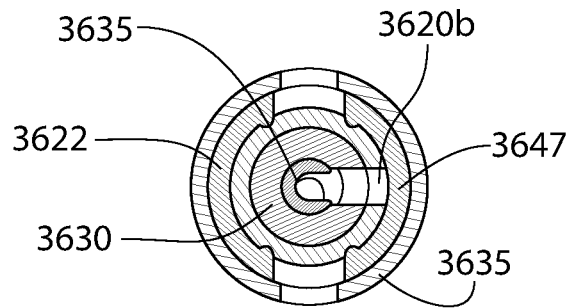
FIG. 36E is a cross section end view of the cartridge and manifold shown in FIG. 36A with the cartridge inserted and rotated.
Figure 37A:
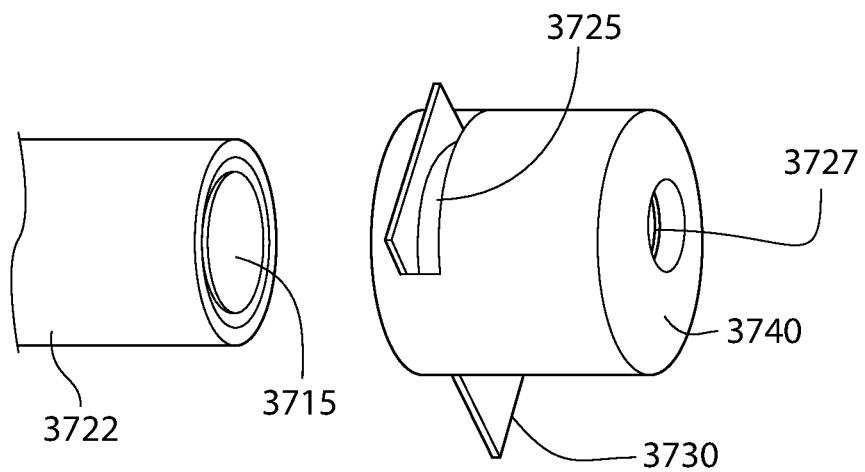
FIG. 37A is a trimetric view of a cartridge and manifold of a fluid delivery device in accordance with an exemplary embodiment of the present invention with the cartridge ready to be inserted.
Figure 37B:
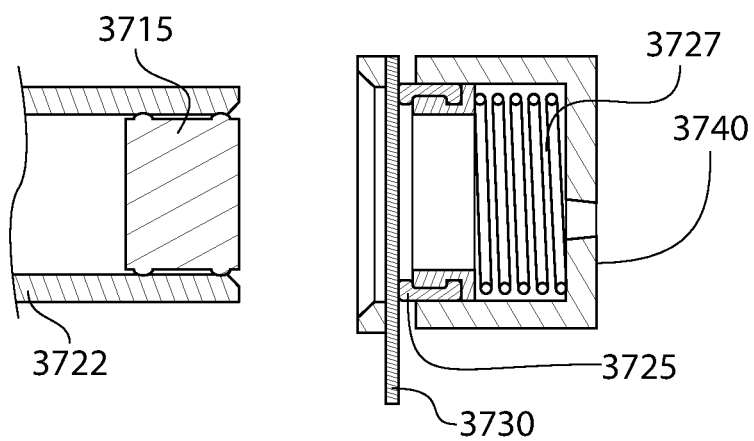
FIG. 37B is a cross section side view of the cartridge and manifold shown in FIG. 37A with the cartridge ready to be inserted.
Figure 37C:
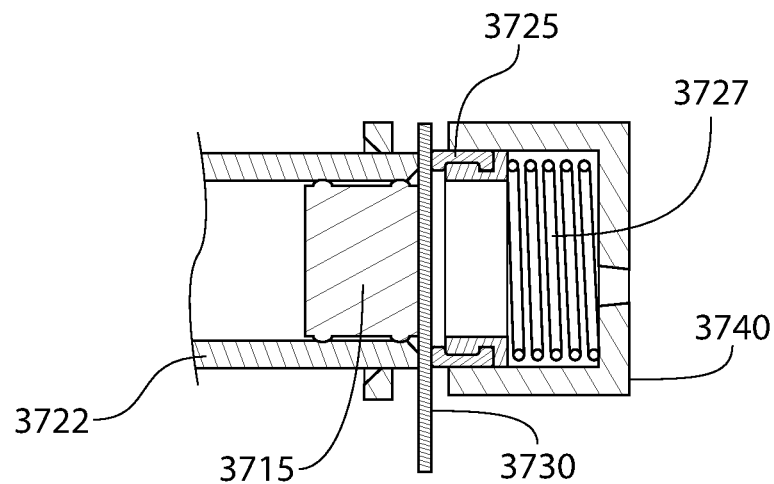
FIG. 37C is a cross section side view of the cartridge and manifold shown in FIG. 37A with the cartridge inserted.
Figure 37D:
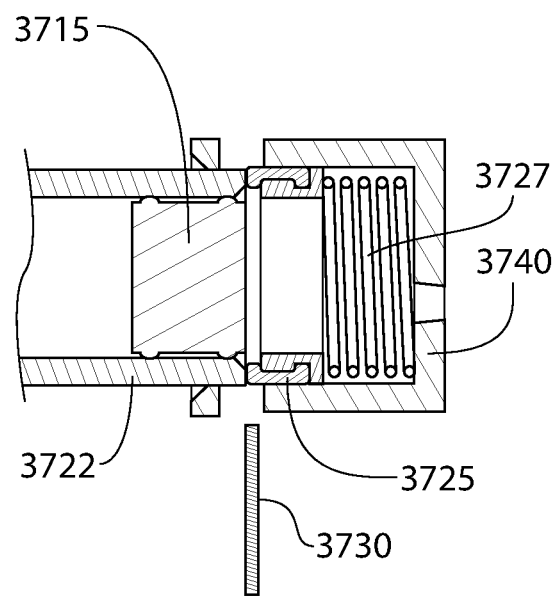
FIG. 37D is a cross section side view of the cartridge and manifold shown in FIG. 37A with the cartridge inserted and sealing shutter removed.

In one embodiment, after the cartridge 3622 has been inserted, it can be rotated such that the port 3620b in the cartridge 3622 is covered by one of the "wings" on the face seal 3647, blocking the path for the drive fluid to leave the manifold 3645, and sealing the cartridge 3622 (See FIG. 36E).

In one embodiment, alternatively, the port 3620b in the wall of the cartridge 3622 could be a notch in the leading edge of the wall of the cartridge, so long as there is a continuous seal around the outside of the cartridge 3622 after the cartridge has been rotated. In one embodiment, alternatively, when the cartridge has been inserted, the end of the cartridge 3622 could seal against the accumulator piston 3641, and the accumulator piston 3641 has been pushed until it seals against the manifold 3645.

In one embodiment, the spike 3635 could be integral with the piston 3630.

Referring to FIGS. 37A-37D, in one embodiment, the end of the cartridge 3722 and the end of the cartridge piston 3715 are essentially flush. When the cartridge 3722 is inserted into the manifold 3740, the cartridge 3722 will contact, and then push back, the shutter 3730. The shutter 3730 is sealed against the face seal 3725, which is pressed against the shutter 3730 by the spring 3727, and is also sealed against the manifold 3740 by a sliding seal along the inside of the manifold 3740. In one embodiment, the face seal 3725 is shown as over-molded elastomer over a rigid component. In one embodiment, the face seal 3725 is one material. In one embodiment, the face seal 3725 has separate sealing elements, such as o-rings or quad-rings.

In one embodiment, the cartridge 3722 pushes back the shutter 3730 until the cartridge 3722 reaches its final position, sliding the face seal 3725 down the bore in the manifold 3740, compressing the spring 3727. Then the shutter 3730 is removed or moved such that the face seal 3725 is pushed into contact with the cartridge 3722 by the spring 3727, forming a seal against the cartridge 3722, allowing the drive fluid to push against the cartridge piston 3715 when the device is activated.

In one embodiment, the shutter 3730 is a membrane.

In one embodiment, the spring 3727 could be some compressible or deformable material, including the elastomeric material of the face seal 3725.

Figure 38A:
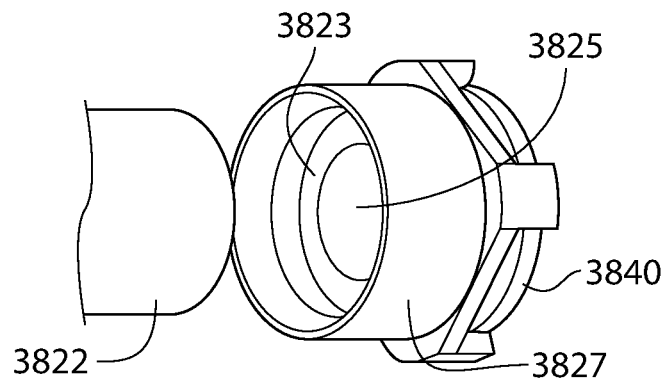
FIG. 38A is a trimetric view of a cartridge and manifold of a fluid delivery device in accordance with an exemplary embodiment of the present invention with the cartridge ready to be inserted.
Figure 38B:
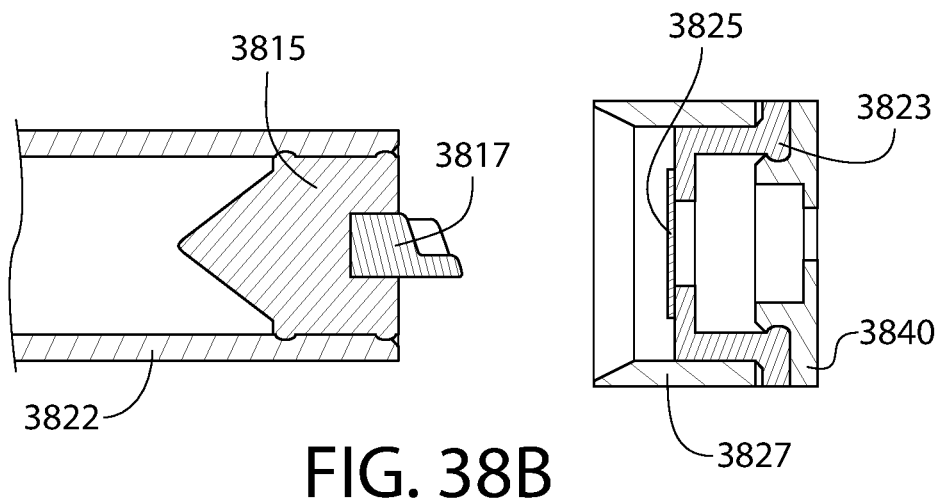
FIG. 38B is a cross section side view of the cartridge and manifold shown in FIG. 38A with the cartridge ready to be inserted.
Figure 38C:
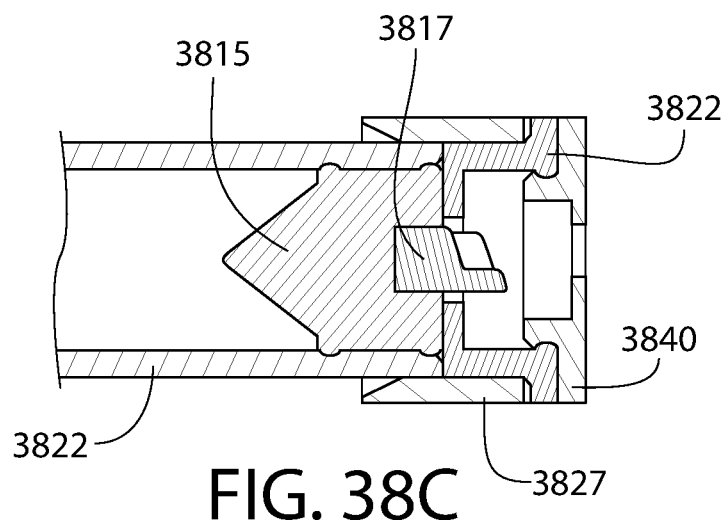
FIG. 38C is a cross section side view of the cartridge and manifold shown in FIG. 38A with the cartridge inserted and the pierced membrane removed for clarity.

Referring to FIGS. 38A-38C, in one embodiment, the drive fluid is sealed into the manifold (only the output end is shown) 3840 by a pierceable membrane 3825 prior to the insertion of a separate cartridge. When the cartridge 3822 is initially inserted, the rigid spike 3817 in the cartridge piston 3815 pierces the membrane 3825 adhered to the face of the elastomeric face seal 3823. In one embodiment, the cartridge 3820 travels farther, during insertion, and compresses the face seal 3823 creating a seal between the face seal 3823 and the cartridge 3822. The membrane perforation allows the drive fluid to flow within the face seal through the hole created in the foil (not shown) by the spike 3817 to the rear face of the cartridge piston 3815.

In one embodiment, the face seal 3823 is held in place by the collar 3827 which is fixed to the manifold 3840, creating a seal.

In one embodiment, the spike 3817 could be integral with the cartridge piston 3815.

Figure 39A:
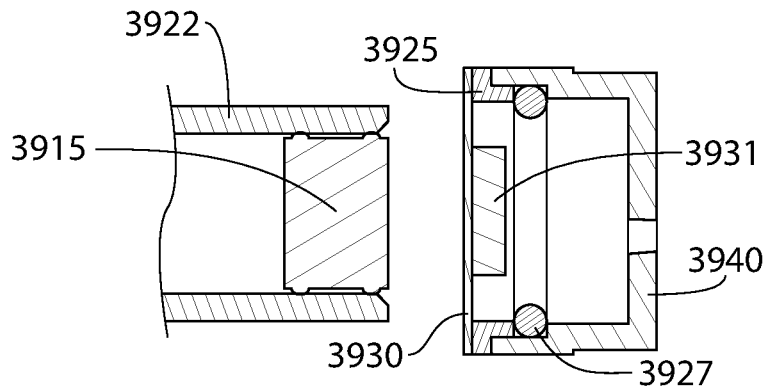
Figure 39B:
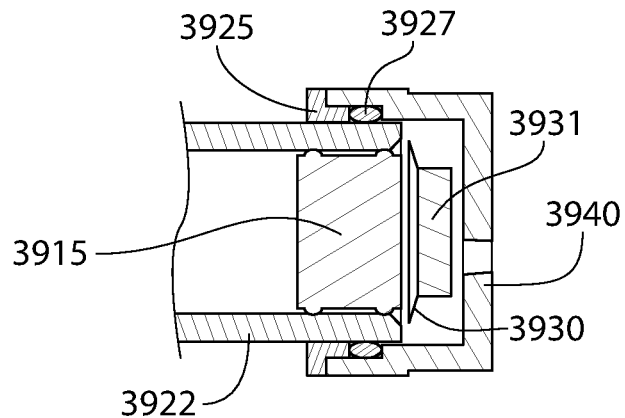

Referring to FIGS. 39A-39B, in one embodiment, the drive fluid is sealed into the manifold 3940 by a pierceable membrane 3930 prior to the insertion of a separate cartridge 3922. The cartridge 3922 has the cartridge piston 3915 essentially flush with the end of the cartridge 3922. The cartridge 3922 is inserted, and punches through the membrane 3930 which is bonded to both a stiffening plug 3931 and a capture ring 3925. In one embodiment, the capture ring 3925 is fixed to the manifold 3940, holding an o-ring 3927.

In one embodiment, the gap between the edge of the stiffening plug 3931 and the capture ring 3925 is less than the distance between the membrane 3930 and the o-ring 3927, so that when the membrane 3930 has been broken, no part of the membrane 3930 that is still attached to the capture ring capture ring 3925 can extend past the o-ring 3927, to compromise the seal created between the o-ring 3927 and the outer diameter of the cartridge 3922. The stiffening plug 3931 is smaller in maximum size than the internal diameter of the cartridge 3922, so that the stiffening plug 3931 cannot block the flow of the drive fluid to the piston 3915.

In one embodiment, the face of the capture ring is at an angle to the axis of the cartridge 3922, or non-planar, so when the cartridge 3922 comes in contact with the membrane 3930, it makes contact at one, or more, points, rather than along the entire perimeter of the end of the cartridge 3922 simultaneously. In one embodiment, the end of the cartridge is nonplanar.

In one embodiment, the stiffening plug 3931 is larger than the internal diameter of the cartridge 3922, but non-planar, such that it is impossible for the stiffening plug 3931 to block the flow of the drive fluid.

In one embodiment, the o-ring 3927 is replaced by some other sealing member, including but not limited to over-molding.

In one embodiment, the capture ring 3925 is combined with the manifold 3940 as a single part.

In one embodiment, the capture ring 3925 is combined with the o-ring 3927 as a single part adhered to, or over-molded on, the manifold 3940.

Figure 40A:
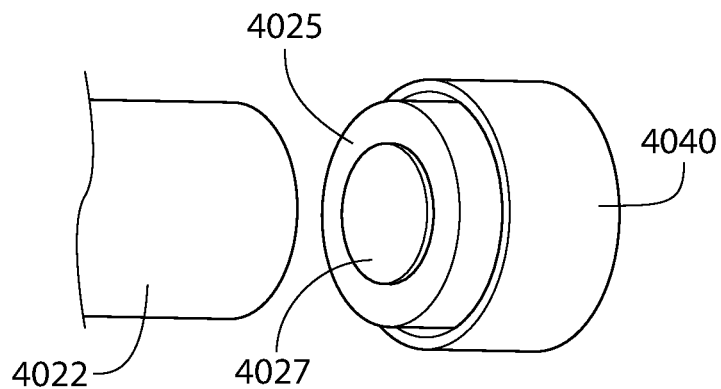
Figure 40B:
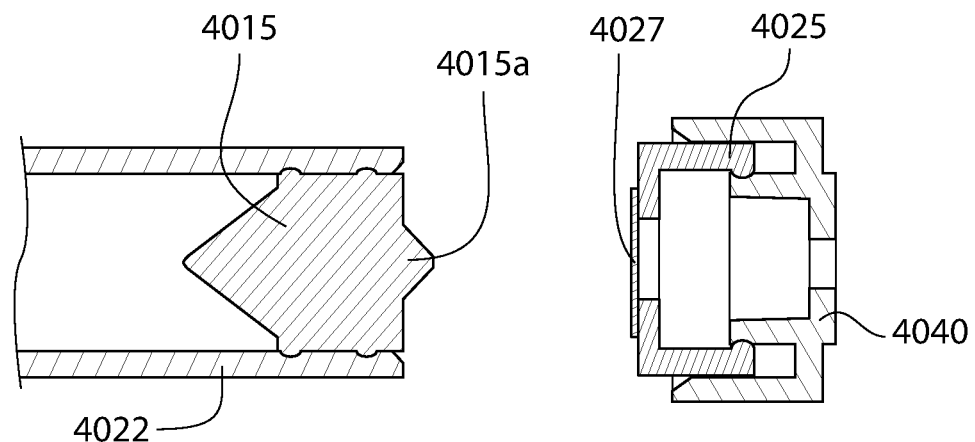
Figure 40C:
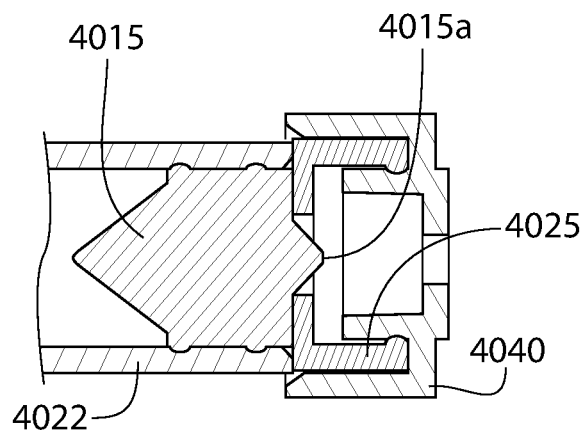

Referring to FIGS. 40A-40F, in one embodiment, the drive fluid is sealed into the manifold 4040 by a pierceable membrane 4027 prior to the insertion of a separate cartridge (FIG. 40A). When the cartridge 4022 is initially inserted, the protrusion 4015a on the piston 4015 will pierce the membrane 4027 adhered to the face of the elastomeric face seal 4025 (FIG. 40C). In one embodiment, the face seal 4025 is aligned by the interaction of the face seal's outer diameter and the outer ring of the manifold 4040. In one embodiment, the face seal 4025 forms a seal to the manifold 4040 on the inside of the face seal ring and an interior surface of the manifold 4040.

In one embodiment, during insertion, the cartridge 4022 pushes and then compresses the face seal 4025 axially against a perpendicular surface of the manifold 4040, creating a seal between the cartridge 4022 and the face seal 4025, and the face seal 4025 and the manifold 4040.

In one embodiment, the spike 4015a could be a separate part from the piston 4015.

In one embodiment, the face seal 4025 could be made of multiple components or materials.

In one embodiment, the face seal 4025 is fixed in place at the final position.

Figure 40D:
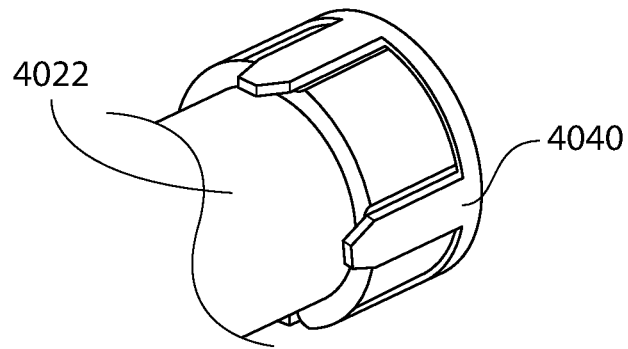

In one embodiment, the outer ring of the manifold is non-continuous. (FIG. 40D)

In one embodiment, the outer ring of the manifold 4040 is completely removed.

Figure 40E:
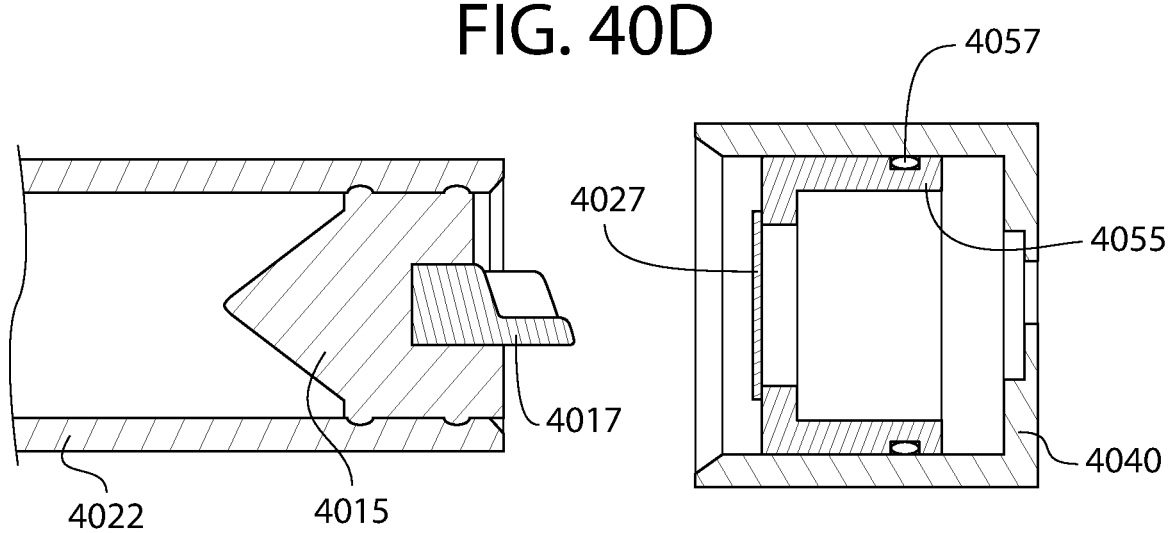
Figure 40F:
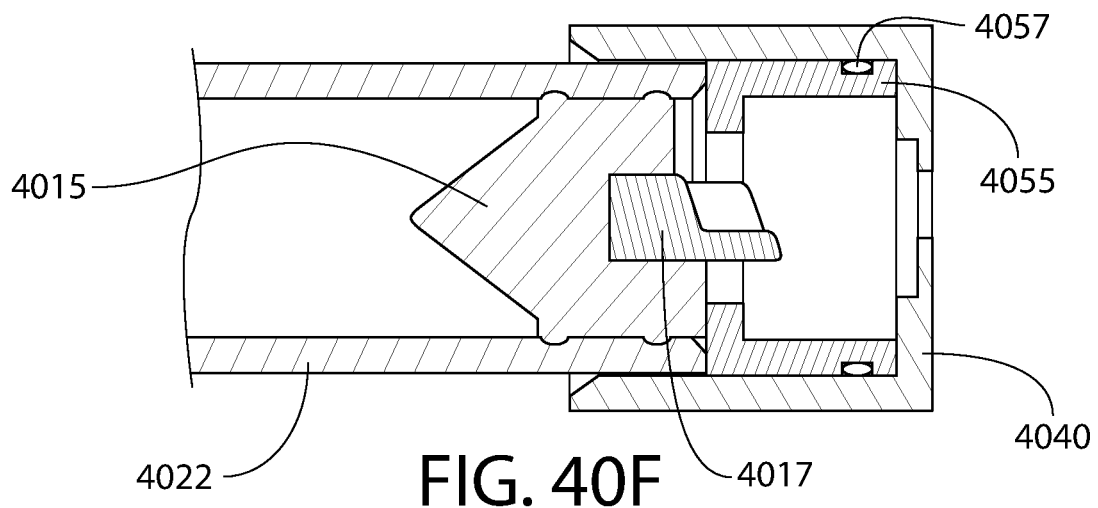

Referring to FIGS. 40E-40F, in one embodiment, the drive fluid is sealed into the manifold 4040 by a pierceable membrane 4027 prior to the insertion of a separate cartridge (FIG. 40F). The cartridge 4022 is initially inserted, the spike 4017 on the piston 4015 pierces the membrane 4027 adhered to the face of the elastomeric face seal 4055 (FIG. 40F) and a sealing element 4057 around the outer surface of the face seal 4055 creates a sliding seal between the manifold 4050 and the face seal 4055.

In one embodiment, the cartridge 4022 pushes the face seal 4055 creating a seal between the face seal 4055 and the cartridge 4022. In one embodiment, this seal could be achieved with a separate component, such as a quad-ring, or an over-molded elastomer. In one embodiment, there could be a sealing element between the cartridge and the manifold 4040.

In one embodiment, the spike 4017 is integral with the cartridge piston 4015.

In one embodiment, the o-ring 4057 is some other sealing element, such as a quad-ring, or an over-molded elastomer.

In one embodiment, the face seal 4055 is elastomeric, and combined with the o-ring.

Referring to FIG. 41A-41D, in one embodiment, the drive fluid is sealed into the manifold 4140 by a deformable face seal 4130 (FIG. 41A). In one embodiment, the end of the cartridge 4122 and the end of the cartridge piston 4115 are offset by a specific distance. When the cartridge 4122 is inserted into the manifold 4140 it will contact, and then push back the deformable face seal 4130 while sliding over the hollow core 4125 until piston 4115 contacts hollow core 4125. In one embodiment, the deformation of the deformable face seal 4130 results in a pathway opening for the drive fluid to flow. In one embodiment, the cartridge 4122 is sealed against the face of the deformable face seal 4130.

Referring to FIGS. 42A-42B, in one embodiment, the drive fluid is sealed into the manifold 4240 by a pierceable membrane 4245 prior to the insertion of a separate cartridge (FIG. 42A).

In one embodiment, when the cartridge 4222 is initially inserted, the hollow spike 4225 in the piston 4230 will pierce the membrane 4245 adhered to the face of the radial seal 4240a. In one embodiment, the hollow opening in the spike 4225 will allow the transfer of the drive fluid down toward the cartridge piston 4230 displacing air entrapment. In one embodiment, the sliding radial seal is held in place by the manifold 4240, creating a seal.

In one embodiment, the cartridge 4222 travels farther, compressing the o-ring seal 4250 and creating a radial seal between the sliding radial seal 4240a and the cartridge 4222. This seal contains the drive fluid that flows through the hole in the foil (not shown) created by the spike 4225 when the drive fluid is activated forcing it to act on the cartridge piston 4230.

In one embodiment, the spike 4225 could be integral with the cartridge piston 4230. In one embodiment, the radial seal is over-molded elastomer over a rigid component, or could be one material.

Referring to FIGS. 43A-43B, in one embodiment, a linearly actuated valve, actuated by the insertion of the cartridge assembly 4322 into the delivery device 4310, opens flow to the cartridge 4322 while shutting off communication to the storage temperature compensation system. The stem 4315 is inserted into an opening of a valve body 4325, which is sealed into manifold 4330. The stem 4315 inserted into the top of the seat 4325 seals the drive system during storage, before use and contains the drive fluid during use. The internal volume of the manifold 4330 fluidly communicates to an internal chamber of the valve body 4325 through ports 4325a. During storage these ports can communicate to the storage temperature compensation system through port 4325b. The storage temperature compensation system is comprised of a chamber in the center of the stem 4315, passage through the valve stem 4315a, and a flexible membrane 4340. The flexible membrane 4340 accommodates the change in drive fluid volume without imparting a significant force on the drive fluid. The non-drive fluid contact side of the flexible membrane 4340 is also vented to atmosphere. (FIG. 43A).

When the cartridge assembly 4322 is installed into delivery device 4310, the cartridge piston 4345 and vial 4343 push on the valve stem 4315. As the valve stem 4315 moves into the valve body 4325, ports 4325a are isolated from the storage temperature compensation system and allowed to communicate with the annular space around stem 4315 and through the passages 4315b in the top of stem 4315. Air trapped by the insertion of cartridge assembly 4322 is vented to atmosphere through passage 4325*b*, once the cartridge 4322 has become radially sealed by O-ring 4335. This allows for flow from the manifold through ports 4325*a* around stem 4315 and up internal passages of the valve stem 4315*a* to displace the cartridge piston 4345 while preventing leakage out of the system (FIG. 43B).

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A fluid delivery device comprising:
   a housing having a bottom surface configured to be coupled to a skin surface, the housing including a hydraulic fluid drive containing a hydraulic fluid, the hydraulic fluid drive including a first hydraulic chamber and a second hydraulic chamber, the first hydraulic chamber being fluidly coupled to the second hydraulic chamber by a flow restrictor;
   a cartridge prefilled with a fluid and configured to be inserted into the housing, the cartridge having a septum; and
   a needle assembly having a needle including a fluid coupling end and a delivery end, the fluid coupling end of the needle being fluidly disengaged from the cartridge in an initial position, the delivery end of the needle extending past a plane co-planar with the bottom surface in a deployed position and the fluid coupling end of the needle extending through the septum in the deployed position,
   wherein the hydraulic fluid drive includes a port configured to couple with the cartridge, the port having a seal that is closed prior to inserting the cartridge into the housing and released when the cartridge is coupled with the port, the cartridge including a piston moveable by the hydraulic fluid when the needle is in the deployed position,
   wherein the seal includes a slideable valve having one or more fluid passages configured to fluidly couple the hydraulic fluid drive and the piston.

2. The delivery device of claim 1, wherein the one or more fluid passages are filled with a fluid prior to the cartridge being inserted into the housing.

3. The fluid delivery device of claim 1, wherein the septum is generally perpendicular to the bottom surface when the cartridge is inserted in the housing.

4. A fluid delivery device comprising:
   a housing having a bottom surface configured to be coupled to a skin surface, the housing including a hydraulic fluid drive containing a hydraulic fluid, the hydraulic fluid drive including a first hydraulic chamber and a second hydraulic chamber, the first hydraulic chamber being fluidly coupled to the second hydraulic chamber by a flow restrictor;
   a cartridge prefilled with a fluid and configured to be inserted into the housing, the cartridge having a septum; and
   a needle assembly having a needle including a fluid coupling end and a delivery end, the fluid coupling end of the needle being fluidly disengaged from the cartridge in an initial position, the delivery end of the needle extending past a plane co-planar with the bottom surface in a deployed position and the fluid coupling end of the needle extending through the septum in the deployed position,
   wherein the hydraulic fluid drive includes a port configured to couple with the cartridge, the port having a seal that is closed prior to inserting the cartridge into the housing and released when the cartridge is coupled with the port, the cartridge including a piston moveable by the hydraulic fluid when the needle is in the deployed position,
   wherein the hydraulic fluid drive is fluidly coupled to an accumulator configured to allow thermal expansion and contraction of the hydraulic fluid.

5. The fluid delivery device of claim 4, wherein the accumulator is fluidly coupled to the hydraulic fluid drive when the seal is closed and fluidly disengaged from the hydraulic fluid drive when the seal is released.

6. A fluid delivery device comprising:
   a housing having a bottom surface configured to be coupled to a skin surface, the housing including a hydraulic fluid drive containing a hydraulic fluid, the hydraulic fluid drive including a first hydraulic chamber and a second hydraulic chamber, the first hydraulic chamber being fluidly coupled to the second hydraulic chamber by a flow restrictor;
   a cartridge prefilled with a fluid and configured to be inserted into the housing, the cartridge having a septum; and
   a needle assembly having a needle including a fluid coupling end and a delivery end, the fluid coupling end of the needle being fluidly disengaged from the cartridge in an initial position, the delivery end of the needle extending past a plane co-planar with the bottom surface in a deployed position and the fluid coupling end of the needle extending through the septum in the deployed position,
   wherein the hydraulic fluid drive includes a port configured to couple with the cartridge, the port having a seal that is closed prior to inserting the cartridge into the housing and released when the cartridge is coupled with the port, the cartridge including a piston moveable by the hydraulic fluid when the needle is in the deployed position, wherein the port includes a ball joint receiver that is at an acute angle relative to the bottom surface of the housing until the cartridge is retained in place relative to the housing.

7. A fluid delivery device comprising:
a housing having a bottom surface configured to be coupled to a skin surface, the housing including a hydraulic fluid drive containing a hydraulic fluid, the hydraulic fluid drive including a first hydraulic chamber and a second hydraulic chamber, the first hydraulic chamber being fluidly coupled to the second hydraulic chamber by a flow restrictor;
a cartridge prefilled with a fluid and configured to be inserted into the housing, the cartridge having a septum; and
a needle assembly having a needle including a fluid coupling end and a delivery end, the fluid coupling end of the needle being fluidly disengaged from the cartridge in an initial position, the delivery end of the needle extending past a plane co-planar with the bottom surface in a deployed position and the fluid coupling end of the needle extending through the septum in the deployed position, wherein the hydraulic fluid drive includes a port configured to couple with the cartridge, the port having a seal that is closed prior to inserting the cartridge into the housing and released when the cartridge is coupled with the port, the cartridge including a piston moveable by the hydraulic fluid when the needle is in the deployed position, wherein the piston includes a spike configured to pierce the seal when the cartridge is coupled with the port.

* * * * *